(12) United States Patent
Moghimi et al.

(10) Patent No.: US 11,000,599 B2
(45) Date of Patent: **\*May 11, 2021**

(54) PEPTIDIC SELF-ASSEMBLY FOR NUCLEIC ACID DELIVERY

(71) Applicant: S. M. Discovery Group Inc., Centennial, CO (US)

(72) Inventors: Seyed Moien Moghimi, København (DK); Linping Wu, Søborg (DK); Davoud Ahmadvand, Søborg (DK); Ladan Parhamifar, Fredriksberg (DK)

(73) Assignee: S. M. Discovery Group Inc., Centennial, CO (US)

( \* ) Notice: Subject to any disclaimer, the term of this patent is extended or adjusted under 35 U.S.C. 154(b) by 0 days.

This patent is subject to a terminal disclaimer.

(21) Appl. No.: 15/991,738

(22) Filed: May 29, 2018

(65) Prior Publication Data

US 2020/0069813 A1 Mar. 5, 2020

Related U.S. Application Data

(63) Continuation of application No. 14/912,997, filed as application No. PCT/EP2014/067651 on Aug. 19, 2014, now Pat. No. 9,981,047.

(30) Foreign Application Priority Data

Aug. 19, 2013 (DK) .......................... PA 2013 70453

(51) Int. Cl.
```
A61K 47/66    (2017.01)
A61K 47/69    (2017.01)
A61K 49/00    (2006.01)
A61K 47/64    (2017.01)
```
(52) U.S. Cl.
CPC .............. *A61K 47/66* (2017.08); *A61K 47/64* (2017.08); *A61K 47/69* (2017.08); *A61K 47/6901* (2017.08); *A61K 47/6911* (2017.08); *A61K 47/6929* (2017.08); *A61K 47/6953* (2017.08); *A61K 49/0002* (2013.01); *A61K 49/0056* (2013.01)

(58) Field of Classification Search
None
See application file for complete search history.

(56) References Cited

U.S. PATENT DOCUMENTS

| | | | |
|---|---|---|---|
| 6,576,257 B1 * | 6/2003 | Yarmut | A61K 41/0028 424/450 |
| 9,981,047 B2 * | 5/2018 | Moghimi | A61K 49/0002 |
| 2002/0115824 A1 | 8/2002 | Engler et al. | |
| 2004/0157767 A1 | 8/2004 | Faulk | |
| 2005/0075268 A1 * | 4/2005 | Berg | A61K 39/0011 514/1 |
| 2010/0160209 A1 | 6/2010 | Doucet et al. | |
| 2012/0258104 A1 | 10/2012 | Echeverri et al. | |

FOREIGN PATENT DOCUMENTS

| WO | WO 2008/050133 A2 | 5/2008 |
|---|---|---|
| WO | WO 2011/005098 A1 | 1/2011 |

OTHER PUBLICATIONS

Fomina et al. "Photochemical mechanisms of light-triggered release from nanocarriers," Adv Drug Deliv Rev. Aug. 2012; 64(11): 1005-1020. (Year: 2012).*
International Search Report and Written Opinion for related International Application No. PCT/EP2014/067651, dated Nov. 25, 2014 (10 pages).
Van Rooy, I., et al., "Attaching the phage display-selected GLA peptide to liposomes: Factors influencing target binding," *European Journal of Pharmaceutical Sciences*, 45(3):330-335 (2012).

\* cited by examiner

*Primary Examiner* — Christina Bradley
(74) *Attorney, Agent, or Firm* — Barnes & Thornburg LLP; Ryan L. Marshall

(57) ABSTRACT

A polypeptide conjugate for use in a method for binding and/or internalization of the polypeptide conjugate to a mammalian cell having a transferrin receptor (TFRC) and/or receptor for advanced glycation end products (RAGE). The polypeptide conjugate may be used in a method for targeting of a drug delivery system or diagnostic delivery system.

20 Claims, 75 Drawing Sheets

Specification includes a Sequence Listing.

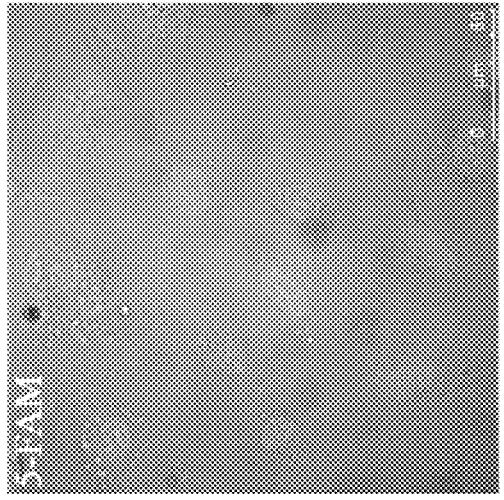
Fig. 7A
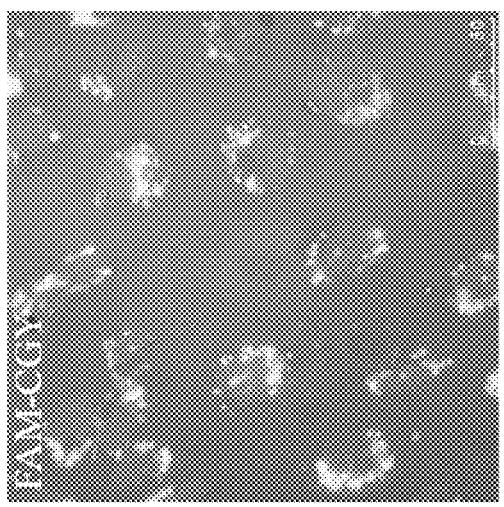
Fig. 7B
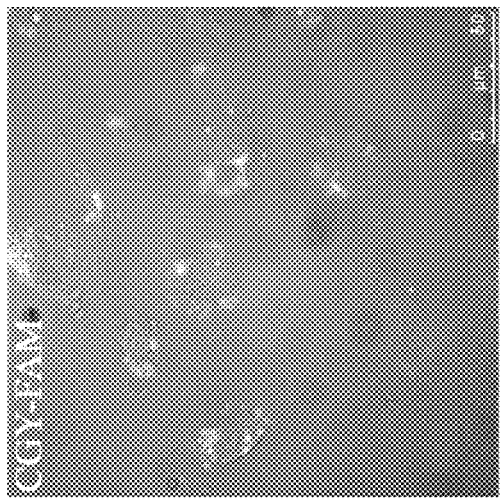
Fig. 7C
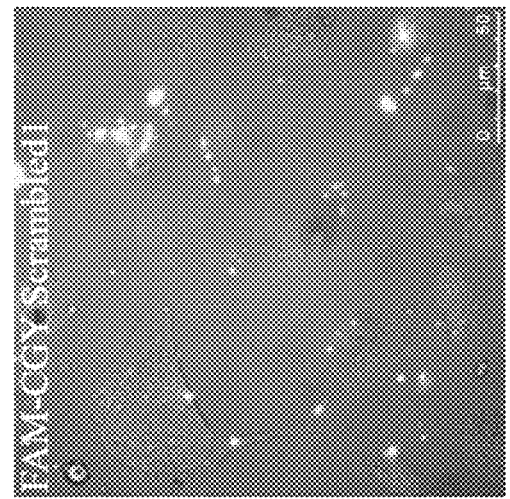
Fig. 7D
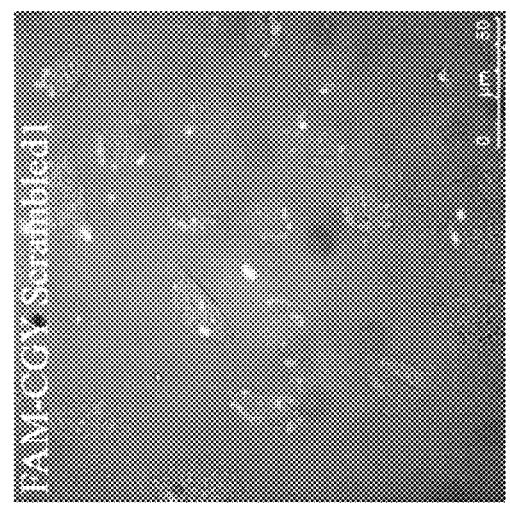
Fig. 7E
Fig. 7F

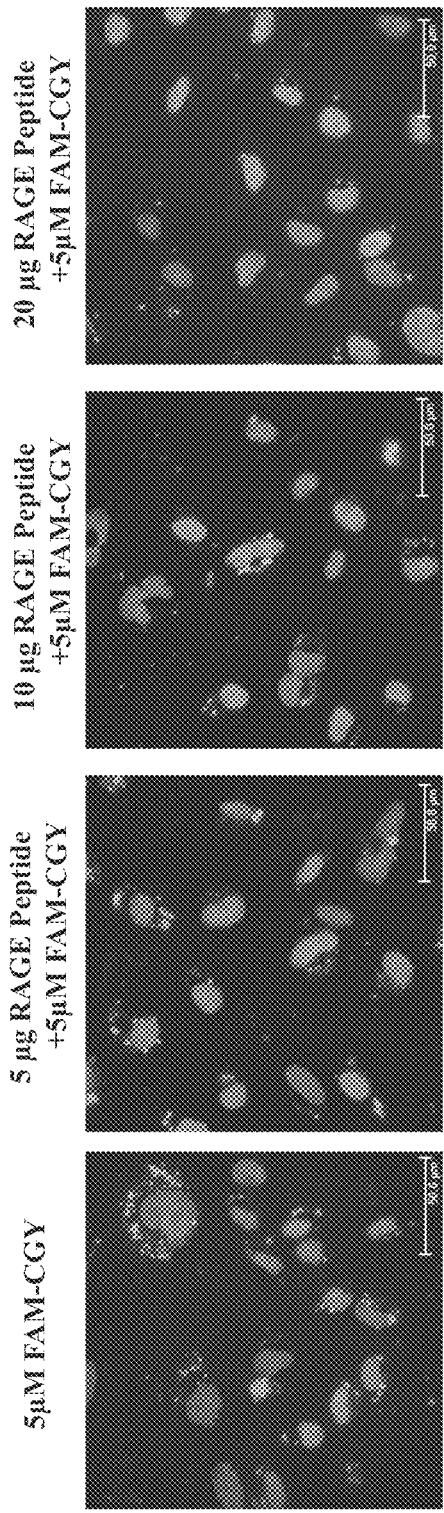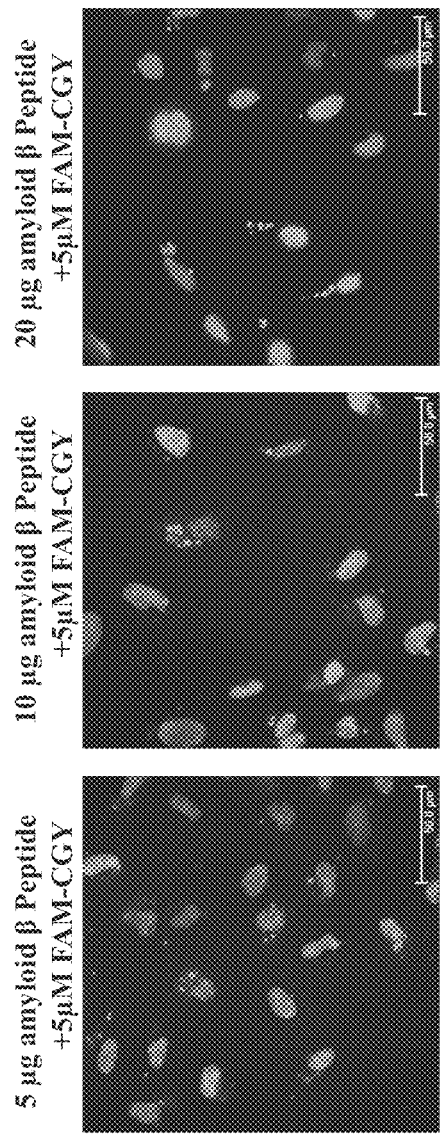

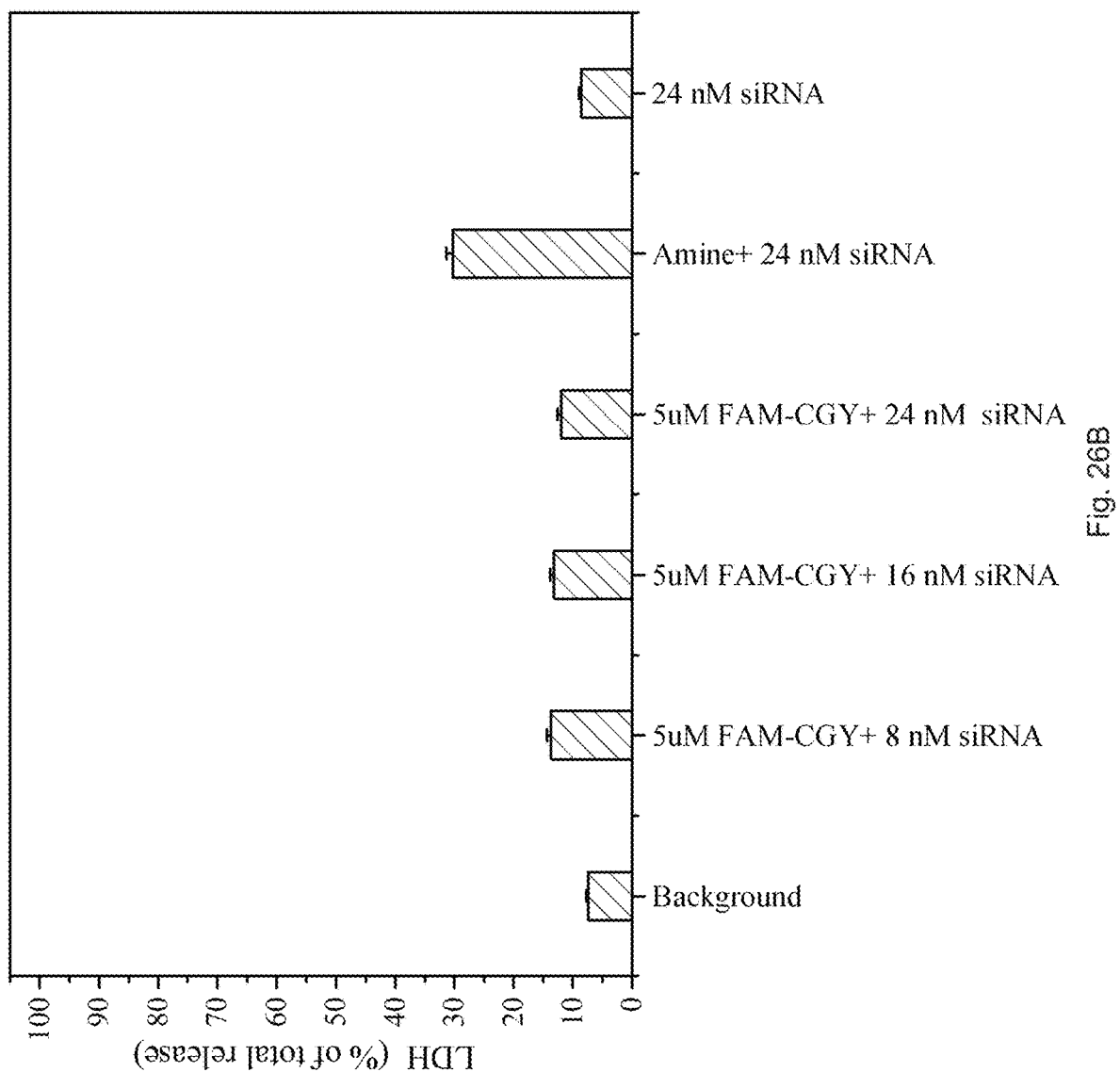

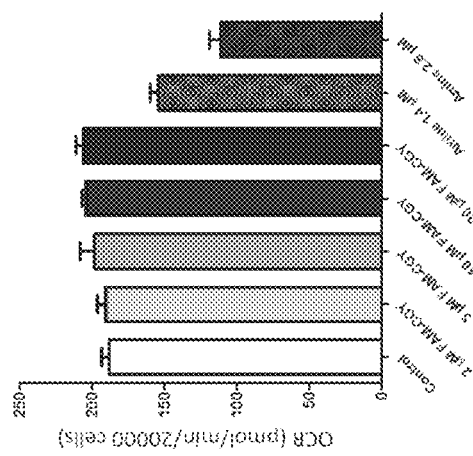
Fig. 27B
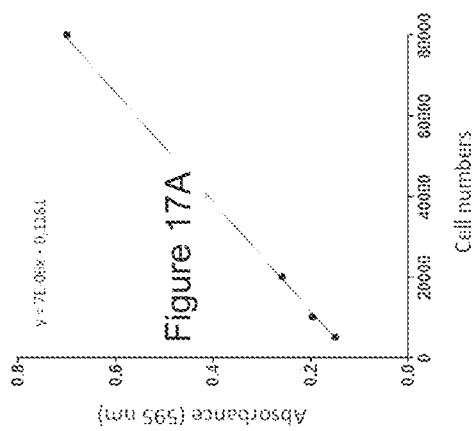
Figure 17A
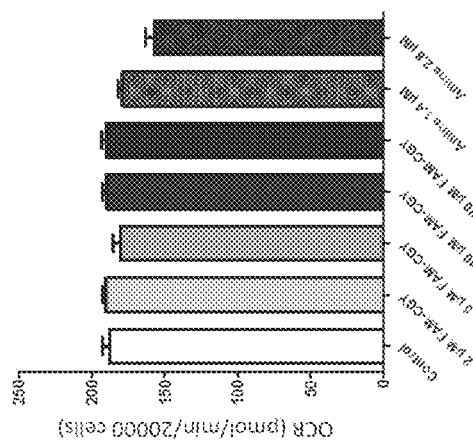
Fig. 27A
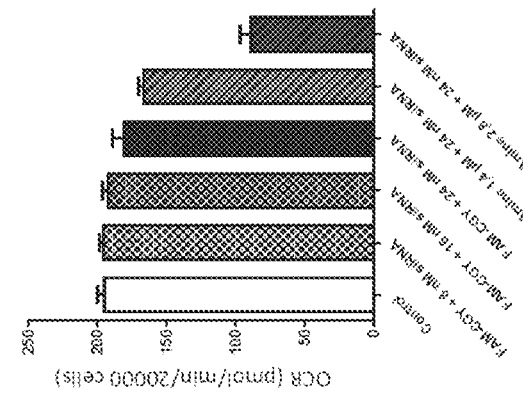
Fig. 27C
Fig. 27D 5-FAM-Cys-Gly-Tyr-Arg-Pro-Val-His-Asn-Ile-Arg-Gly-His-Trp-Ala-Pro-Gly 5-FAM-Cys-Gly-Tyr-Arg-Pro-Val-His-Asn-Ile-Arg-Gly-His-Trp-Ala-Pro-Gly-Gly-Gly-Tyr-Arg-Pro-Val-His-Asn-Ile-Arg-Gly-His-Trp-Ala-Pro-Gly

SEQUENCE LISTING

```
<160> NUMBER OF SEQ ID NOS: 8

<210> SEQ ID NO 1
<211> LENGTH: 15
<212> TYPE: PRT
<213> ORGANISM: Artificial Sequence
<220> FEATURE:
<223> OTHER INFORMATION: artificial peptide conjugate

<400> SEQUENCE: 1

Gly Tyr Arg Pro Val His Asn Ile Arg Gly His Trp Ala Pro Gly
1               5                   10                  15

<210> SEQ ID NO 2
<211> LENGTH: 31
<212> TYPE: PRT
<213> ORGANISM: Artificial Sequence
<220> FEATURE:
<223> OTHER INFORMATION: artificial peptide

<400> SEQUENCE: 2

Gly Tyr Arg Pro Val His Asn Ile Arg Gly His Trp Ala Pro Gly Gly
1               5                   10                  15

Gly Tyr Arg Pro Val His Asn Ile Arg Gly His Trp Ala Pro Gly
            20                  25                  30

<210> SEQ ID NO 3
<211> LENGTH: 16
<212> TYPE: PRT
<213> ORGANISM: Artificial Sequence
```

```
<220> FEATURE:
<223> OTHER INFORMATION: artificial peptide CGY

<400> SEQUENCE: 3

Cys Gly Tyr Arg Pro Val His Asn Ile Arg Gly His Trp Ala Pro Gly
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: artificial peptide FAM-CGY
<220> FEATURE:
<221> NAME/KEY: misc_feature
<222> LOCATION: (1)..(1)
<223> OTHER INFORMATION: a fluorophore (e.g.,5-FAM) is attached to Cys

<400> SEQUENCE: 4

Cys Gly Tyr Arg Pro Val His Asn Ile Arg Gly His Trp Ala Pro Gly
1               5                   10                  15

<210> SEQ ID NO 5
<211> LENGTH: 17
<212> TYPE: PRT
<213> ORGANISM: Artificial Sequence
<220> FEATURE:
<223> OTHER INFORMATION: artificial peptide CGY-FAM
<220> FEATURE:
<221> NAME/KEY: misc_feature
<222> LOCATION: (17)..(17)
<223> OTHER INFORMATION: a fluorophore (e.g., 5-FAM) is attached to Lys

<400> SEQUENCE: 5

Cys Gly Tyr Arg Pro Val His Asn Ile Arg Gly His Trp Ala Pro Gly
1               5                   10                  15

Lys

<210> SEQ ID NO 6
<211> LENGTH: 16
<212> TYPE: PRT
<213> ORGANISM: Artificial Sequence
<220> FEATURE:
<223> OTHER INFORMATION: D-amino acid peptide (FAM-d-CGY)
<220> FEATURE:
<221> NAME/KEY: misc_feature
<222> LOCATION: (1)..(1)
<223> OTHER INFORMATION: a fluorophore (e.g., 5-FAM) is attached to Xaa
<220> FEATURE:
<221> NAME/KEY: X
<222> LOCATION: (1)..(1)
<223> OTHER INFORMATION: Where XAA symbolizes D-Cys.
<220> FEATURE:
<221> NAME/KEY: X
<222> LOCATION: (2)..(2)
<223> OTHER INFORMATION: Where XAA symbolizes D-Gly.
<220> FEATURE:
<221> NAME/KEY: X
<222> LOCATION: (3)..(3)
<223> OTHER INFORMATION: Where XAA symbolizes D-Tyr.
<220> FEATURE:
<221> NAME/KEY: X
<222> LOCATION: (4)..(4)
<223> OTHER INFORMATION: Where XAA symbolizes D-Arg.
<220> FEATURE:
<221> NAME/KEY: X
<222> LOCATION: (5)..(5)
<223> OTHER INFORMATION: Where XAA symbolizes D-Pro.
```

```
<220> FEATURE:
<221> NAME/KEY: X
<222> LOCATION: (6)..(6)
<223> OTHER INFORMATION: Where XAA symbolizes D-Val.
<220> FEATURE:
<221> NAME/KEY: X
<222> LOCATION: (7)..(7)
<223> OTHER INFORMATION: Where XAA symbolizes D-His.
<220> FEATURE:
<221> NAME/KEY: X
<222> LOCATION: (8)..(8)
<223> OTHER INFORMATION: Where XAA symbolizes D-Asn.
<220> FEATURE:
<221> NAME/KEY: X
<222> LOCATION: (9)..(9)
<223> OTHER INFORMATION: Where XAA symbolizes D-Ile.
<220> FEATURE:
<221> NAME/KEY: X
<222> LOCATION: (10)..(10)
<223> OTHER INFORMATION: Where XAA symbolizes D-Arg.
<220> FEATURE:
<221> NAME/KEY: X
<222> LOCATION: (11)..(11)
<223> OTHER INFORMATION: Where XAA symbolizes D-Gly.
<220> FEATURE:
<221> NAME/KEY: X
<222> LOCATION: (12)..(12)
<223> OTHER INFORMATION: Where XAA symbolizes D-His.
<220> FEATURE:
<221> NAME/KEY: X
<222> LOCATION: (13)..(13)
<223> OTHER INFORMATION: Where XAA symbolizes D-Trp.
<220> FEATURE:
<221> NAME/KEY: X
<222> LOCATION: (14)..(14)
<223> OTHER INFORMATION: Where XAA symbolizes D-Ala.
<220> FEATURE:
<221> NAME/KEY: X
<222> LOCATION: (15)..(15)
<223> OTHER INFORMATION: Where XAA symbolizes D-Pro.
<220> FEATURE:
<221> NAME/KEY: X
<222> LOCATION: (16)..(16)
<223> OTHER INFORMATION: Where XAA symbolizes D-Gly.

<400> SEQUENCE: 6

Xaa Xaa Xaa Xaa Xaa Xaa Xaa Xaa Xaa Xaa Xaa Xaa Xaa Xaa Xaa Xaa
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: artificial peptide FAM-CGY (Scrambled 1)
<220> FEATURE:
<221> NAME/KEY: misc_feature
<222> LOCATION: (1)..(1)
<223> OTHER INFORMATION: a fluorophore (e.g., 5- FAM) is attached to Cys

<400> SEQUENCE: 7

Cys Gly Tyr Arg Pro Val His Asn Ile Gly His Trp Arg Ala Pro Gly
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: artificial peptide FAM-CGY (Scrambled 2)
```

```
-continued

<220> FEATURE:
<221> NAME/KEY: misc_feature
<222> LOCATION: (1)..(1)
<223> OTHER INFORMATION: a fluorophore (e.g., 5-FAM) is attached to Cys

<400> SEQUENCE: 8

Cys Gly Tyr Arg Pro Val His Asn Ile Arg Gly His Gly Ala Pro Gly
1               5                   10                  15
```

PEPTIDIC SELF-ASSEMBLY FOR NUCLEIC ACID DELIVERY

This application is a continuation of U.S. patent application Ser. No. 14/912,997, filed Feb. 19, 2016, now U.S. Pat. No. 9,981,047, issued May 29, 2018, which is a 371 national phase of International Application No. PCT/EP2014/067651, filed Aug. 19, 2014, and claims priority to Denmark Application No. PA 2013 70453, filed Aug. 19, 2013, the disclosures of which are incorporated, in their entirety, by this reference.

This invention relates to a polypeptide conjugate for use in a method for targeting of a drug delivery system or diagnostic delivery system, targeting at least two receptors.

BACKGROUND

One of the key challenges in medicine is to be able to target therapeutic agents to the desired site of action. If site-specific targeting of drugs can be achieved this will reduce the required therapeutic dose to obtain a beneficial effect and may effectively reduce drug-induced toxicity and adverse effects. One way of achieving these is to use a particulate drug carrier system for drug delivery and targeting. Encapsulation or incorporation of drug molecules in certain drug carriers (e.g., liposomes) can further attain protection against drug degradation or inactivation en-route to the target site.

The biological performance of particulate drug carriers is controlled by a complex array of physicochemical and physiopathological factors, depending on the route of administration. Generally, physicochemical considerations include particle size distribution, shape, rigidity/deformability and surface characteristics (e.g., electric charge, surface-bound polymers and their conformation, surface density of targeting ligands). These factors, for instance, can not only modulate drug carrier circulation times in the blood, but also affect their tissue deposition patterns, mode of entry into cells and intracellular trafficking. Biological considerations that control drug carrier performance include determinants of phagocytic/endocytic recognition and ingestion, the 'state-of-responsiveness' of the host defense system, a wide range of anatomical, physiological and biochemical barriers, and escape routes from vasculature. The blood-brain barrier (BBB) is a formidable gatekeeper in the body, which is formed at the level of the endothelial cells of the cerebral capillaries and essentially composes the major interface between the blood and the brain. Indeed, BBB is the most important anatomical factor limiting the development of new drugs and biologics for the central nervous system. There have been numerous attempts to employ strategies that aid drug passage across the BBB. Among these, nanotechnology-based approaches have gained tremendous importance as some of them are capable of overcoming the limitations inherent to BBB passage, but these approaches are still in need of further optimization to increase their efficacy. One of the most promising approaches for brain targeting is surface decoration of particulate carriers with ligands specific for cerberal capillary endothelial cells, which mediates internalization and/or transcytosis of the bound carrier. In this respect, WO2011/005098 discloses examples of targeting peptides with selectivity towards the human brain capillary endothelial cell line hCMEC/D3 such as the peptide Gly-Tyr-Arg-Pro-Val-His-Asn-Ile-Arg-Gly-His-Trp-Ala-Pro-Gly (SEQ ID NO. 1) that can be grafted to particulate systems (e.g., liposomes). However, in a later publication van Rooy and colleagues (European Journal of Pharmaceutical Sciences 2012, 45, 330-335), demonstrated that the same peptide when coupled to liposomes did not significantly increase liposome uptake by the target brain capillary endothelial cells. Thus, the authors discontinued the project. This illustrates the difficulty in the design and engineering of particulate carriers that can effectively target human brain capillary endothelial cells and promote the internalization of therapeutic and diagnostic agents.

The present invention has chemically modified the same aforementioned peptide SEQ ID NO. 1 (Gly-Tyr-Arg-Pro-Val-His-Asn-Ile-Arg-Gly-His-Trp-Ala-Pro-Gly) describing a polypeptide conjugate (and its other forms thereof) that can efficiently target two receptors for binding and/or internalization. Accordingly, this invention provides a conjugate that can be used for targeting of pharmaceutically acceptable substances such as drugs, diagnostic agents or delivery systems of drugs or diagnostic agents to certain cell types.

SUMMARY

In one aspect, a polypeptide conjugate is disclosed which includes a polypeptide having a polypeptide sequence (SEQ ID NO. 1): Gly-Tyr-Arg-Pro-Val-His-Asn-Ile-Arg-Gly-His-Trp-Ala-Pro-Gly, or a derivative thereof which is at least 80% identical to polypeptide sequence (SEQ ID NO. 1); at least one moiety attached to the polypeptide; and pharmaceutically acceptable salts or esters thereof.

In some embodiments, the at least one moiety is hydrophobic. In some embodiments, the conjugate is in an aggregate form of at least two molecules of the polypeptide conjugate. In some embodiments, the aggregate is a particle of at least about 2 nm in diameter. In some embodiments, the aggregate includes a fiber form in any aspect ratio. In some embodiments, the aggregate comprises a mixture of particles and fibres in free form as well as interconnected particles and fibres. In some embodiments, wherein the at least one moiety is selected from: a drug molecule, a biological molecule, a surface-active agent, a hydrophobic molecule, a fluorescent molecule, and salts thereof. In some embodiments, the at least one moiety is a drug molecule and salts thereof. In some embodiments, the at least one moiety is a biological molecule. In some embodiments, the at least one moiety is a surface-active agent. In some embodiments, the at least one moiety is a hydrophobic molecule and salts thereof. In some embodiments, the at least one moiety is a fluorescent molecule.

In some embodiments, the polypeptide of the conjugate comprises two or more polypeptides of sequence (SEQ ID NO. 1), or derivatives thereof separated by a spacer. In some embodiments, the polypeptide is attached to the at least one moiety via a linker which is a chemical entity or a covalent bond. In some embodiments, the linker is a chemical entity. In some embodiments, the linker is a covalent bond. In some embodiments, the linker is a sulfur-containing amino acid. In some embodiments, the linker is cysteine or a cysteine derivative.

In some embodiments, the spacer is selected from: a chemical entity, covalent bond, or non-covalent bond. In some embodiments, the spacer is a chemical entity. In some embodiments, the spacer is covalent bond. In some embodiments, the spacer is selected from: a chemical entity, covalent bond, or non-covalent bond a non-covalent bond In some embodiments, the the spacer comprises an amino acid or a derivative thereof.

In some embodiments, the polypeptide conjugate is in an aggregated nano-particulate form wherein, the polypeptide conjugate is aggregated into a crystalline form.

In some embodiments, the polypeptide conjugate further comprising at least one active principle attached to the polypeptide via one or more non-covalent bonds. In some embodiments, the at least one active principle is attached to the polypeptide via physical entrapment.

In some embodiments, the moiety is a liposome or viral capsule. In some embodiments, the moiety is a polymeric nanoparticle or a particulate system selected from inorganic and composite particles. In some embodiments, the moiety is in the form of inorganic particles. In some embodiments, the moiety is in the form of composite particles.

In some embodiments, the moiety comprises at least one active principle selected from an active pharmaceutical ingredient and a diagnostic agent. In some embodiments, the active principle is an active pharmaceutical ingredient. In some embodiments, the active principle is a diagnostic agent.

In some embodiments, the active principle is selected from an active pharmaceutical small molecule, a protein, a nucleic acid, an antisense molecule, an expression conjugate that comprises a nucleic acid that encodes a therapeutic protein of interest, a liposome, nanoparticles, diagnostic agents, markers of a disease of a central nervous system disorder, cancer, diabetes, antibodies, erythrocytes, erythrocyte ghosts, spheroplasts, monoclonal antibodies, labeled monoclonal antibodies which bind a marker of a central nervous system disorder, cancer or diabetes, and/or a fragment of antibody or monoclonal antibody.

In some embodiments, the active principle is an active pharmaceutical small molecule. In some embodiments, the active principle is a protein. In some embodiments, the active principle is a nucleic acid. In some embodiments, the active principle is an antisense molecule. In some embodiments, the active principle is an expression conjugate. In some embodiments, the expression conjugate is a nucleic acid that encodes a therapeutic protein of interest. In some embodiments, the active principle is a liposome. In some embodiments, the active principle is a nanoparticle or nanoparticles. In some embodiments, the active principle is a diagnostic agent. In some embodiments, the active principle is a marker of a disease of a central nervous system disorder. In some embodiments, the active principle is a marker of cancer. In some embodiments, the active principle is a marker of diabetes. In some embodiments, the active principle is an antibody. In some embodiments, the active principle is an erythrocyte, In some embodiments, the active principle is an erythrocyte ghost. In some embodiments, the active principle is a spheroplasts. In some embodiments, the active principle is a monoclonal antibody. In some embodiments, the active principle is a labeled monoclonal antibody. In some embodiments, the active principle is a fragment of an antibody. In some embodiments, the active principle is a fragment of a monoclonal antibody.

In some embodiments, the polypeptide is a derivative that is at least 90% identical to polypeptide sequence (SEQ ID NO. 1). In some embodiments, the moiety is a photo sensitive molecule or particle. In some embodiments, the moiety is attached via a photo sensitive linker to the polypeptide. In some embodiments, the aggregate also includes cysteine and at least one hydrophobic moiety.

In some embodiments, the aggregate has a spherical structure. In some embodiments, the aggregate has a rod-shaped structure. In some embodiments, the active principle is surrounded within the aggregate.

In some embodiments, the polypeptide includes the sequence Gly-Tyr-Arg-Pro-Val-His-Asn-Ile-Arg-Gly-His-Trp-Ala-Pro-Gly-Gly-Gly-Tyr-Arg-Pro-Val-His-Asn-Ile-Arg-Gly-His-Trp-Ala-Pro-Gly (SEQ ID NO. 2). In some embodiments, the immediately aforementioned sequence has an additional cystein residue. In some embodiments, the additional cystein residue is at the C-terminus of the peptide. In some embodiments, the additional cystein residue is at the N-terminus of the peptide. In some embodiments, the additional cystein residue is located somewhere between two existing residues.

In one aspect, a pharmaceutical composition is disclosed, having a polypeptide conjugate as herein described and a pharmaceutically acceptable carrier. In some embodiments, the pharmaceutical composition includes one or more pharmaceutically acceptable excipients. In some embodiments, the pharmaceutical composition is in the form of a solid. In some embodiments, the pharmaceutical composition is in the form of a liquid.

In another aspect, a method for delivering a therapeutic agent is disclosed which includes (a) providing a polypeptide conjugate and (b) contacting a mammalian cell with the polypeptide conjugate. In some embodiments, the method also includes irradiating the polypeptide conjugate.

In some embodiments, the mammalian cell is from a mammalian tissue selected from the gastro-intestinal tract, bone marrow, liver, spleen, brain, kidney, lungs, pancreas, bladder, eye, normal and pathologic blood vessels, and cancer cells. In some embodiments, the mammalian cell is from the gastro-intestinal tract. In some embodiments, the mammalian cell is from the bone marrow. In some embodiments, the mammalian cell is from the, liver. In some embodiments, the mammalian cell is from the spleen. In some embodiments, the mammalian cell is from the brain. In some embodiments, the mammalian cell is from the kidney. In some embodiments, the mammalian cell is from the lungs. In some embodiments, the mammalian cell is from the pancreas. In some embodiments, the mammalian cell is from the bladder. In some embodiments, the mammalian cell is from the eye. In some embodiments, the mammalian cell is from the normal blood vessels. In some embodiments, the mammalian cell is from the pathologic blood vessels. In some embodiments, the mammalian cell is from cancer cells.

In another aspect, a use of a polypeptide conjugate or a composition with a polypeptide conjugate is disclosed for the treatment or prophylaxis of a disorder or diagnosis of a disorder. In some embodiments the use is for the treatment of a disorder. In some embodiments, the use is for the diagnosis of a disorder.

In some embodiments, the disorder is selected from a central nervous system disorders, cancer, and diabetes. In some embodiments, the disorder is a central nervous system disorder. In some embodiments, the disorder is cancer. In some embodiments, the disorder is diabetes.

In some embodiments, the central nervous system disorder is selected from depression, dementia, prion diseases, Alzheimer's disease, Parkinson's disease, multiple sclerosis, amylotrophic lateral sclerosis, and schizophrenia. In some embodiments, the central nervous system disorder is depression. In some embodiments, the central nervous system disorder is dementia. In some embodiments, the central nervous system disorder is prion diseases. In some embodiments, the central nervous system disorder is Alzheimer's disease. In some embodiments, the central nervous system disorder is Parkinson's disease. In some embodiments, the central nervous system disorder is multiple sclerosis. In some embodiments, the central nervous system disorder is amylotrophic lateral sclerosis. In some embodiments, the central nervous system disorder is schizophrenia.

In some embodiments, the disorder is traumatic brain injury. In some embodiments, the disorder is psychosis. In some embodiments, the disorder is Chorea. In some embodiments, the disorder is Huntington disease. In some embodiments, the disorder is encephalopathy. In some embodiments, the disorder is epilepsy. In some embodiments, the disorder is a cerebrovascular disease. In some embodiments, the disorder is a neurodegenerative disorder.

In some embodiments, the disorder is lyme disease. In some embodiments, the disorder is poliomyelitis.

In some embodiments, the disorder is cancer. In some embodiments, the cancer is selected from carcinoma cancer, breast cancer, prostate cancer, lung cancer, pancreatic cancer, colon cancer, sarcoma cancers, bone sarcoma, sarcoma of cartilage, sarcoma of fat tissues, nerve cancer, lymphoma, leukemia, germ cell tumor, seminoma, dysgerminoma, blastoma cancer. In some embodiments, the cancer is carcinoma cancer. In some embodiments, the cancer is breast cancer. In some embodiments, the cancer is prostate cancer. In some embodiments, the cancer is lung cancer. In some embodiments, the cancer is pancreatic cancer. In some embodiments, the cancer is colon cancer. In some embodiments, the cancer is sarcoma cancer. In some embodiments, the cancer is bone sarcoma. In some embodiments, the cancer is sarcoma of cartilage. In some embodiments, the cancer is sarcoma of fat tissues. In some embodiments, the cancer is nerve cancer. In some embodiments, the cancer is lymphoma. In some embodiments, the cancer is leukemia. In some embodiments, the cancer is germ cell tumor. In some embodiments, the cancer is seminoma. In some embodiments, the cancer is dysgerminoma. In some embodiments, the cancer is blastoma cancer.

In some embodiments, the disorder is diabetes. In some embodiments, the disorder is diabetes mellitus. In some embodiments, the disorder is type 1 diabetes. In some embodiments, the disorder is type 2 diabetes. In some embodiments, the disorder isgestational diabetes.

The present invention relates to a polypeptide conjugate for use in a method for binding and/or internalization of the polypeptide conjugate to a mammalian cell having a transferrin receptor (TFRC) and/or receptor for advanced glycation end products (RAGE), the method comprising the steps of a. providing i. a polypeptide conjugate comprising a polypeptide attached to at least one moiety, wherein the polypeptide sequence is Gly-Tyr-Arg-Pro-Val-His-Asn-Ile-Arg-Gly-His-Trp-Ala-Pro-Gly (SEQ ID NO. 1), or a derivative being at least 80% identical to polypeptide sequence (SEQ ID NO. 1), or pharmaceutically acceptable salts or esters thereof and ii. a mammalian cell having a TFRC and/or RAGE, b. allowing interaction of polypeptide conjugate with the mammalian cell having the TFRC and/or RAGE, and c. binding of the conjugate to the TFRC and/or RAGE, and/or internalization of the polypeptide conjugate or a component thereof into the mammalian cell having the TFRC and/or RAGE.

The ability of polypeptide sequence (SEQ ID NO. 1) or derivatives thereof to interact with the TFRC and/or RAGE receptor makes it possible to bind or internalize a conjugate comprising the polypeptide sequence (SEQ ID NO. 1) or derivatives thereof into a mammalian cell having the TFRC and/or RAGE receptor. The moiety associated with the polypeptide sequence (SEQ ID NO. 1) may be biological, chemical or a particulate entity, which may be used either for therapeutic or diagnostic purposes or both. In certain embodiments the moiety is released from the polypeptide to exert a biological effect inside a cell. Alternatively, the moiety may be released outside the cell. Since TFRC and/or RAGE receptors are present only on some cells this will make it possible to target the moieties specifically towards cells that express these receptors.

The polypeptide conjugate provide means for use as a targeting principle in the treatment, prophylaxis and diagnosis of a disorder associated with the central nervous system and/or a malignant tissue bearing cells expressing TFRC and/or RAGE on their plasma membrane. The peptide part of the conjugate plays an important role in the interaction with the TFRC and/or RAGE through formation of salt bridges, electrostatic interactions, hydrogen bonding, van der Waals and/or hydrophobic interactions.

Since the RAGE receptors are expressed on cells lining the blood brain barrier the peptide conjugate is able to cross this barrier. As inferred by real-time single cell imaging these cells take up the polypeptide conjugate (or its other forms thereof) through different modes of internalization processes within minutes to hours after initial binding of the peptide conjugate to the corresponding receptors.

In order for the polypeptide to be able to bind to the TFRC and/or RAGE, preferably, the peptide comprise an amino acid sequence which is at least 12, 13, 14 amino acids identical to the polypeptide corresponding to an 80%, 87% and 93% identity to the polypeptide sequence (SEQ ID NO. 1). In an aspect of the invention the derivative is at least 90% identical to polypeptide sequence (SEQ ID NO. 1). The total number of amino acids of the polypeptide may be higher than the amino acids of sequence (SEQ ID NO. 1) or derivatives thereof, such as 16, 17 or 18 amino acids.

In another aspect of the invention the polypeptide conjugate is in an aggregated form prior to interaction of the polypeptide conjugate with the mammalian cell having the TFRC and/or RAGE, wherein the aggregate is formed of at least two molecules of the polypeptide conjugate. The aggregated form is relatively stable to external conditions so that the conjugate will be less vulnerable to degradation.

Notably, the aggregate may be a particle of at least 2 nm in diameter. The particle may have any suitable physical form or shape, including a fiber form in any aspect ratio. The particles may self-aggregate to conceal the moiety inside a core or surrounded by fibers. The concealing of the moiety inside a particle isolates it from non-target cells. Thus, cells not harbouring TFRC and/or RAGE receptors may remain unaffected and less vulnerability to adverse effects of the moiety. The moieties of the conjugate may be considered the "core" of a particle, whereas the polypeptide in any form may be considered the "shell".

In one embodiment, the peptide conjugates forming core-shell structured nanoparticles with a hydrophobic core comprising the moiety and a hydrophilic peptide shell comprising amino acids from peptide (SEQ ID NO. 1) arranged towards the surroundings. This structure may further fold into a tertiary structure. In a particular embodiment, where the moiety or hydrophobic core is a fluorophore (e.g., FAM) the critical aggregation concentration (CMC) is 2.8 µM. Above the CMC the peptide conjugate can self-assemble and form a network of particles and fibres, that is a mixture of particles and fibres in free form or interconnected particles and fibres. In this particular embodiment, the sizes of particles formed have a hydrodynamic diameter in the range of 70-170 nm at physiological pH as determined by nanoparticle tracking analysis (NTA).

It is contemplated that the at least one moiety of the peptide conjugate may be any drug molecule, biological molecule, a surface-active agent, a hydrophobic molecule or fluorescent molecule or salts thereof. The versatility of the technology makes it possible to design a variety of conjugates which may be used for any medical or non-medical purpose. In the medical field, the invention provides a general method for transporting moieties to cells harbouring TFRC and RAGE. Thus, according to an aspect of the invention, the polypeptide conjugate is provided in aggregated form in a pharmaceutical composition. The pharmaceutical composition may be used for the treatment or prophylaxis of diseases.

Once the polypeptide conjugate has targeted the tissue of interest the pharmaceutical or diagnostic effect can take place due to the binding and/or internalizing properties of the peptide conjugate or a drug molecule carried by the peptide conjugate.

In one embodiment, the polypeptide or derivatives thereof may be coupled by a spacer to one or more polypeptides of the polypeptide (SEQ ID NO. 1), or derivatives thereof. In a particular embodiment the polypeptide (SEQ ID NO. 1) is coupled to another polypeptide (SEQ ID NO. 1), thus forming a dimer formed of the polypeptides. Surprisingly, the present invention further shows a conjugate comprising a dimer of the polypeptide has higher binding and affinity for cells expressing TRFC and/or RAGE. The more binding and/or higher affinity serves to facilitate the transfer of the moiety and thus enhances the binding and/or internalization.

The spacer may be a chemical entity, covalent bonding, or non-covalent bonding. In a specific example the spacer comprises an amino acid residue such as a glycine or serine residue or a derivative thereof or any other chemical structures such as amide bonds.

In another embodiment the polypeptide is attached to at least one moiety via a linker, which may be a chemical entity or a covalent bonding. The presence of the linker makes it possible in a convenient way to produce a variety of different conjugates, which may be used for different purposes, such as different diseases.

The polypeptide (SEQ ID NO. 1) may be coupled directly to the moiety with a covalent bond or the linker may comprise a sulphur-containing amino acid residue such as cysteine or methionine, or a derivative thereof. When a sulphur-containing amino acid residue is used it makes it possible to couple two components to the same polypeptide. The two components include at least one moiety as used herein, however both components may be moieties thereby doubling the effect. The other component may be different active compounds, markers, fluorescent molecules, etc. specifically, one of the components may be a liposome.

An active principle is defined as a constituent of a drug on which the characteristic therapeutic action of the substance largely depends. The active principle is selected from a group of active pharmaceutical small molecules, proteins, nucleic acids including siRNA molecules and antisense molecules, expression conjugates that comprise a nucleic acid that encodes a therapeutic protein of interest, liposomes, nanoparticles, diagnostic agents, markers of a disease of central nervous system disorder, cancer or diabetes, antibodies, erythrocytes, erythrocyte ghosts, spheroplasts, monoclonal antibodies, labeled monoclonal antibodies which bind a marker of a central nervous system disorder, cancer or diabetes, and/or a fragment of an antibody or a monoclonal antibody. In a certain embodiment, the moiety of the polypeptide conjugate is attached to the polypeptide via one or more non-covalent bonding(s). The non-covalent bonding includes the physical entrapment or encasement of an active principle. The moiety of the polypeptide conjugate may be any conventional case such as a viral capsule, liposome, etc. which has entrapped an active principle.

In one embodiment of the polypeptide conjugate the moiety is a liposome. The liposome is contemplated to comprise an active principle or a diagnostic agent, and transport it in circulation of the body to the target cell.

In another embodiment the moiety may be a polymeric nanoparticle, such as nanoparticles prepared from polymers with the ability to dissolve, entrap, encapsulate or attach to an active principal, or any other particulate system including an inorganic and composite particle such as metallic particles, for example gold, silver, cadmium, selenide or silicon or combinations thereof.

In a preferred embodiment the polypeptide conjugate may target the gastro-intestinal tract, bone marrow, liver, spleen, brain, kidney, lungs, pancreas, bladder, eye, normal and pathologic blood vessels and/or cancer cells.

It is contemplated that the polypeptide conjugate may be administered as a solid composition to a patient in need thereof for example in a tablet or capsule form. It is also contemplated that the polypeptide conjugate may be administered as a solution/suspension composition to a patient in need thereof.

In a particular embodiment the moiety is a photo sensitive molecule or particle. Photosensitive molecules or particles attached to the polypeptide conjugate are able to target cells and thus may be used as functional, therapeutic and/or diagnostic tools. Photosensitive molecules may comprise fluorophores such as cyanine or derivatives thereof, preferably Cy3 or Cy5, fluorescein amidite (FAM), or rhodamine.

In a more particular embodiment the moiety is attached via a photosensitive linker to the polypeptide allowing the liberation of polypeptide conjugate components upon exposure to irradiation. The polypeptide conjugate in the cell may be exposed to irradiation with wavelengths in the range of 400-800 nm for a specific time (e.g., up to 10 min) activating the photosensitive bonding, thereby liberating the moiety. The chosen wavelength depends on the choice of the fluorophor and is within skill of the art. The photo sensitive linker may be a disulphide-bridge coupled to cyanine by a covalent bonding in a Cy3-siRNA:FAM-polypeptide complex. When irradiated with light having a wavelength of 488 nm the Cy3-siRNA dissociates from the FAM-labeled polypeptide. Other photosensitive linkers may be biotin, 2-nitrobenzyl, phenacyl esters or the like.

In another aspect of the invention the polypeptide conjugate comprises a polypeptide linked through a linker to a hydrophobic moiety, wherein the polypeptide sequence is Gly-Tyr-Arg-Pro-Val-His-Asn-Ile-Arg-Gly-His-Trp-Ala-Pro-Gly (SEQ ID NO. 1), or a derivative being at least 80% identical to polypeptide sequence (1), or pharmaceutically acceptable salts or esters thereof, in aggregated nano-particulate form wherein, the polypeptide conjugate is aggregated into a crystalline form.

In yet another aspect of the invention the polypeptide conjugate comprises a polypeptide linked through a linker to a hydrophobic moiety, wherein the polypeptide sequence is Gly-Tyr-Arg-Pro-Val-His-Asn-Ile-Arg-Gly-His-Trp-Ala-Pro-Gly (SEQ ID NO. 1), or a derivative being at least 80% identical to polypeptide sequence (SEQ ID NO. 1), coupled by a spacer to one or more polypeptide sequence(s) (SEQ ID NO. 1) or derivative(s) thereof at least 80% identical to polypeptide sequence (SEQ ID NO. 1), or pharmaceutically acceptable salts or esters thereof.

In a further embodiment, the polypeptide conjugate may be used for the treatment or prophylaxis of a disorder, wherein the disorder may be selected from but not limited to the groups consisting of central nervous system disorder, cancer, diabetes, cardiovascular, inflammatory or diagnosis as well as cosmetic conditions such as wrinkles, allergies or any other skin problem. The polypeptide conjugate may be used as a diagnostic tool to diagnose central nervous system disorder, cancer, or diabetes disorders or any other disorder.

The central nervous system disorder may be selected from the group consisting of depression, dementia, prion diseases, Alzheimer's disease, Parkinson's disease, multiple sclerosis, amylotrophic lateral sclerosis, schizophrenia, lyme disease, poliomyelitis, traumatic brain injury, psychosis, chorea, Huntington disease, encephalopathy, epilepsy, cerebrovascular diseases, neurodegenerative disorders and central nervous system cancer, the cancer may be selected from carcinoma cancer, i.e. breast, prostate, lung, pancreas, and colon cancer, sarcoma cancer, i.e. bone, cartilage, fat and nerve cancer, lymphoma cancer and leukemia, germ cell tumor i.e. seminoma or dysgerminoma cancer, blastoma cancer, the diabetes i.e. diabetes mellitus may be selected from type 1, type 2, gestational diabetes.

It is contemplated that the polypeptide conjugate may be used in a pharmaceutical composition where the pharmaceutical composition comprises the peptide conjugate and one or more pharmaceutically acceptable excipients.

Definitions

As used herein, the term "polypeptide conjugate" is to be understood as a polypeptide of the invention which is linked to a moiety (the term "moiety" is to be understood as defined herein) and which bind to TFRC and/or RAGE in vitro and/or in vivo.

As used herein, the term "moiety" refers to one or two or more part(s) of a polypeptide conjugate (the term "polypeptide conjugate" is to be understood as defined herein) into which something may be separated from the polypeptide part of the polypeptide conjugate such as, but not limited to, an amino acid, a nucleic acid, a liposome and/or photo sensitive molecule.

As used herein, the term "transferrin receptor" (TFRC) refers to a membrane glycoprotein known to mediate cellular uptake of iron from a plasma glycoprotein, transferrin. Iron uptake from transferrin involves the binding of transferrin to the TFRC and internalization of transferrin within an endocytic vesicle by receptor-mediated endocytosis. The iron is released from the protein by a decrease in endosomal pH. With the exception of highly differentiated cells, TFRCs may be expressed on all cells but their levels vary greatly. TFRCs are highly expressed on immature erythroid cells, placental tissue, and rapidly dividing cells, both normal and malignant (Ponka P and Nam C: The transferrin receptor: role in health and disease: 1999, 31:1111-1137). The term "transferrin receptor" may also refer to a fusion protein of the transferring receptor.

As used herein, the term "receptor for advanced glycation end products" (RAGE) refers to a member of the immunoglobulin super-family, encoded in the Class III region of the major histocompatability complex. Receptor for advanced glycation end product is highly expressed only in the lung at readily measurable levels but increases quickly at sites of inflammation, largely on inflammatory and epithelial cells. It is found either as a membrane-bound or soluble protein that is markedly up-regulated by stress in the endothelium, smooth muscle cells, cardiac myocytes, neural tissue (including CNS and brain), and mononuclear cells thereby regulating their metabolism and enhancing their central barrier functionality (Louis J et al: RAGE (Receptor for Advanced Glycation End products), RAGE Ligands, and their role in Cancer and Inflammation, Journal of Translational Medicine 2009, 7:17 and P. Alexiou et al: A Multi-Ligand Receptor Unveiling Novel Insights in Health and Disease, Current Medicinal Chemistry 2010, 17: 2232-2252) The term "receptor for advanced glycation end products" may also refer to a fusion protein of the receptor for advanced glycation end products.

As used herein, the term "polypeptide" means a compound that consists of amino acids that are linked by means of peptide bonds e.g. covalent amide linkage formed by loss of a molecule of water between the carboxyl group of one amino acid and the amino group of a second amino acid.

As used herein, the term "nanoparticle" means a particle with a diameter between 0.1 and 1000 nm, e.g. liposomes, polymer micelles, polymer-DNA complexes, nanospheres, nanofibres. All these nanoparticles are known in the art. The surface of such nanoparticles is often modified by PEGylation, i.e. polyethylene glycol (PEG) is attached to the surface of the nanoparticles.

As used herein, the term "identical" or "identity" means, that an alignment of two sequences within a stretch of a defined number of amino acids (in the present invention: 15 amino acids) comprises the indicated number of identical amino acids, i.e. the term "identical" or "identity" is as equal to the number of exact matches in an alignment of an amino acid sequence of the present invention and a different amino acid sequence or length. An exact match occurs when the amino acid sequence have identical amino acid residues in the same position overlap. In one embodiment the identity can be expressed in percentage by dividing the number of exact matches by length of the shorter of the two amino acids sequences and convert the result into percentage.

As used herein, the term "mammalian cell" includes in vitro cells, including cultured cells, and/or in vivo cells from animals of economic importance such as bovine, ovine, and porcine animals, especially those that produce meat, as well as domestic animals, sports animal, zoo animals and humans, the latter being preferred.

The term "pharmaceutical composition" encompasses a product comprising an optional carrier comprising inert ingredients.

As used herein, the term "pharmaceutically acceptable" refers to physiologically well tolerated by a mammal or human.

As used herein, the term "spacer" for example a peptide bond or an amino acid, a linker peptide between at least two polypeptide sequences of polypeptide (SEQ ID NO. 1).

As used herein, the term "linker" mean a structure that links a peptide according to the invention and a pharmaceutically acceptable substance (the term pharmaceutically acceptable substance" is to be understood as defined herein) by covalent or non-covalent bonds. The term "linking" includes, but is not limited to: a linker peptide, a carbohydrogen bond, streptavidin-biotin, polyethylene glycol (PEG), a disulfide bridge, and/or metal coordinated linker.

As used herein, the term "liposome" includes any structure composed of a lipid bilayer that encloses one or more volumes, wherein the volume can be an aqueous compartment. Liposome consists of one or more lipid bilayers including but not limited to phospholipid bilayer or bilayer of nonionic surfactant. Liposomes consisting of a phospholipid bilayer may comprise naturally-derived phospholipids with mixed lipid chains (like e.g. phosphatidylethanolamine) but are not limited to these components. Liposomes include, but are not limited to, emulsions, foams, micelles, exosomes, vesicles, insoluble monolayers, liquid crystals, phospholipids dispersions, lamellar layers and the like. The term "liposome" also includes so called "stealth liposomes"

which consist of water-soluble polymers (e.g. polyethylenglycol, PEG) attached to the surface of conventional liposomes composed of a lipid mono- or bilayer that enclose a volume (e.g. so called PEGylated liposomes).

Following liposome preparation, the liposome may be sized to achieve a desired size range and relatively narrow distribution of liposome sizes. For example delivery to the brain, the liposomes should preferably be less than about 1.0 µm in diameter, more preferably 75-400 nm, more preferably 100-200 nm, which allows the liposome suspension to be sterilized by filtration. Methods of coupling peptides to liposomes according to the present invention may involve either covalent cross-linking between a liposomal lipid and a peptide.

BRIEF DESCRIPTION OF DRAWINGS

Live-cell fluorescence microscopy of hCMEC/DE3 cells uptake of different variations of FAM-labeled CGY-peptides. FIG. 7A. 10 µM 5'-FAM (negative control), FIG. 7B. 5 µM 5' labeled CGY-peptide (FAM-CGY), FIG. 7C. 5 µM 3' labeled CGY-peptide (CGY-FAM), FIG. 7D. 5 µM FAM-d-CGY, FIG. 7E. 5 µM FAM-CGY scrambled 1, FIG. 7F. 5 µM FAM-CGY scrambled 2. The hCMEC/DE3 cells were incubated with different variations of FAM-labeled CGY-peptides for 24 h, and washed 3 times with PBS. The nucleus was stained with Hoechst 33342 (5 µg/mL), insert bars=50 µm.

Dose and time-depended vesicular uptake of FAM-CGY peptide in hCMC/DE3 cells. Cells were treated with various concentrations of FAM-CGY peptide ranging from 0-20 µM and stained with Hoechst 33342.

Influence of various endocytic inhibitors on the hCMEC/D3 cells uptake of FAM-CGY peptidic nanoparticles.

FIG. 16A shows a downregulated TFRC expression after using a commercial transfection reagent siPORT Amine/TFRC siRNA complex for 72 h in hCMEC/D3 cells and a unspecific siRNA (siControl) as a positive control. FIG. 16B shows blockage of FAM-CGY nanoparticle uptake in TFRC knocked down hCMEC/D3 cells. The cells with low TFRC expression and siControl transfection cells were incubated with 5 µM FAM-CGY nanoparticles and 62.5 nM transferrin (positive control) for 16 h, respectively, the FAM-CGY nanoparticles and transferrin uptake were detected by fluorescence microscopy (not shown) and b. quantified by FACS. Cell nucleus stained with Hoechest 33342, Insert bars=50 µm.

FIGS. 17A through 17G show FAM-CGY nanoparticles competed with different concentrations of RAGE receptor substrate or amyloid-β peptide. FIGS. 17A through 17G were analyzed by fluorescence microscopy.

FIG. 19A was analyzed by fluorescence microscopy and FIGS. 19B and 19C were quantified by FACS.

FIG. 22A NTA of siRNA/FAM-CGY complexes. FIG. 22B. Size distribution of siRNA/FAM-CGY complexes measured of NTA.

Transfection efficiency studies of siRNA/FAM-CGY complexes.

Figure 26A:
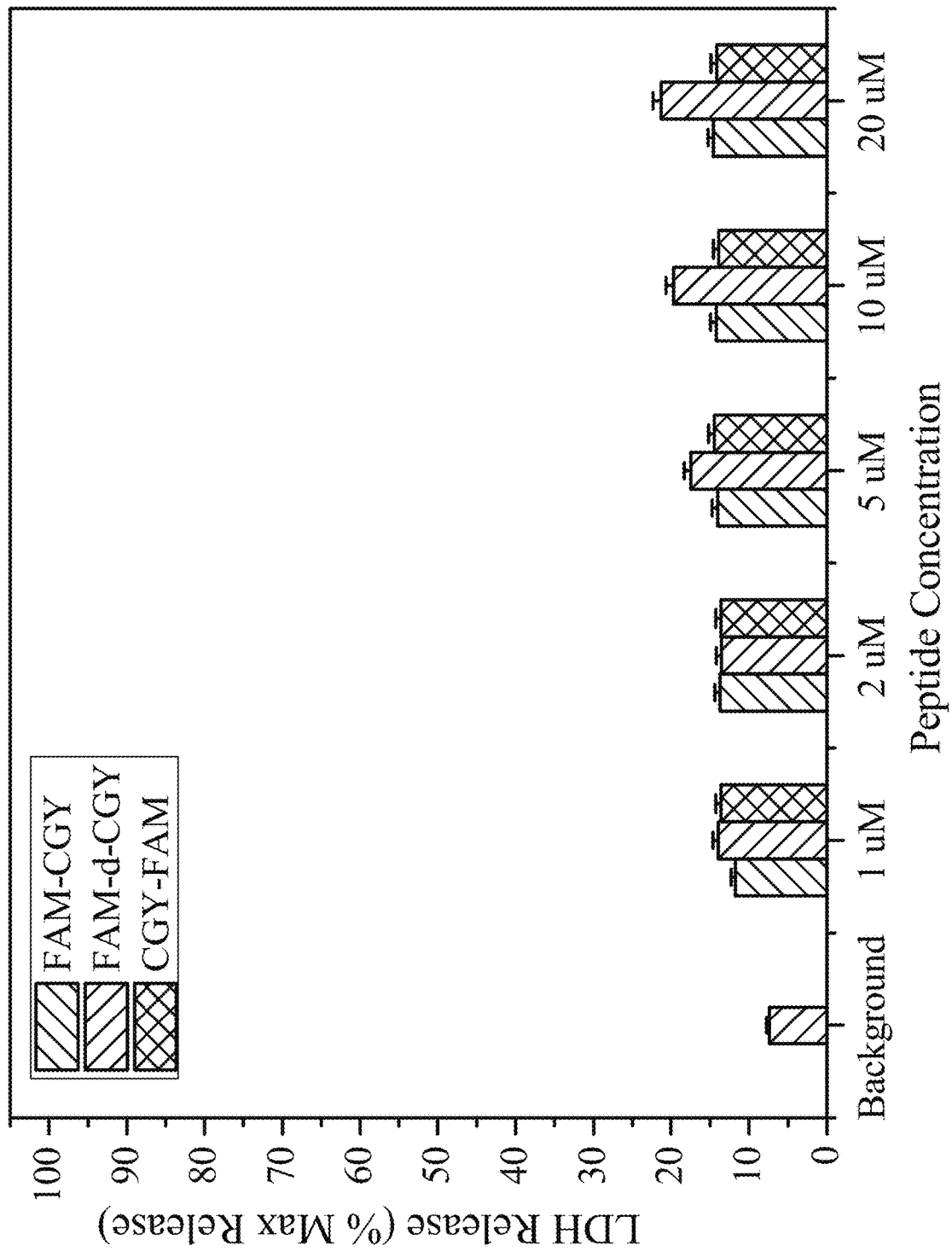

Cell viability assessment following treatment of cells with the fluorescent peptide FIG. 26A or siRNA/FAM-CGY complex FIG. 26B for 24 h, determined by LDH assay (n=6). Background: untreated cells. To examine the cytotoxicity of the peptide and the siRNA/FAM-CGY complex, the hCMEC/D3 cells were incubated with concentrations 1, 2, 5, 10, 20 µM of the peptide and different relations of siRNA/FAM-CGY complexes (8:5, 16:5 or 24:5) for 24 h, the viability of cells without treatment was used as a control. The cytotoxicity was measured by a LDH assay. The LDH assay measures the membrane integrity as a function of the amount of cytoplasmic LDH leaked into the medium.

Figure 8:
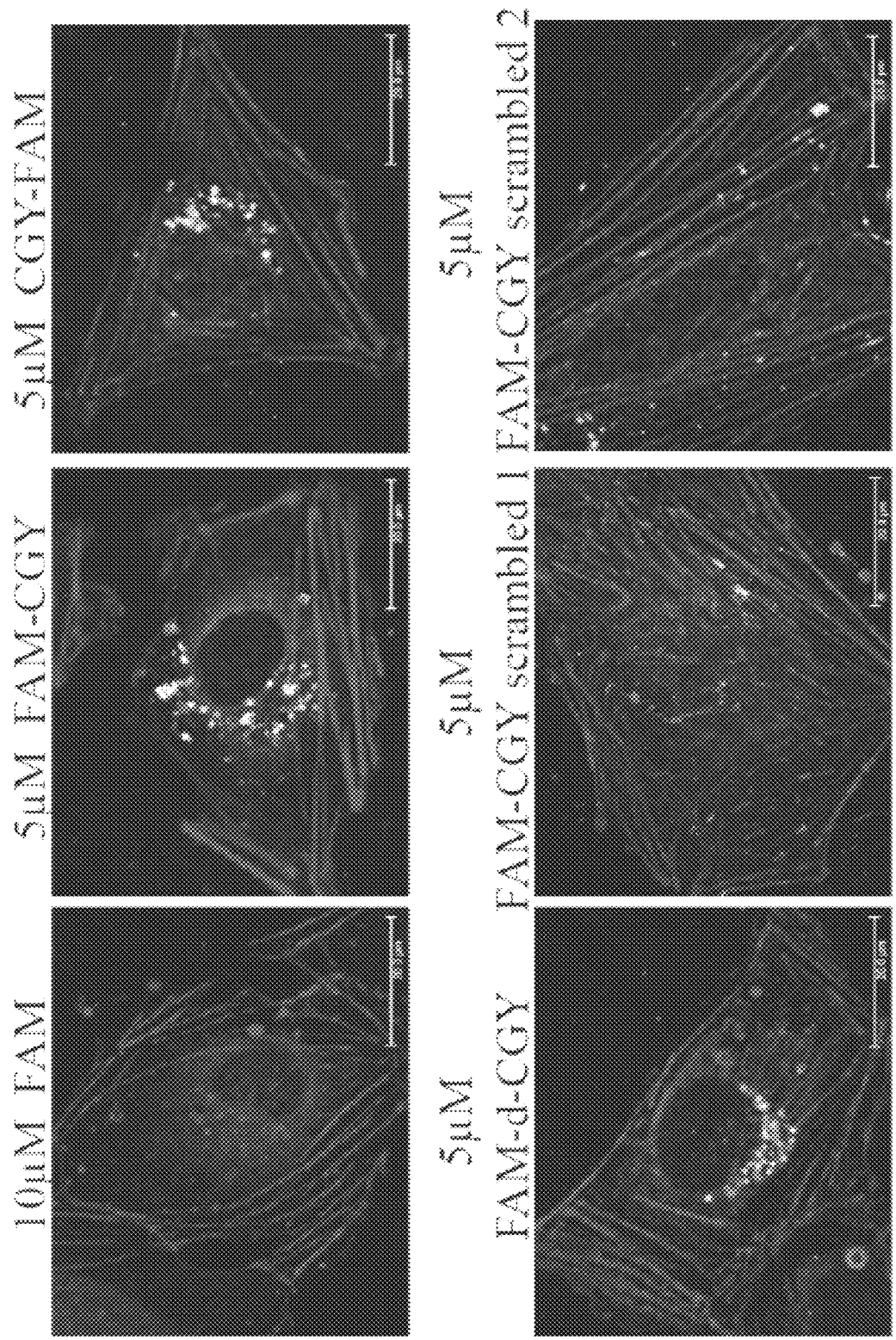
FIG. 8 Single- and live-cell fluorescence microscopy showing hCMEC/DE3 cells uptake of different variations of FAM-labeled CGY-peptides. The cells were stained with CellLight® Actin-RFP and Hoechst 33342. Insert bars=20 µm.
Figure 9:
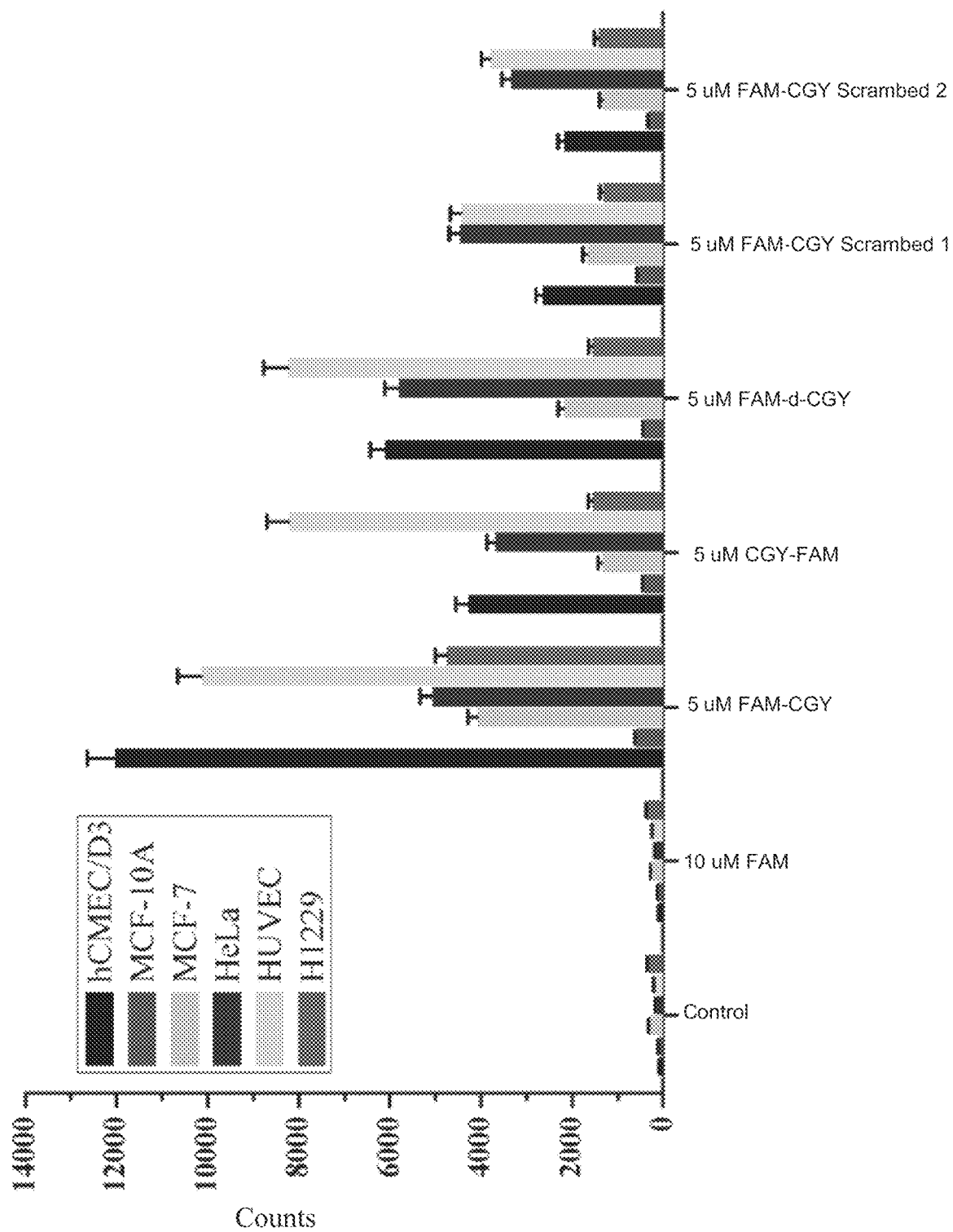
FIG. 9 Quantification of FAM labeled CGY-peptide uptake in different cell lines by fluorescence-activated cell sorting (FACS). The cells were incubated with 5 µM of different variations of FAM-labeled CGY-peptides at 37° C. for 24 h.
Figure 10A:
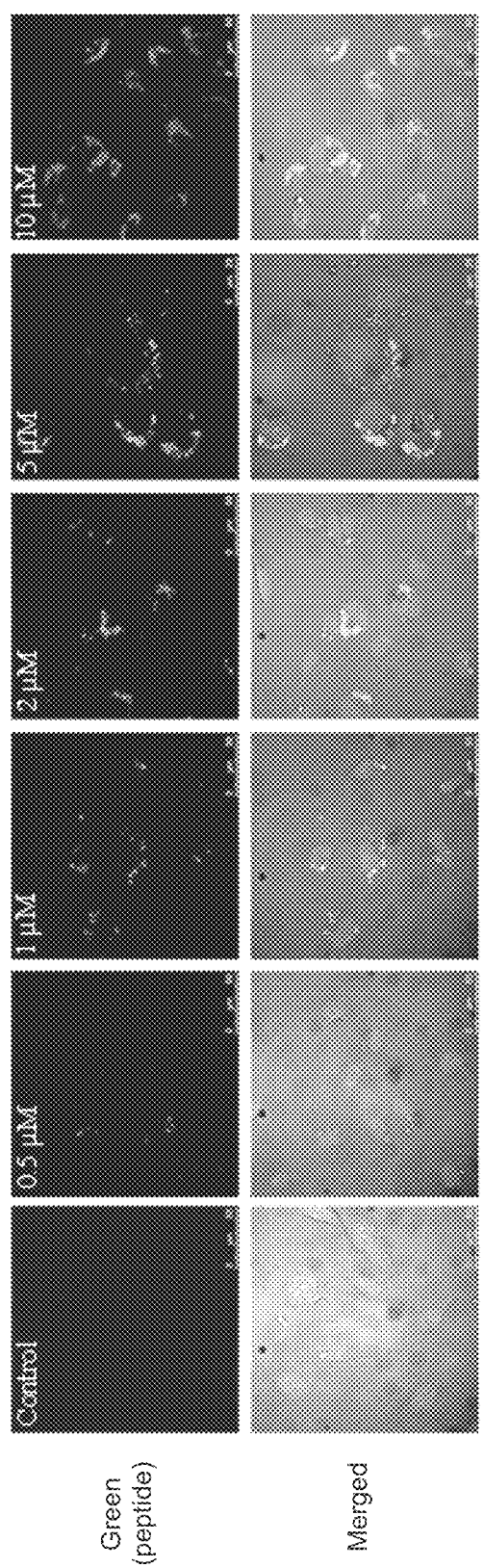
FIG. 10A. Fluorescence microscopy after 24 h.
Figure 10B:
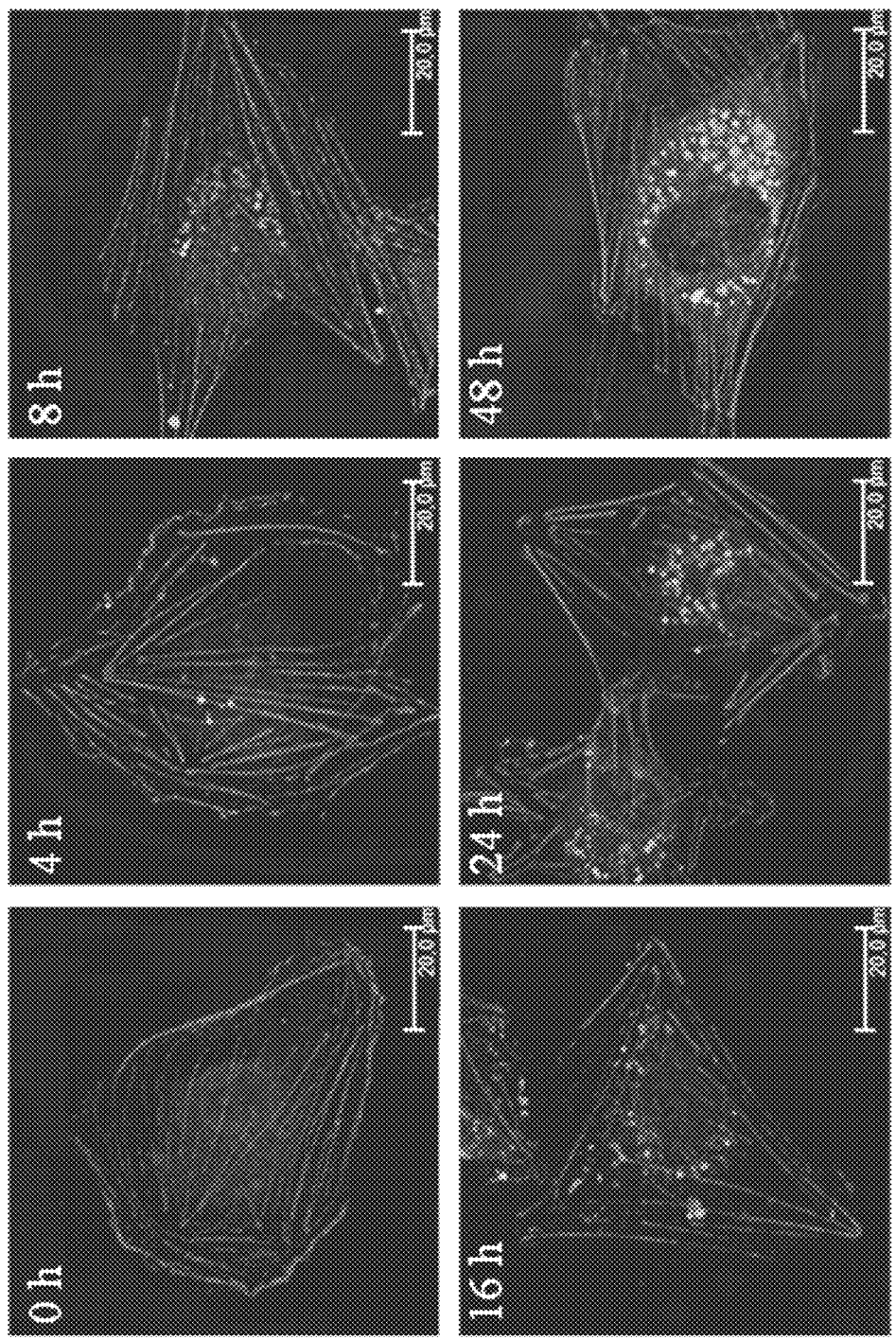
FIG. 10B. hCMC/D3 cells were subjected to 5 µM FAM-CGY nanoparticles and studied with fluorescence microscopy at different time-intervals from 0-48 hours.
Figure 10C:
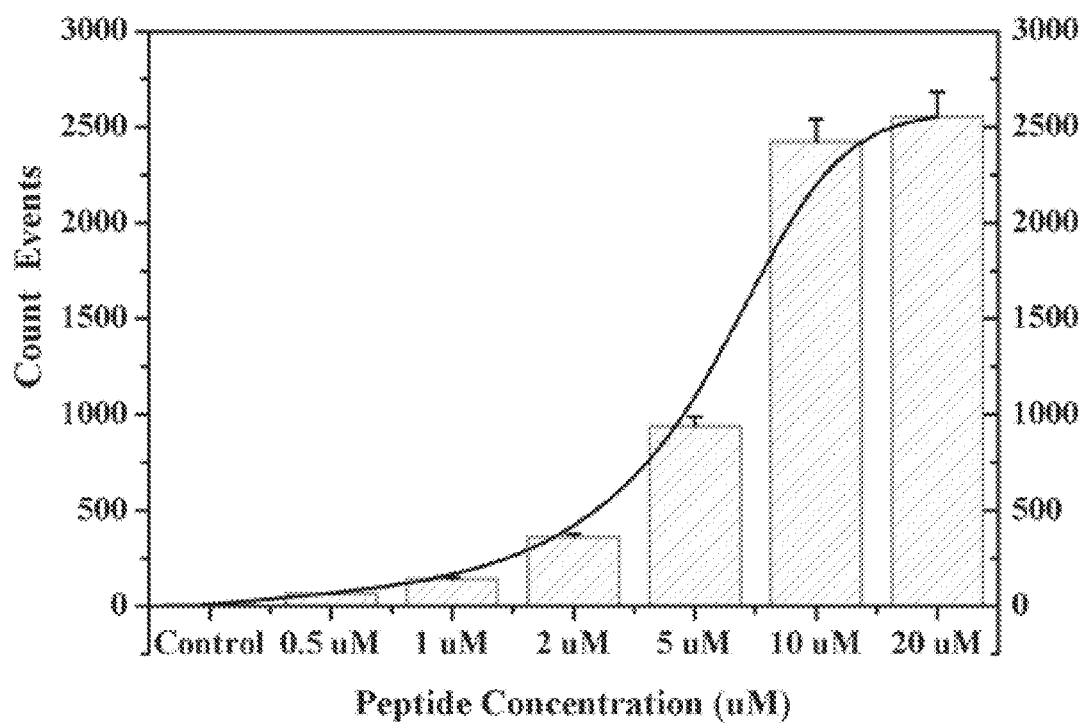
FIG. 10C. Quantification of peptide uptake from (a) by FACS, and FIG. 10D. quantification of uptake from (c) by FACS. The cells were stained with CellLight® Actin-RFP and Hoechst 33342, Insert bars=20 µm.
Figure 10D:
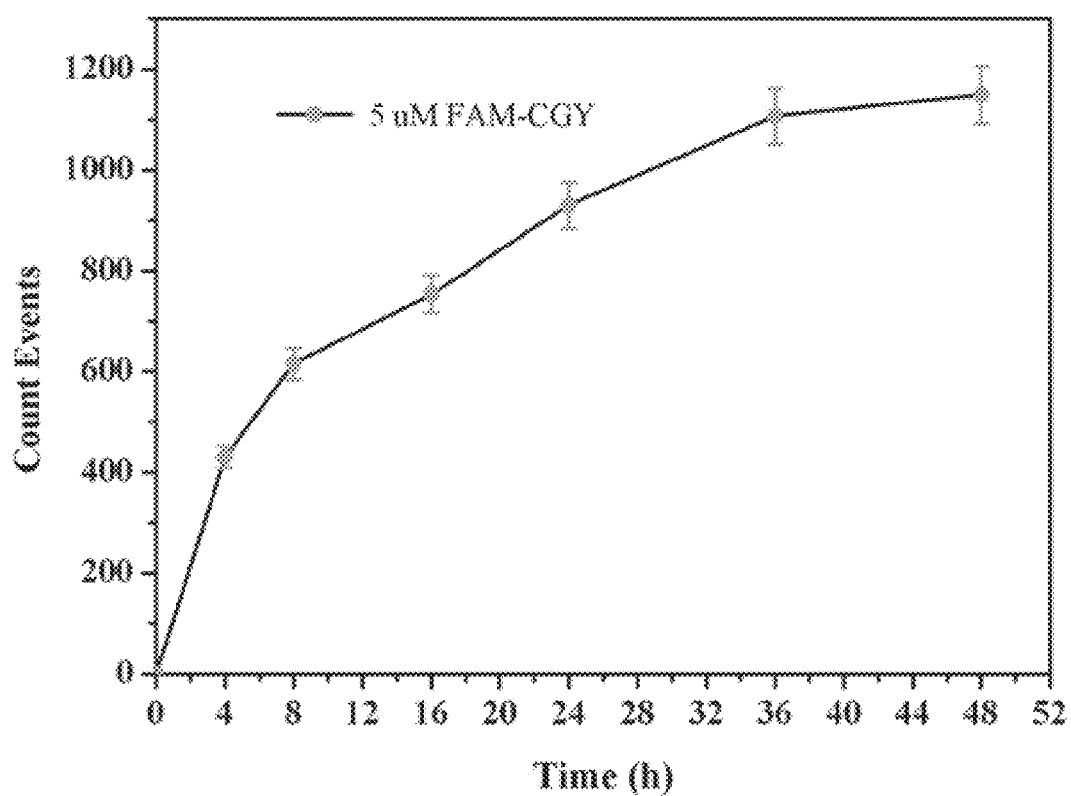
Figure 11A:
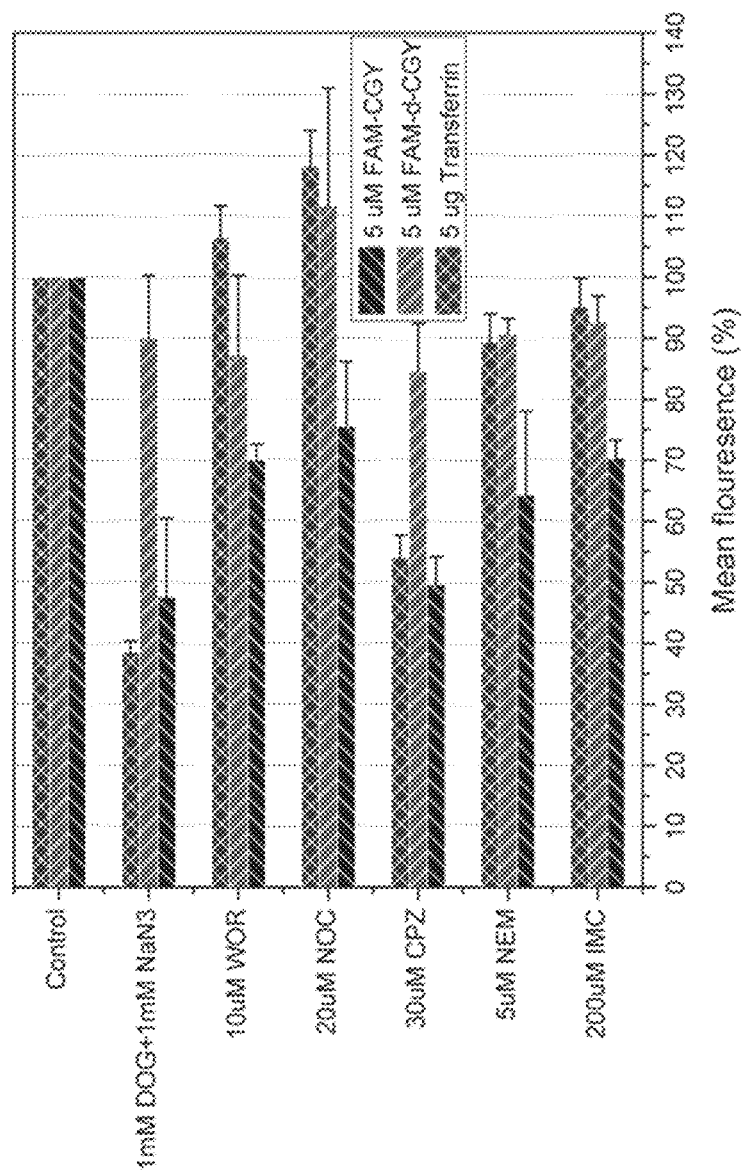
FIG. 11A. FACS analysis of hCMEC/D3 cells incubated with FAM-CGY peptidic nanoparticles or transferrin in the presence different inhibitors. The graph displays mean fluorescence intensities of one of three independent experiments performed in duplicate. The FAM-d-CGY and transferrin were also chosen as controls to perform the inhibition experiments.
Figure 11B:
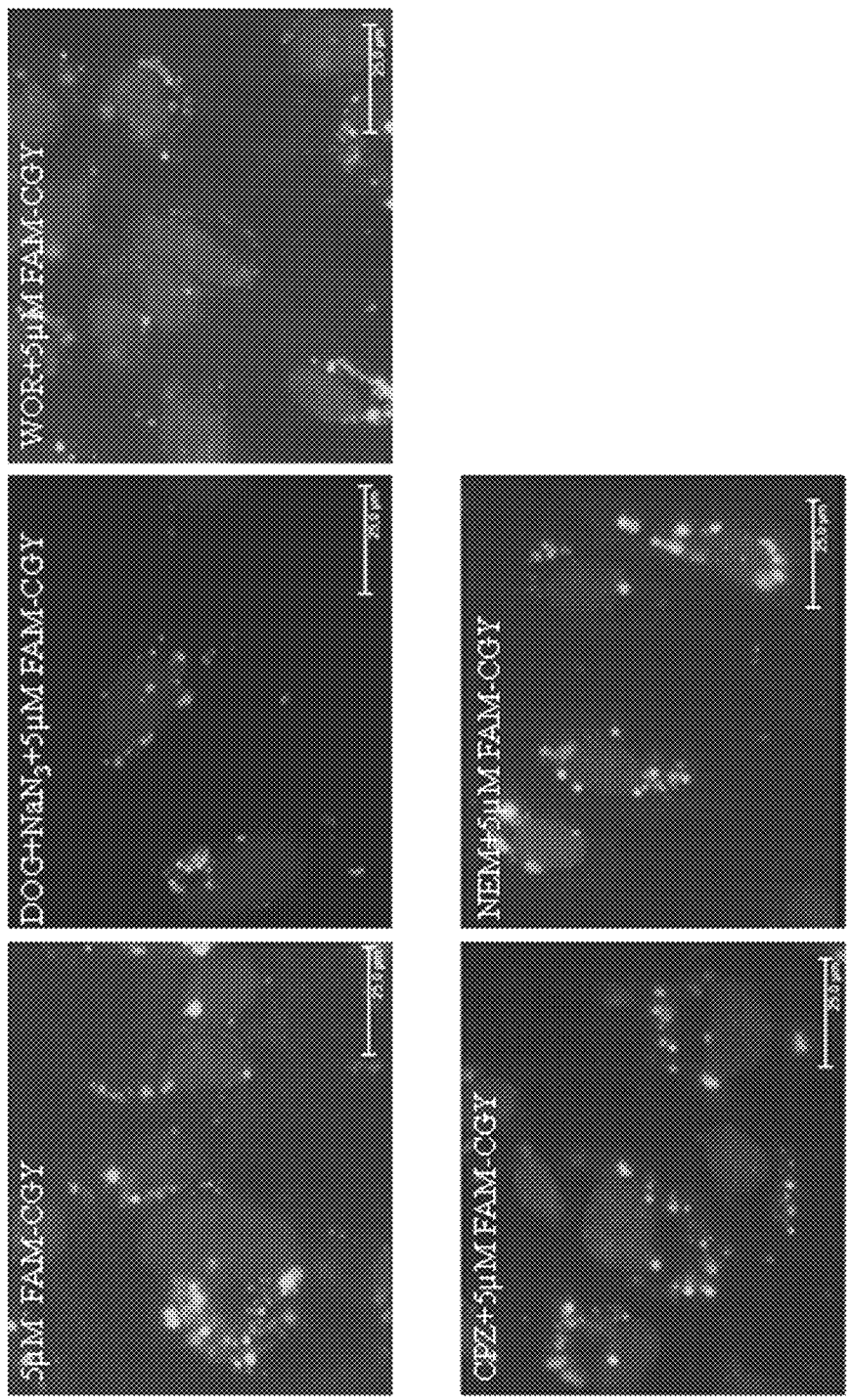
FIG. 11B. Shows the influence of morphology on the hCMEC/D3 cell uptake of FAM-CGY peptidic nanoparticles in presence of various inhibitors by fluorescence microscopy. Energy dependent inhibitor: 1 mM 2-deoxy-D-glucose (DOG) and 1 mM NaN3. Macropinocytosis inhibitor: 10 µM worthmanin (WOR). Fluid phase endocytosis inhibitor: 20 µM nocodazole (NOC). Clathrin-dependent inhibitor: 30 µM chlorpromazine (CPZ). Caveolae-medicated inhibitor: 5 µM N-ethylmaleimide (NEM). Caveolae-dependent endocytosis: 200 µM indomethacin (IMC). Cell nucleus were stained with Hoechst 33342, insert bars=25 µm.
Figure 12A:
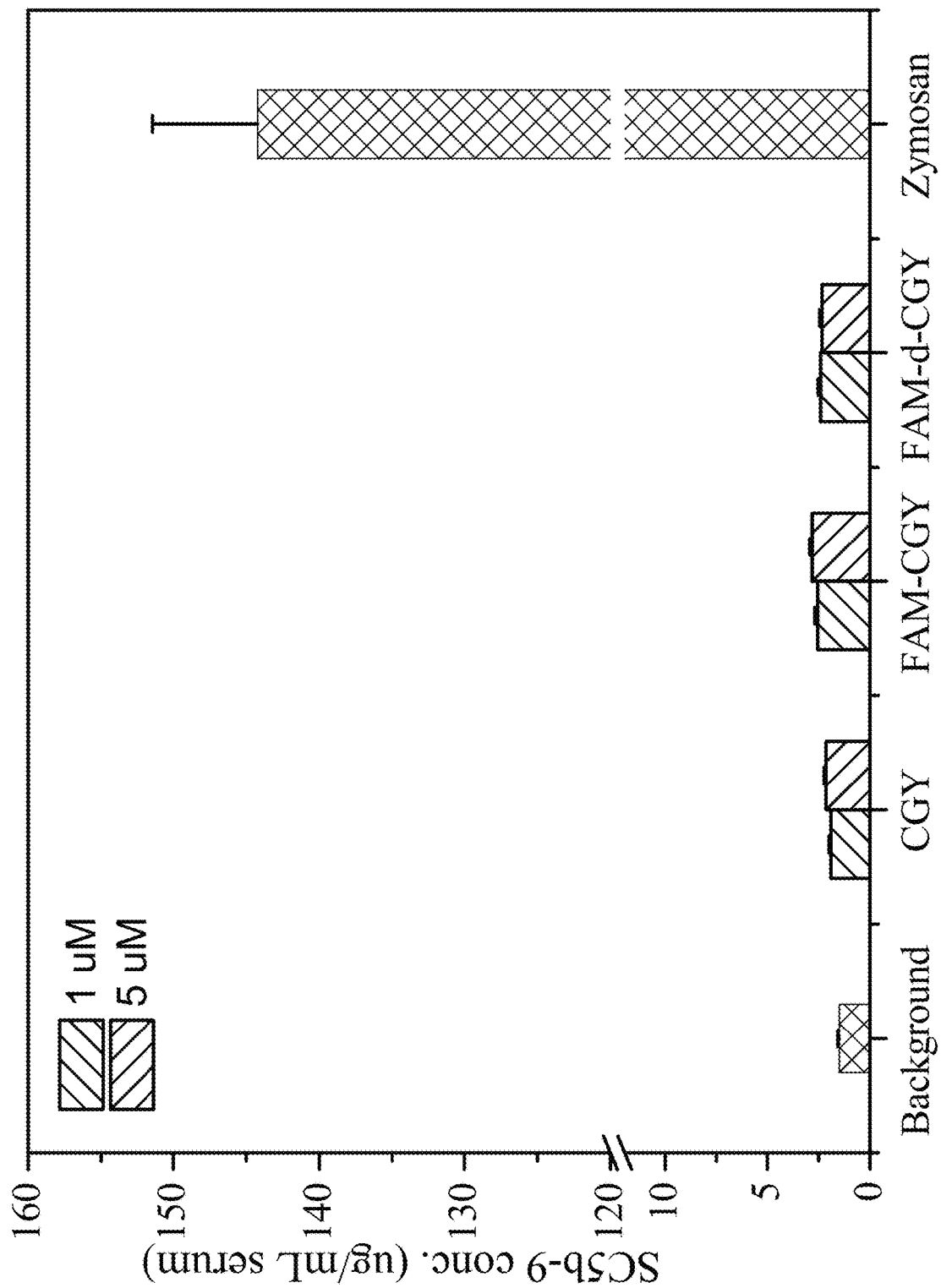
FIGS. 12A, 12B, and 12C are graphs illustrating a complement activation experiment. The complement activation products FIG. 12A. SC5d-9, FIG. 12B. C5a, and FIG. 12C. C3a were quantified in healthy human serum after incubation of CGY, FAM-CGY and FAM-d-CGY peptide at low and high concentration. Background noise and positive control (Zymosan) are presented for each product. Complement activation and fixation is a fundamental process contributing to macrophage clearance of intravenously injected nanopaticles. Accordingly, complement activation studies in human serum were performed with low and high concentrations of FAM-CGY peptide and other peptides (CGY, FAM-d-CGY) for comparison. The FAM-CGY nanoparticles had no significant effect on the level of complement activation products SC5d-9, C5a, and C3a. The responses were relatively low, and close to the background activation. Only a slight level of complement activation was observed compared to the positive control (Zymosan). There were no systematic differences between the activation below and above CMC. Conclusion: The FAM-CGY nanoparticles are unlikely to induce complement-mediated immune reactions following intravenous injection.
Figure 12B:
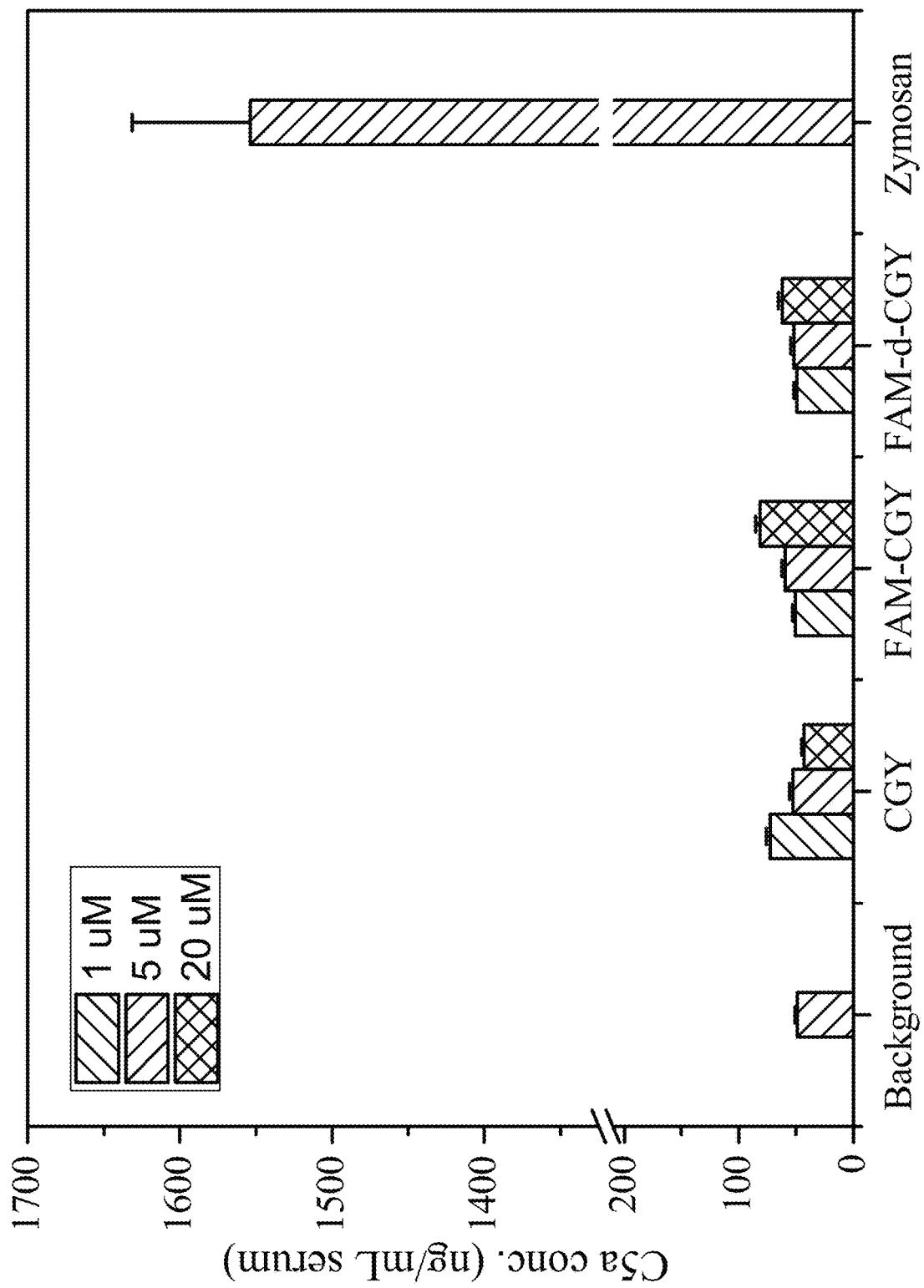
Figure 12C:
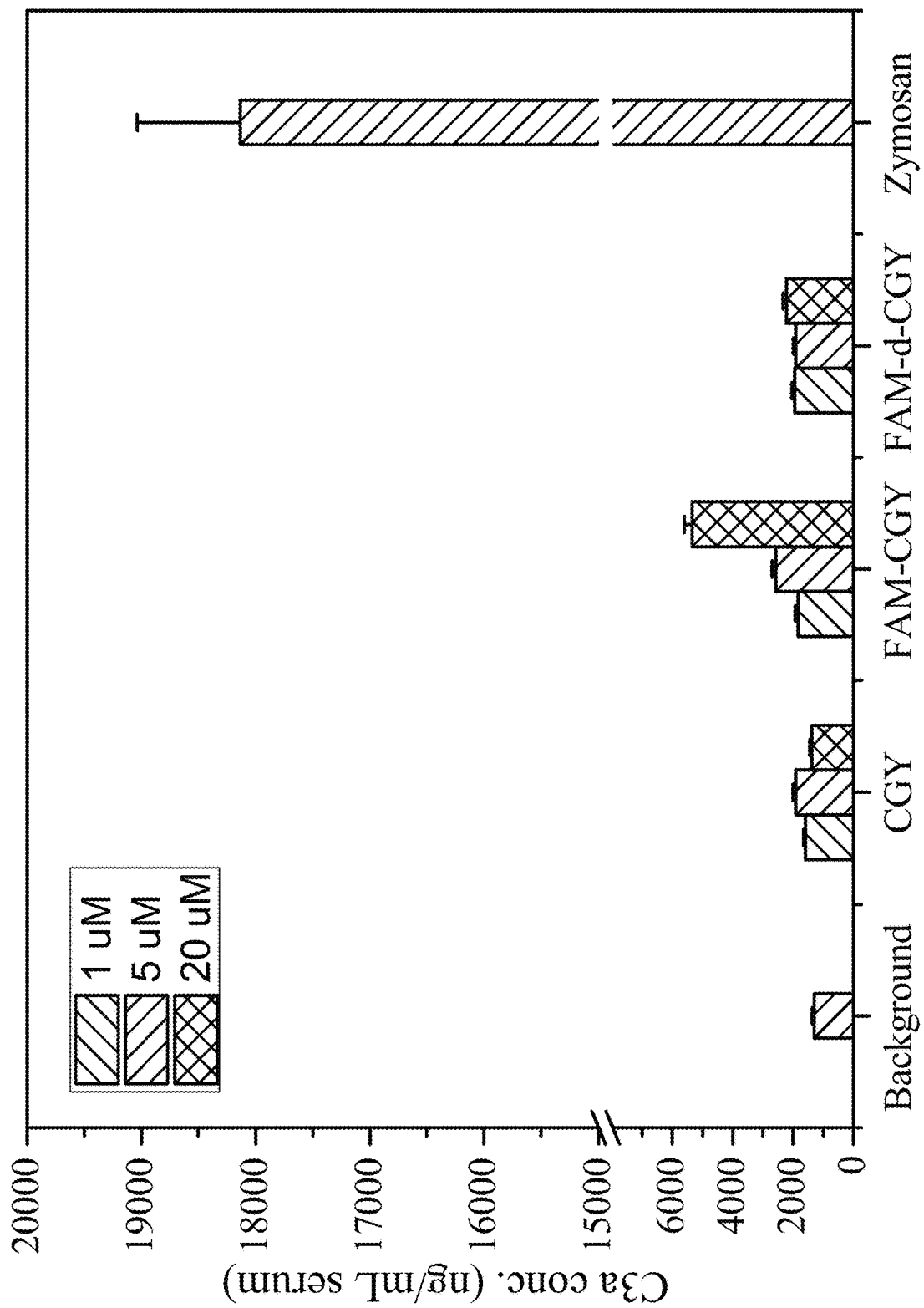
Figure 13:
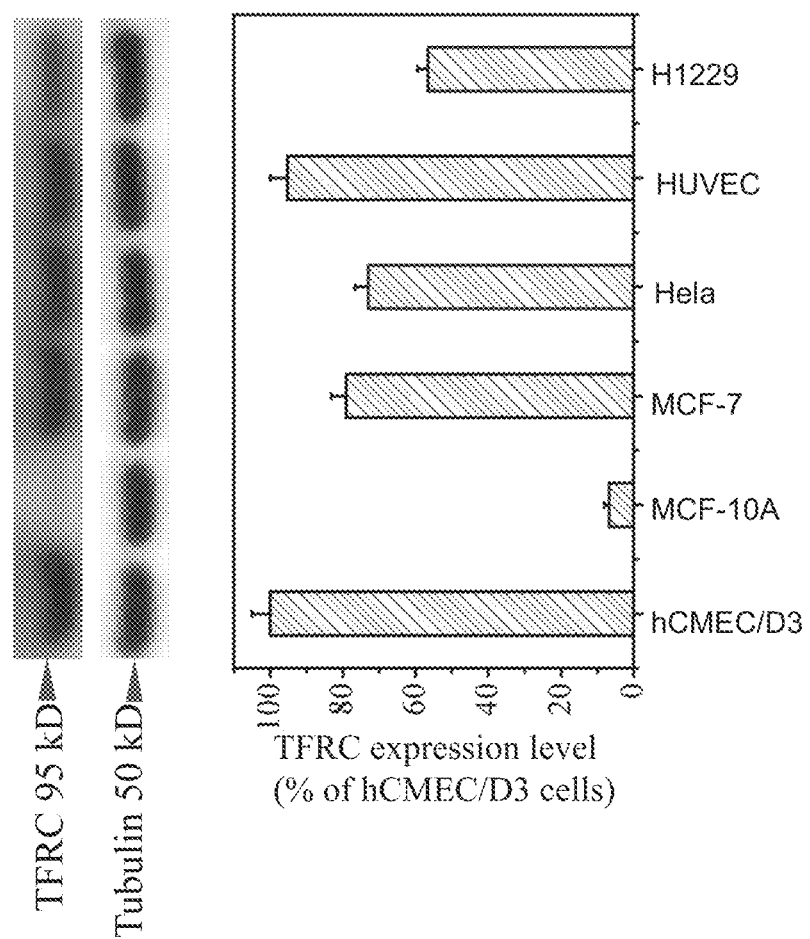
FIG. 13 is a Western blot and chart showing the quantification of the TFRC expression in different cell lines: human brain endothelial cell line (hCMEC/D3), human mammary Epithelial Cell Line (MCF-10A), human breast cancer cell line (MCF-7), human epithelial carcinoma cell line (HeLa), human umbilical vein endothelial cells (HUVEC) and human lung carcinoma cells (H1229).
Figure 14:
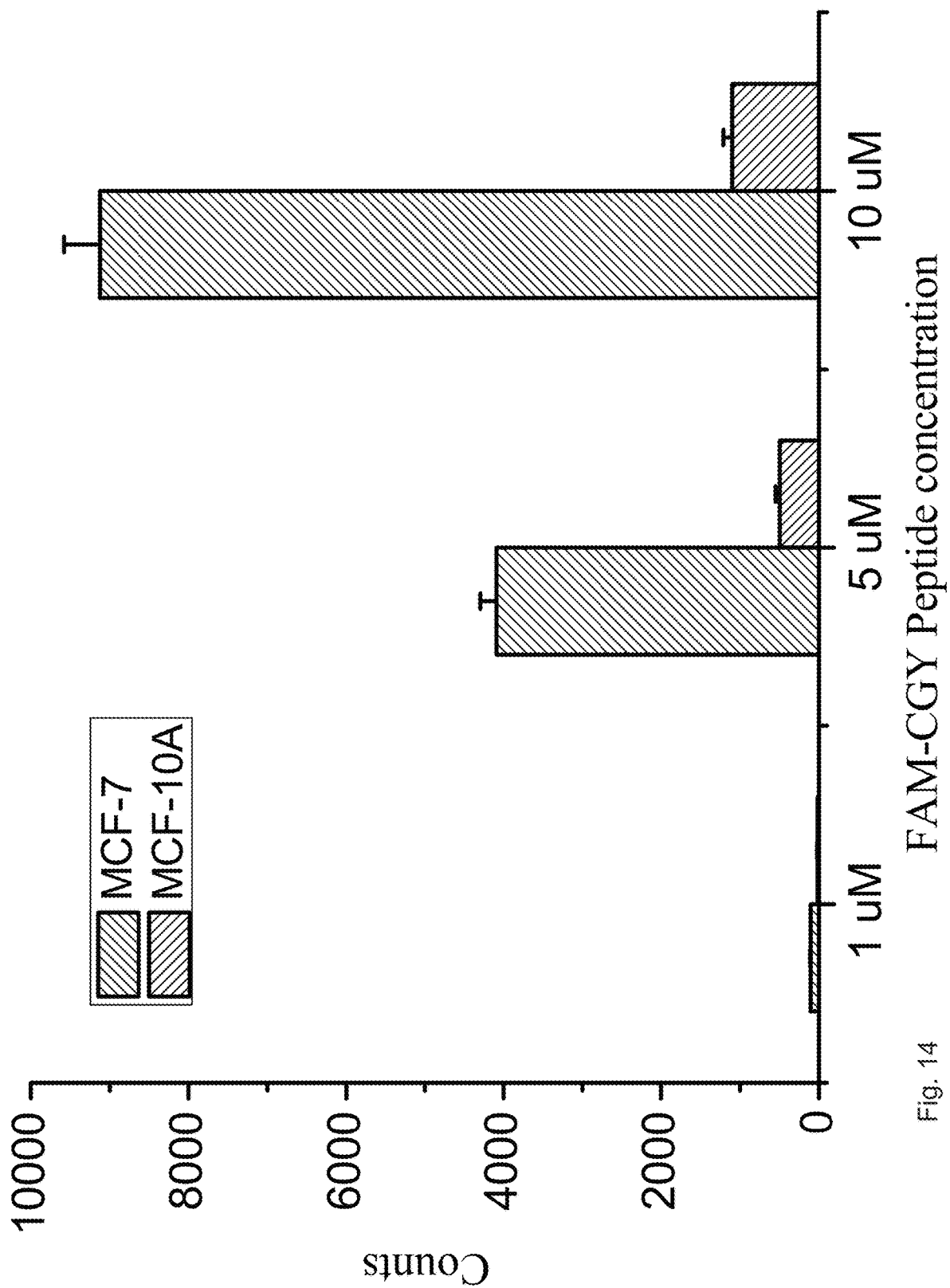
FIG. 14 is chart showing the uptake of FAM-CGY quantified by FACS. MCF-7 and MCF-10A cells were incubated with different concentration of FAM-CGY as indicated for 24 h and studied by fluorescence microscopy (not shown).

Investigation of oxygen consumption rate (OCR) in hCMEC/D3 cells following incubation with FAM-CGY peptide or siRNA/FAM-CGY complex. The hCMEC/D3 cells were incubated with concentrations 2, 5, 10 or 20 µM of the FAM-CGY peptide for FIG. 27A 8 hours, or FIG. 27B 24 hours, or FIG. 27C different formulation of siRNA/FAM-CGY complex for 24 hours. OCR was monitored in real-time using XF Analyzer (Seahorse Bioscience) and data was thereafter corrected for cell numbers. Untreated cells and cells incubated with different dilutions (100-fold or 300-fold) of Amine or siRNA/Amine group were used as controls. FIG. 27D Standard curve showing the linear relationship between absorbance values from crystal violet staining and hCMEC/D3 cell numbers.

Figure 28A:
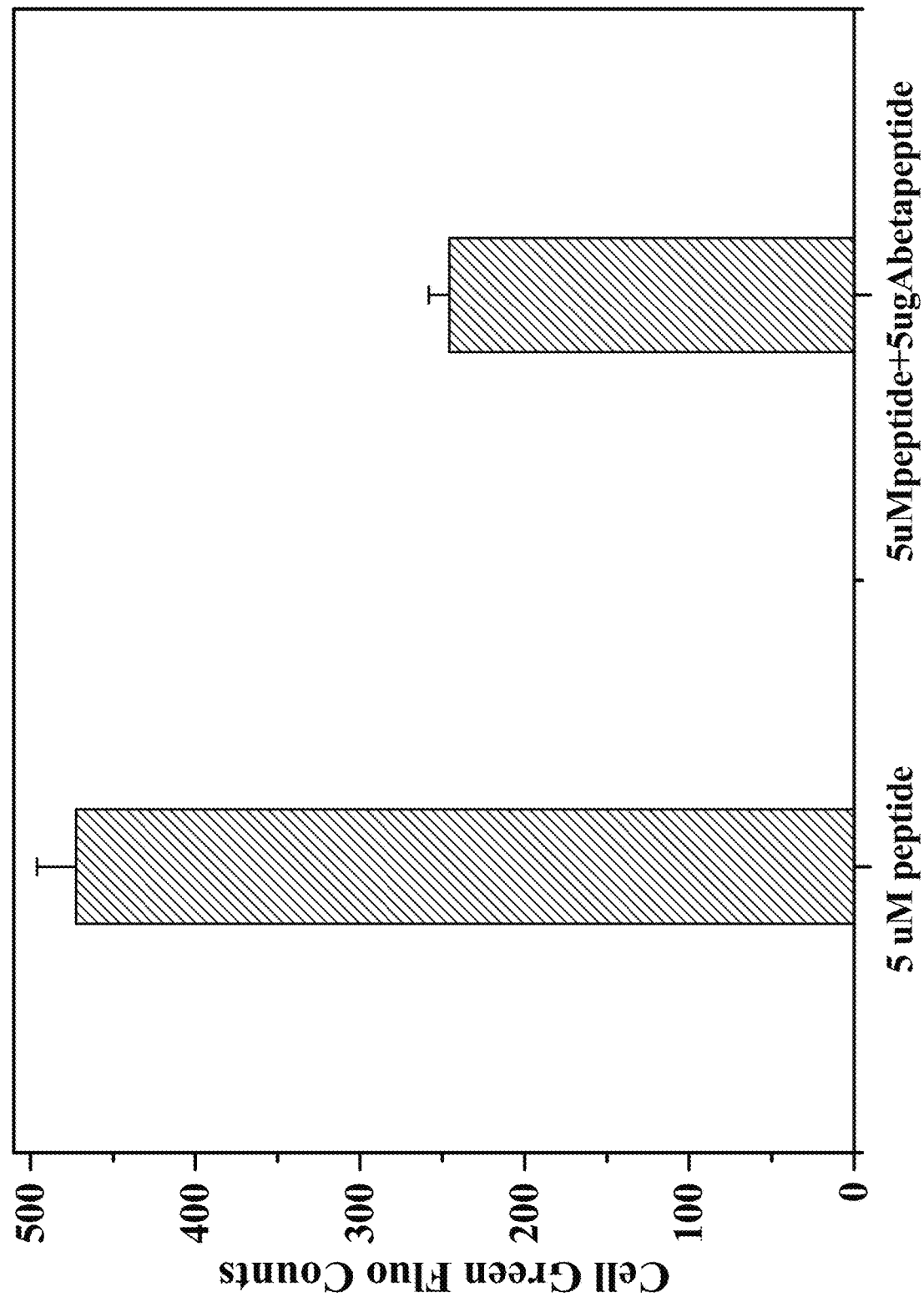

Blockage of amyloid-β peptide uptake by FAM-CGY nanoparticles analyzed by fluorescence microscopy (not shown) and quantified by FACS. FIG. 28A shows a diagram of the number of green cell counts of cells having FAM-CGY bound.

Figure 28B:
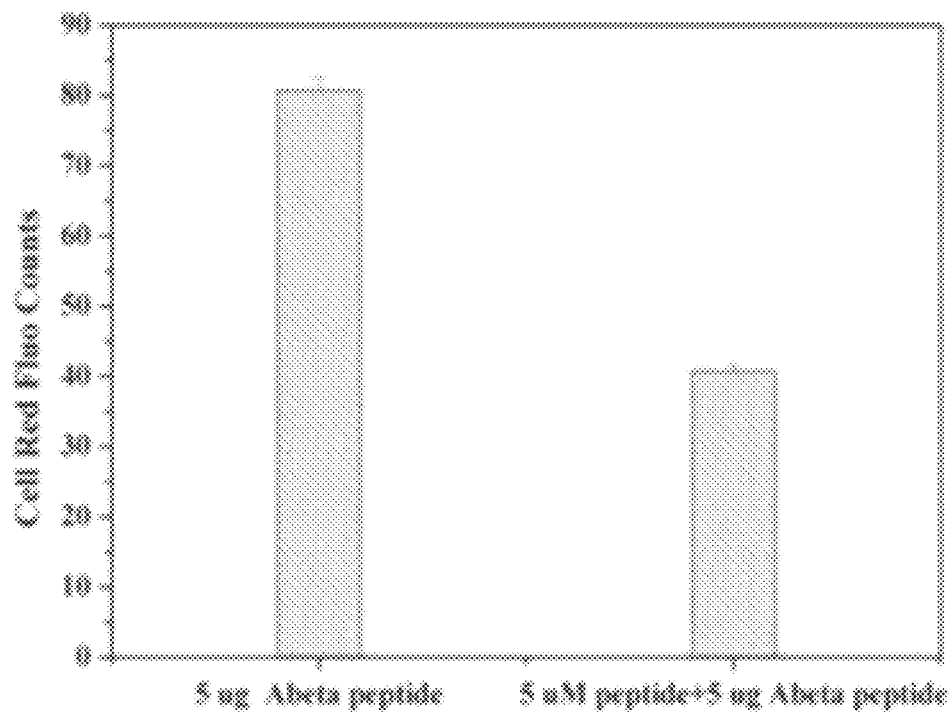

FIG. 28B shows a diagram of the number of red cell counts of cells having amyloid-β bound.

Figure 29A:
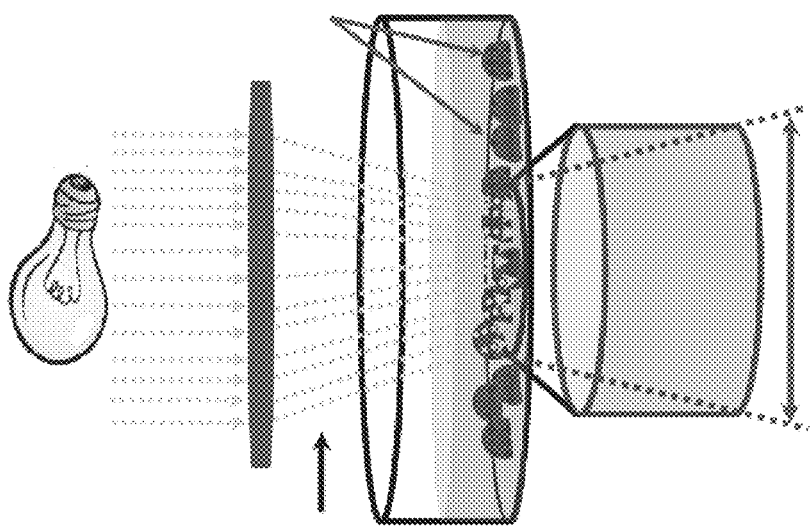
Figure 29B:
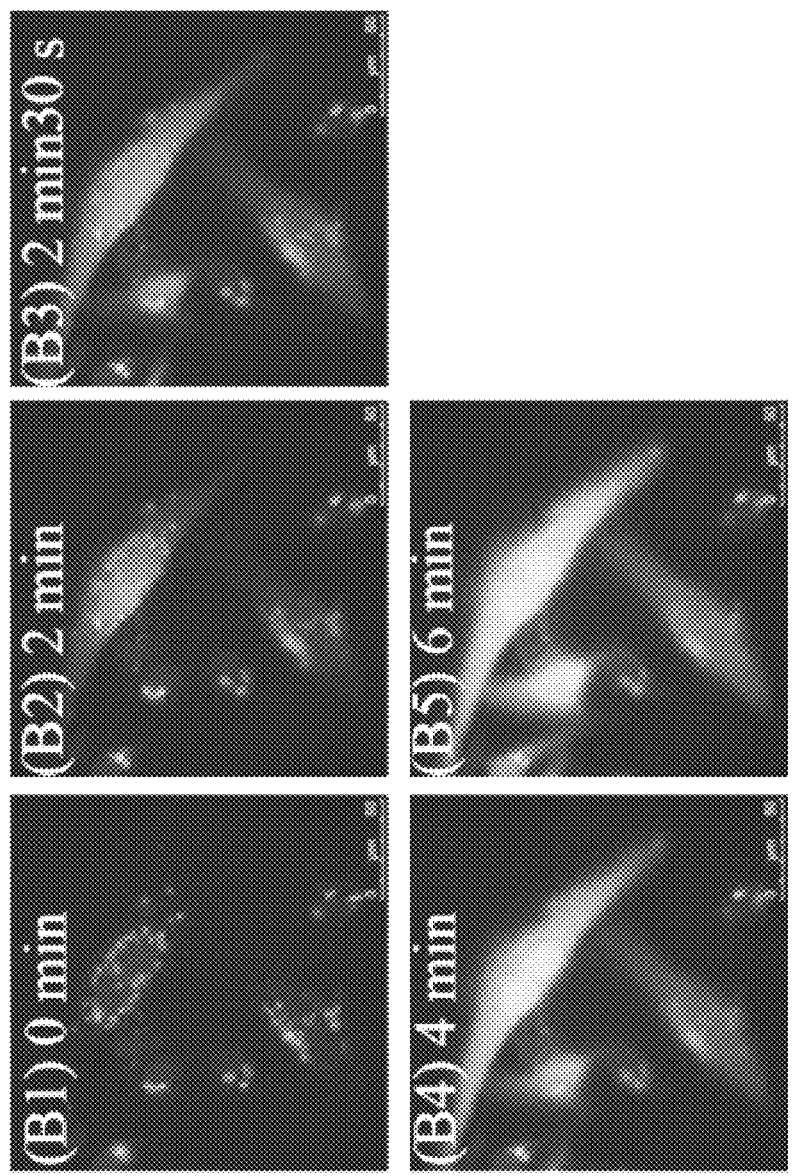

FIG. 29A represents schematic illustration of an in vitro set up for photo-activation of FAM-CGY. The light with designated wavelength is shone from the above using a halogen light source. The dish contain cells with internalised FAM-CGY nanoparticles. These particles are internalised within endo-lysosomal compartments. On photo activation, FAM-CGY destabilises endosomes and FAM-CGY conjugates are released into the cytoplasm. FIG. 29B represents a schematic illustration of an in vitro method light-triggered release of FAM-CGY nanoparticles from compartment vesicles to the cytoplasm using a specific wavelength of light. b. Fluorescence microscopy image of hCMEC/D3 cells exposed to 488 nm light at time points 0, 2, 2.30, 4 or 6 minutes. The cells were incubated with FAM-CGY nanoparticles for 24 h at 37° C.

Figure 30:
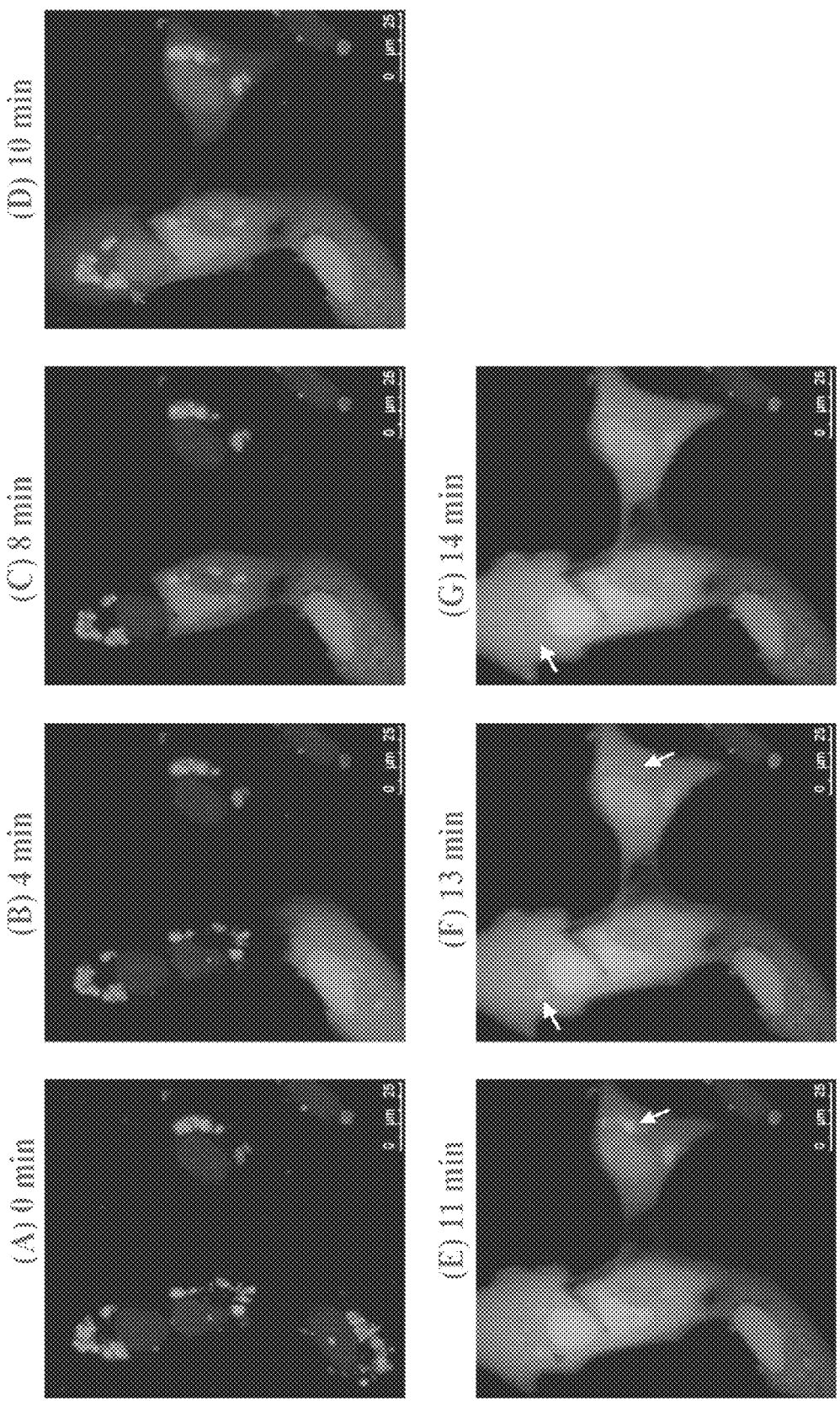

FIG. 30 Light-triggered release of FAM-CGY nanoparticles from compartment vesicles to cytoplasm. hCMEC/D3 cells exposed to the 488 nm light at 0, 4, 8, 10, 11, 13 or 14 minutes. The cells were incubated with FAM-CGY nanoparticles for 24 h at 37° C. prior light exposure.

Figure 31:
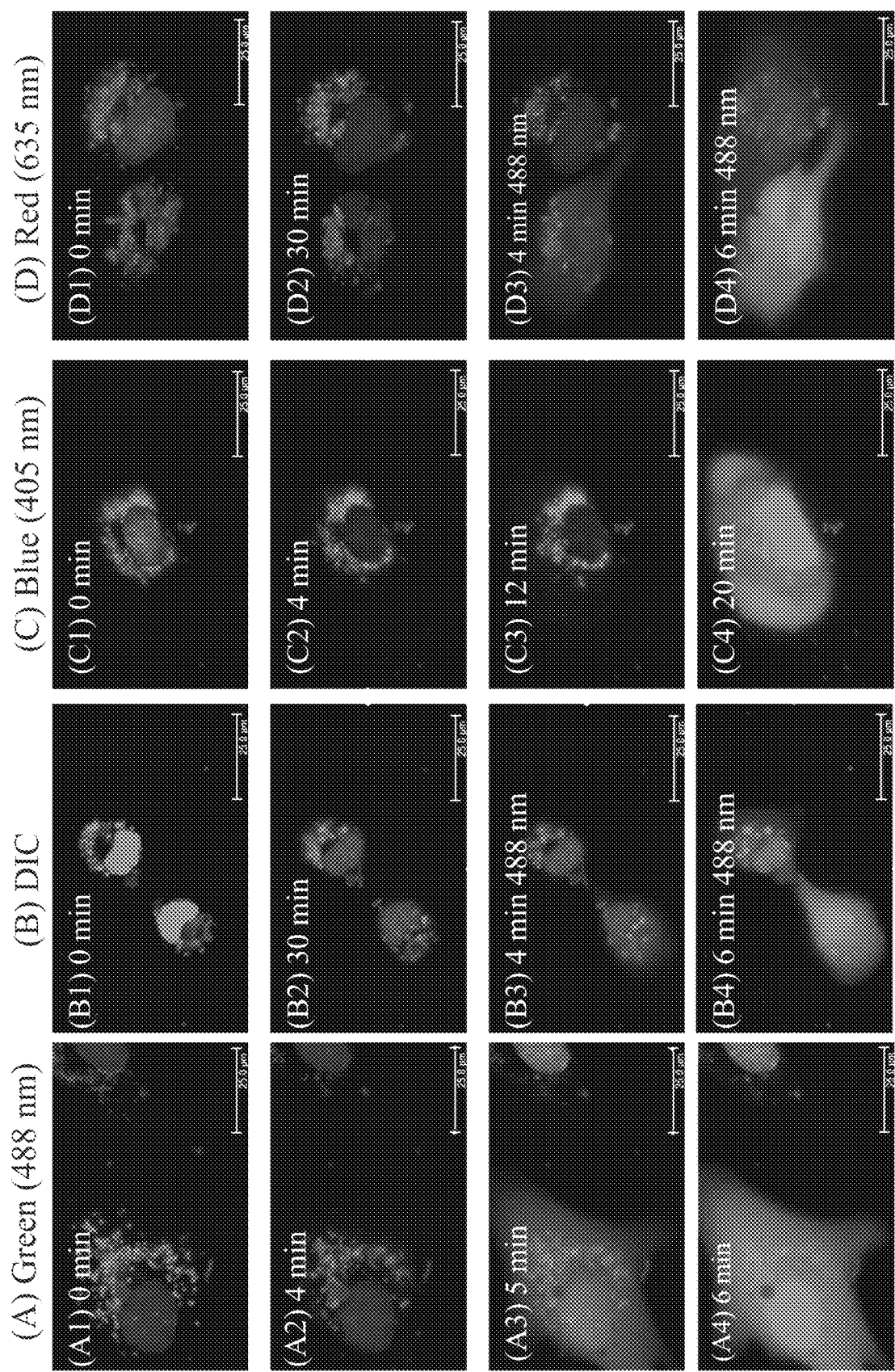

FIG. 31 Fluorescence microscopy image of energy dependent controlled release of FAM-CGY nanoparticles from compartment vesicles to cytoplasm. hCMEC/D3 cells were exposed to differential interference contrast microscopy (DIC), and wavelengths of 488 (green), 405 (blue) or 635 (red) nm at different times; 0, 4, 5 or 6 min for the green light, 0 or 30 for DIC, 0, 4, 12 or 20 min for blue light and 0 or 30 for red light. Due to lack of light-triggered release after DIC and red light, those cells were following exposed to green light for 4 and 6 minutes to release the FAM-CGY nanoparticles. All cells were incubated with FAM-CGY nanoparticles for 24 h at 37° C. prior light exposure.

Figure 32A:
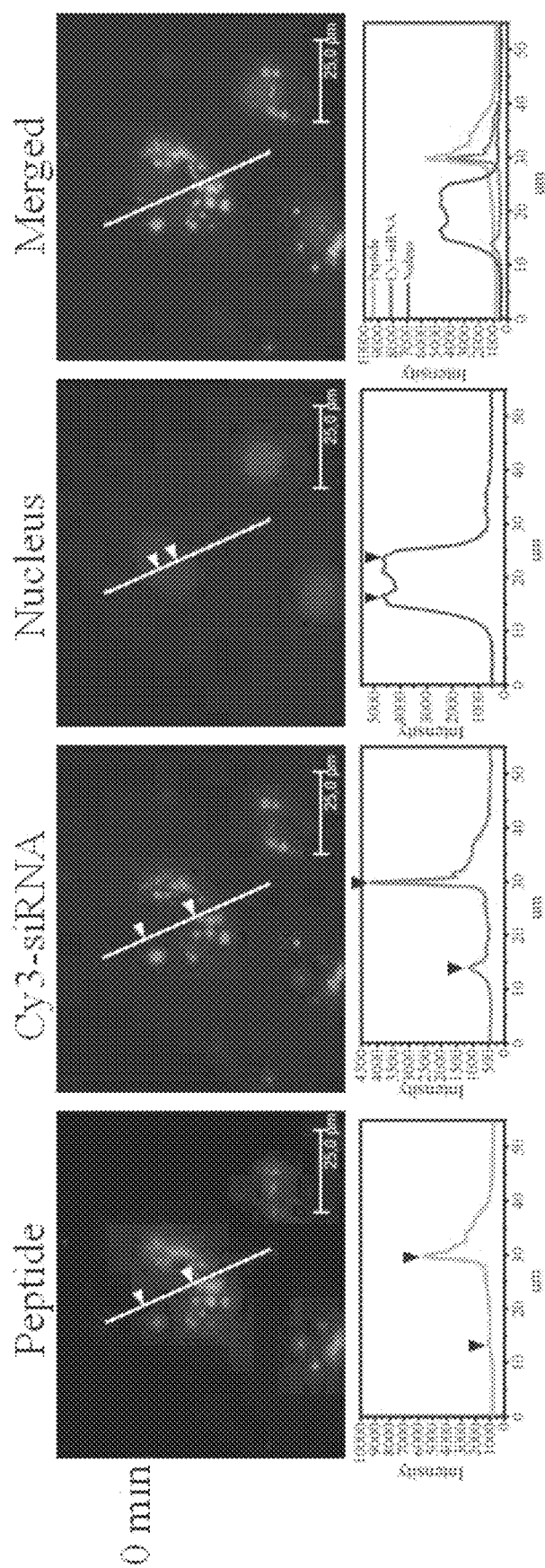
Figure 32B:
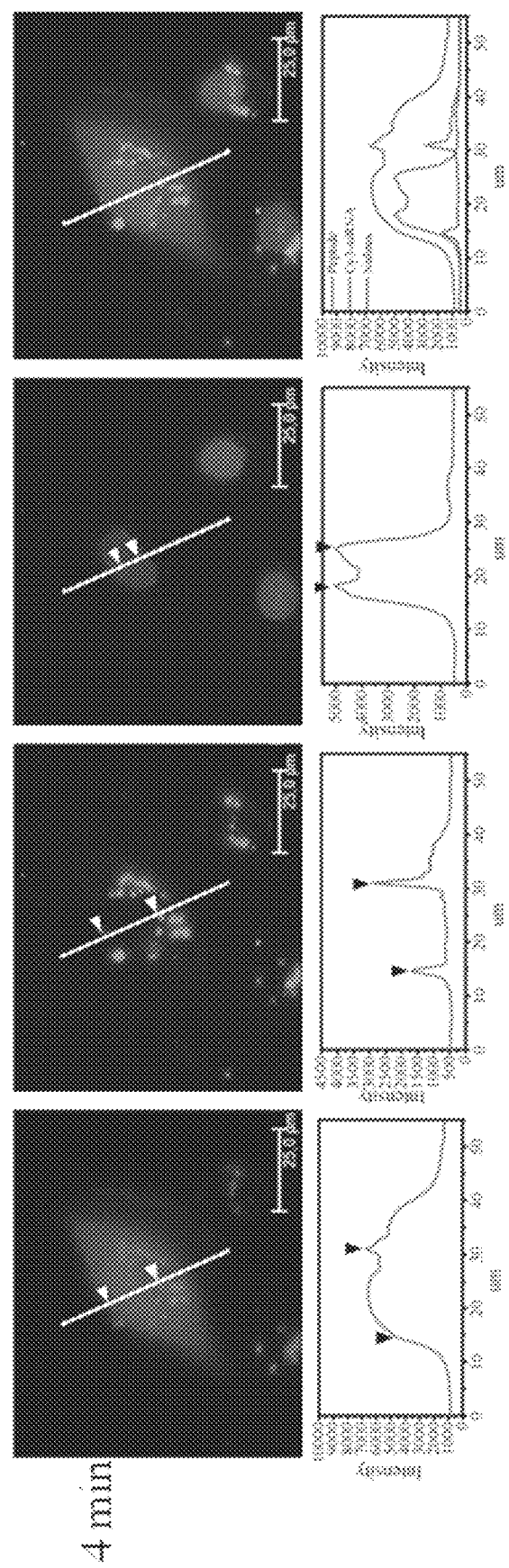
Figure 32C:
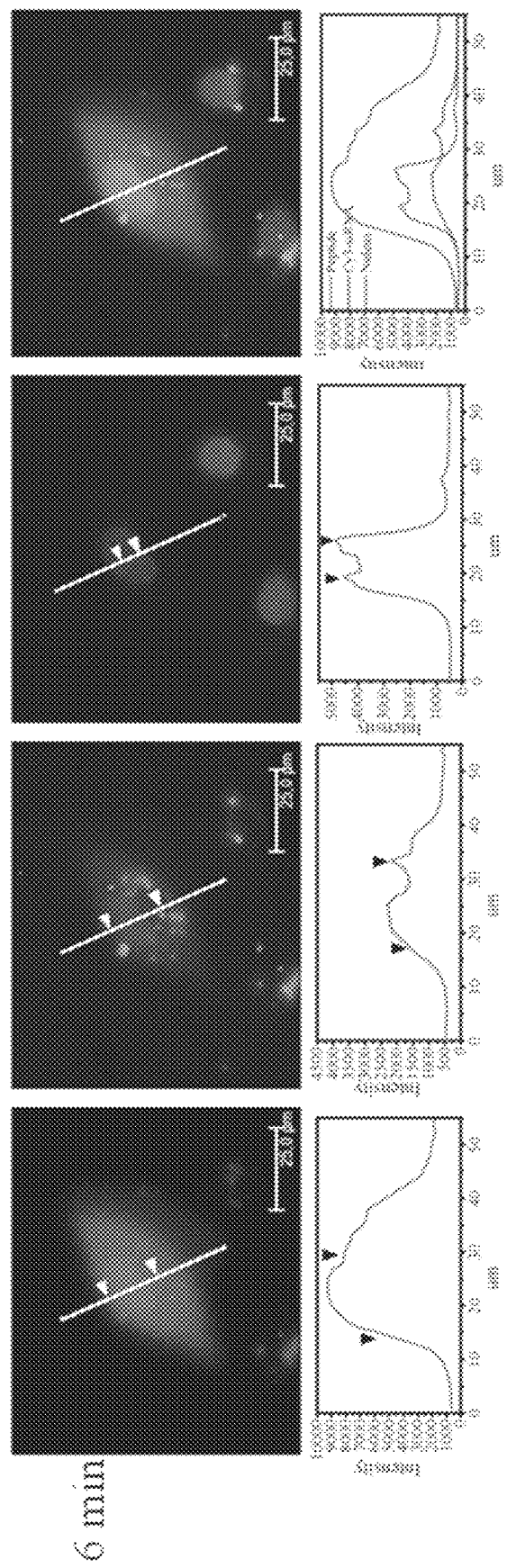

FIGS. 32A, 32B, and 32C are fluorescence microscopy images of in vitro light-triggered release of siRNA by FAM-CGY nanoparticles into the cytoplasm. The fluorescence intensity of the FAM-CGY peptide, Cy3-siRNA and Hoechest 33342 (nucleus stain) in the cytoplasm is measured along the white line in the image. The hCMEC/D3 cells were incubated with Cy3-siRNA/FAM-CGY photosensitive nanoparticle complex at 37° C. for 24 h and exposed to the 488 nm light at 0, 4, and 6 minutes.

Figure 33A:
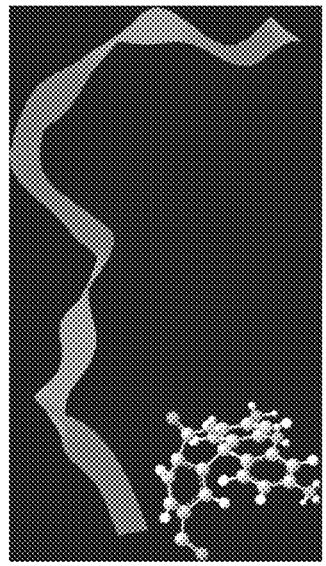
Figure 33B:
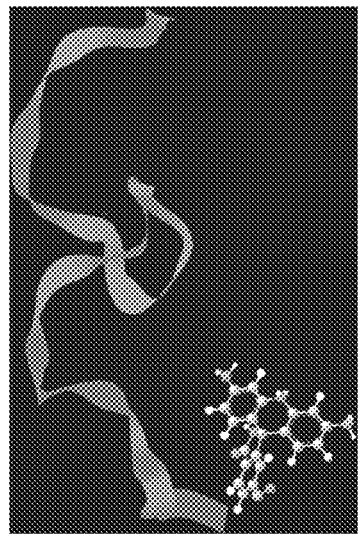

FIG. 33A Sequence of FAM-CGY and FAM-GYR-GYR peptide sequence of a. FAM-CGY peptide and FIG. 33B FAM-GYR-GYR, and corresponding molecular energy-minimization models using Chem BioOffice software.

Figures 34A, 34B:
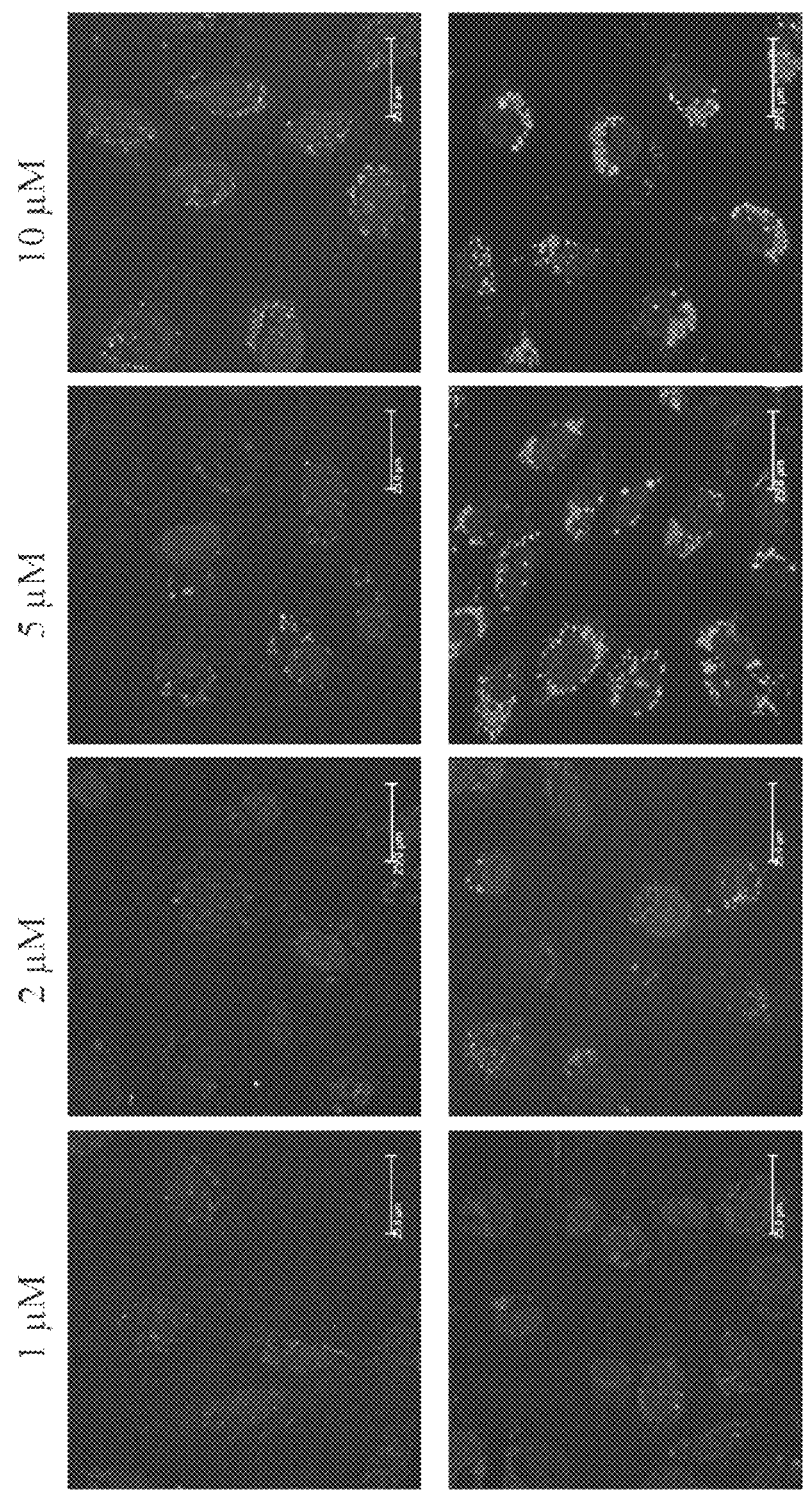

FIGS. 34A and 34B are fluorescence microscopy images of the dose-depended vesicular uptake of FAM-CGY and FAM-GYR-GYR peptide in hCMEC/D3 cells. The cells were treated with concentrations of 1, 2, 5 or 10 µM of FAM-CGY and FAM-GYR-GYR and stained with Hoechest 33342 prior fluorescence microscopy after 24 h (a) (Insert bars=25 µm).

Figure 35:
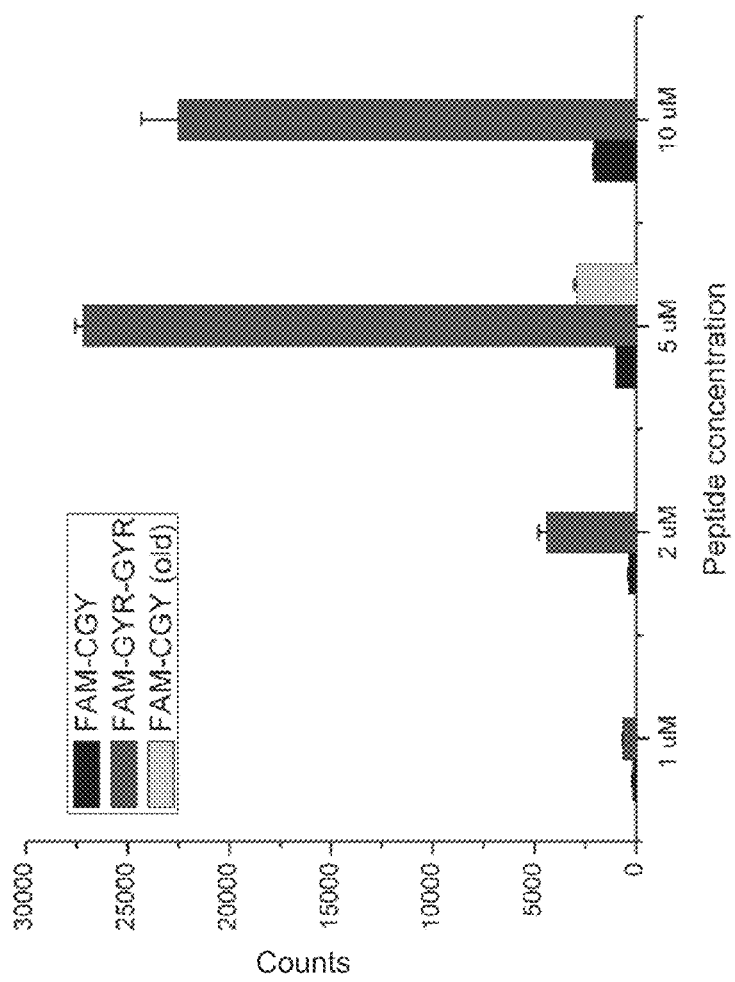

FIG. 35 Comparison of the uptake of FAM-CGY and FAM-GYR-GYR peptide by hCMEC/D3 cells. Cells were treated with concentrations of 1, 2, 5 or 10 µM of FAM-CGY and FAM-GYR-GYR and the peptide uptake were quantified by FACS.

Figure 36:
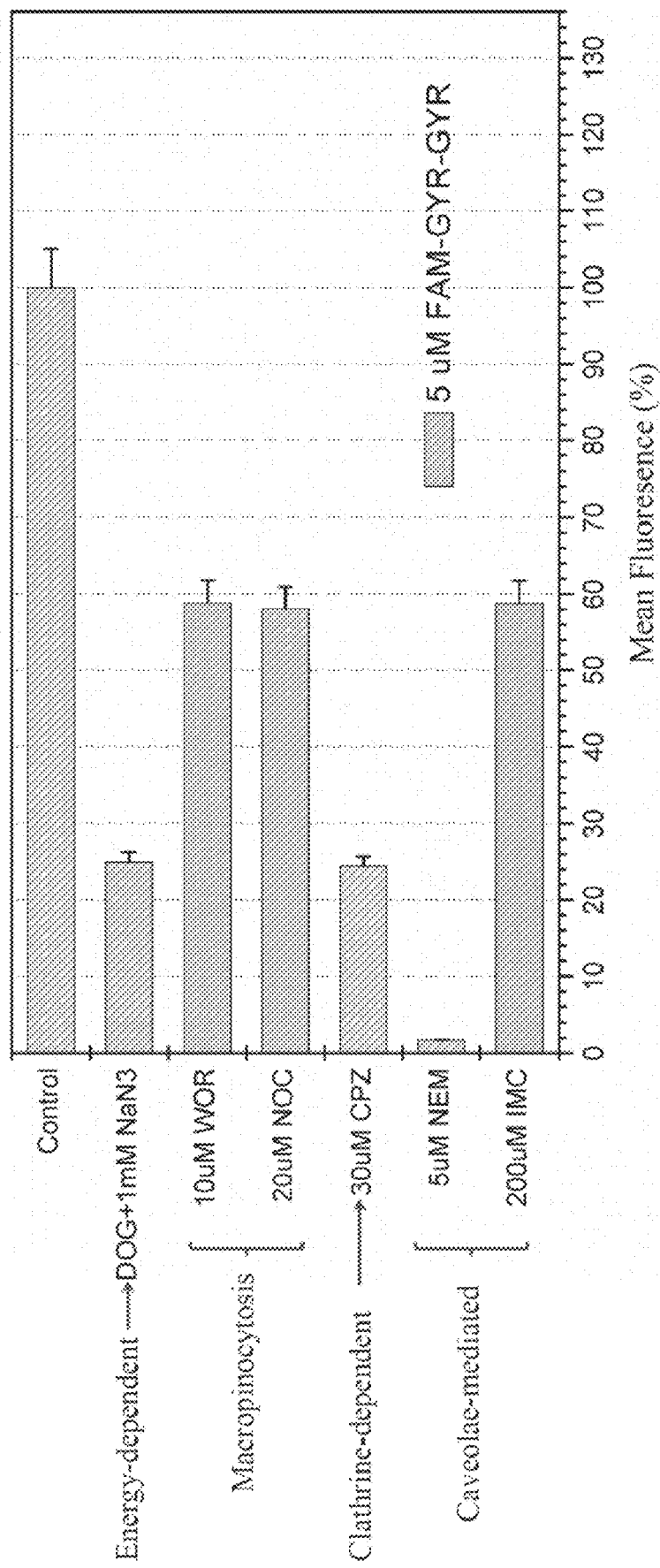
Figure 37B:
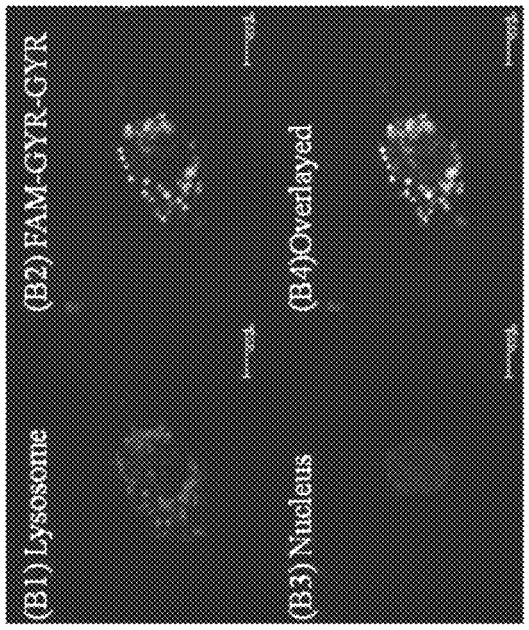
Figure 37D:
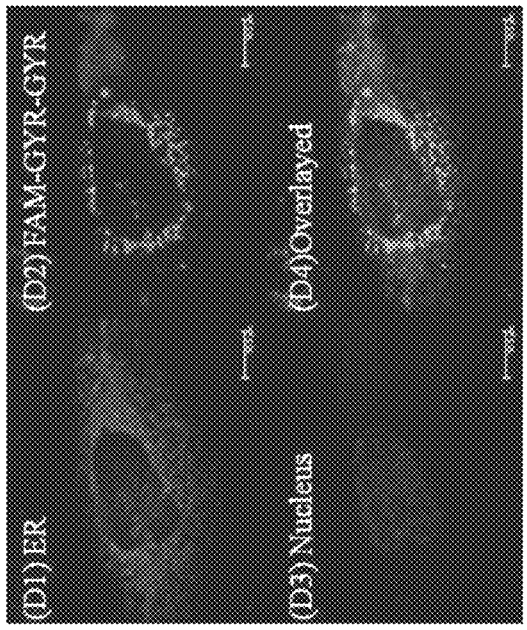
Figure 37A:
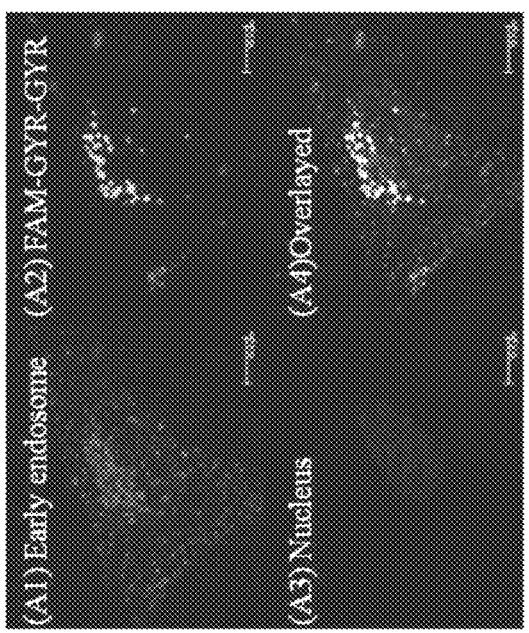
Figure 37C:
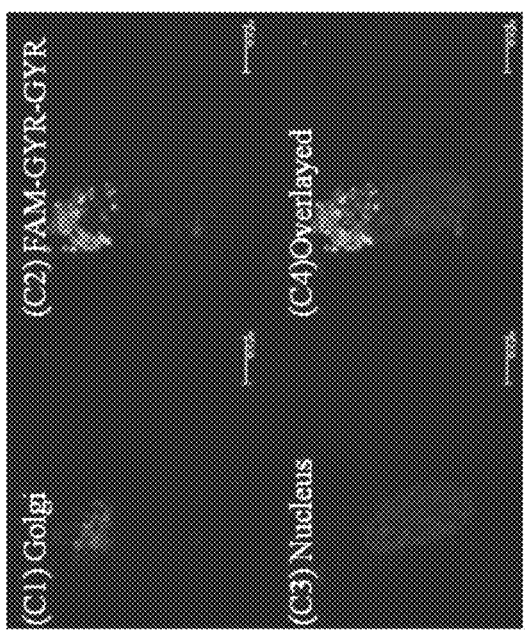

FIG. 36 Influence of various endocytosis inhibitors on the hCMEC/D3 cells uptake of FAM-GYR-GYR peptide. FACS analysis of hCMEC/D3 cells incubated with FAM-GYR-GYR peptide in the presence inhibitors: Energy dependent inhibitor: 1 mM 2-deoxy-D-glucose (DOG) and 1 mM NaN3. Macropinocytosis inhibitor: 10 µM worthmanin (WOR). Fluid phase endocytosis inhibitor: 20 µM nocodazole (NOC). Clathrin-dependent inhibitor: 30 µM chlorpromazine (CPZ). Caveolae-medicated inhibitor: 5 µM N-ethylmaleimide (NEM). Caveolae-dependent endocytosis: 200 µM indomethacin (IMC). The graph displays mean fluorescence intensities of one of three independent experiments performed in duplicate.

FIGS. 37A, 37B, 37C and 37D are fluorescence microscopy images showing intracellular trafficking of FMA-GYR-GYR peptide in different organelles after 4 h incubation. The hCMEC/D3 cell organelles were labelled with CellLight® Early endosomes-RFP, Lysosomes-RFP, Golgi-RFP, and Endoplasmic reticulum (ER)-RFP, respectively, and the nuclei was stained with Hoechest 33342.

Figure 38:
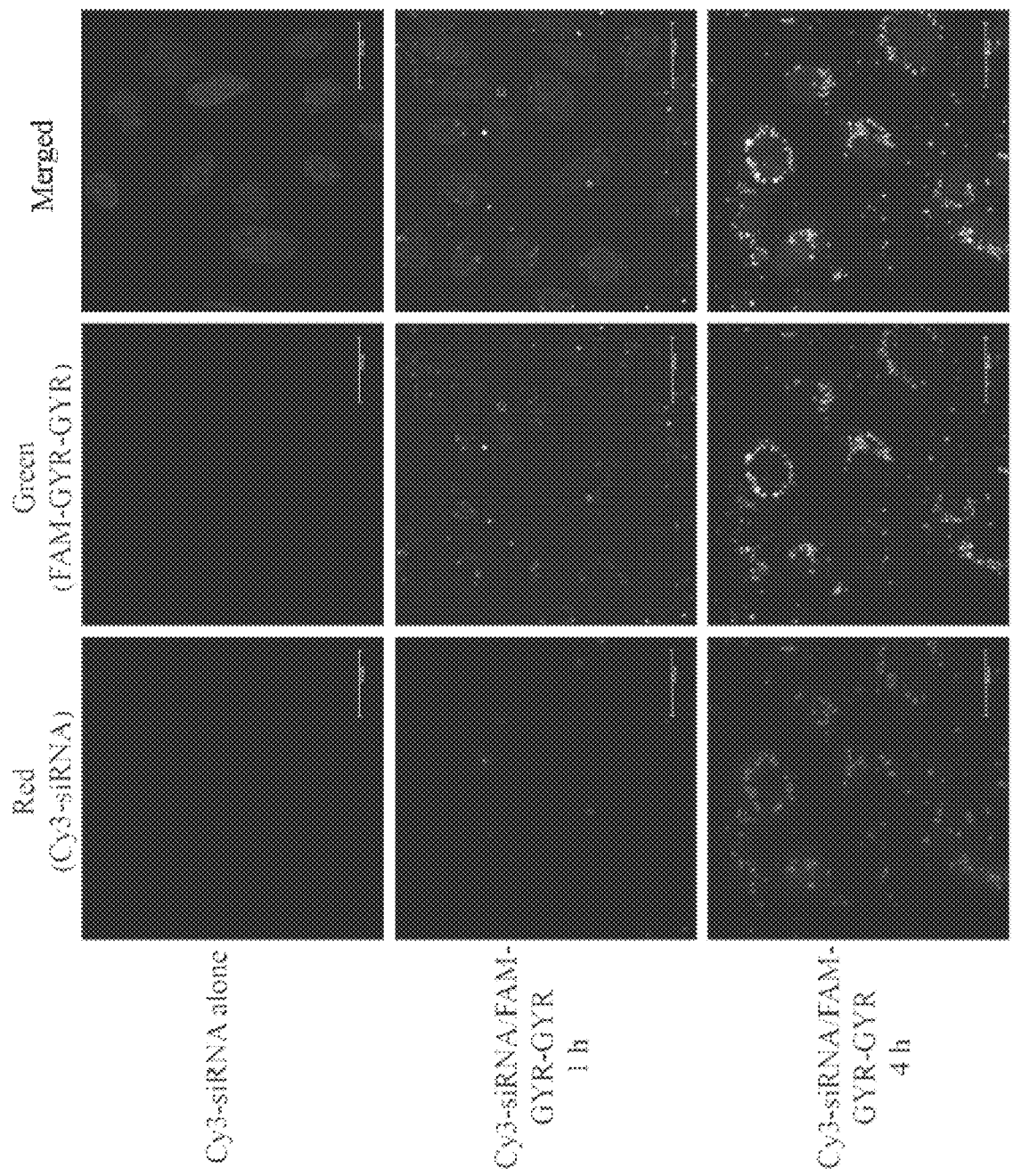

FIG. 38 Fluorescence microscopy image of Cy3-siRNA/FAM-GYR-GYR complex transfection of hCMEC/D3 cells. The cells were incubated with Cy3-siRNA/FAM-GYR-GYR complex as indicated at 37° C. for 1 h or 4 h. The cell nucleus were stained with Hoechest 33342.

Figure 39A:
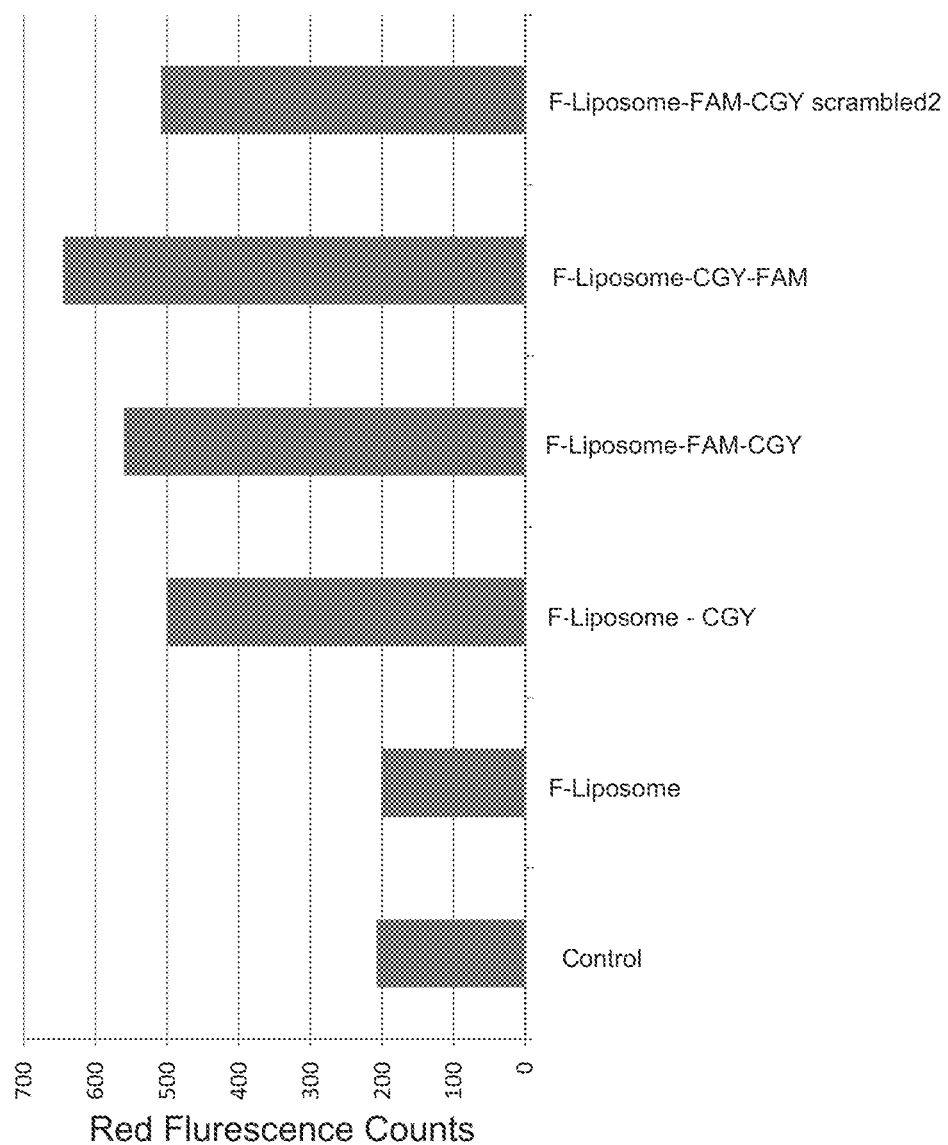
Figure 39B:
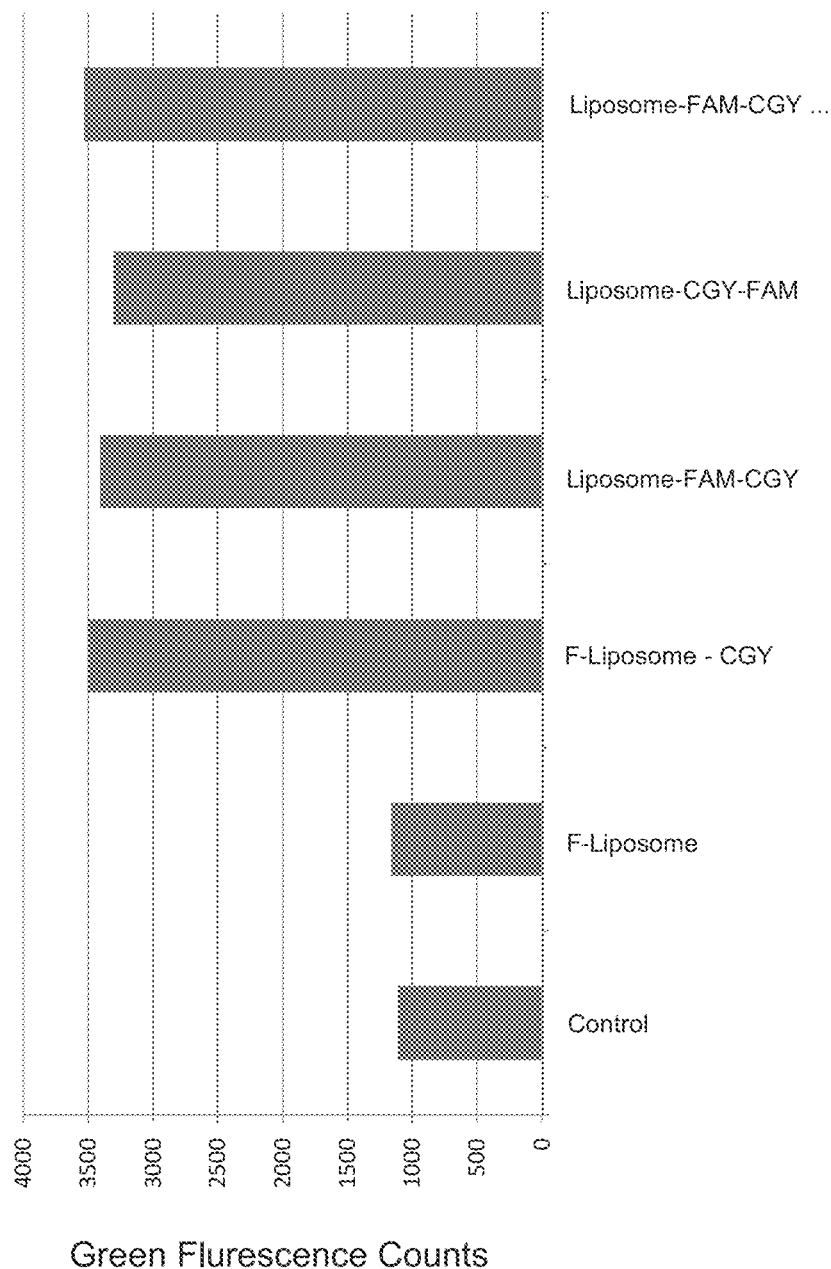

Bar chart showing binding of F-liposome alone, F-Liposome-CGY, F-Liposome-FAM-CGY, F-Liposome-CGY-FAM or F-Liposome-FAM-CGY-scrabled2 conjugates to hCMEC/D3 cells. The cells were analysed by FACS. The liposomes in FIG. 39A were labeled with RED Fluorescent phospholipid and in FIG. 39B with green Fluorescent phospholipid.

Figure 40:
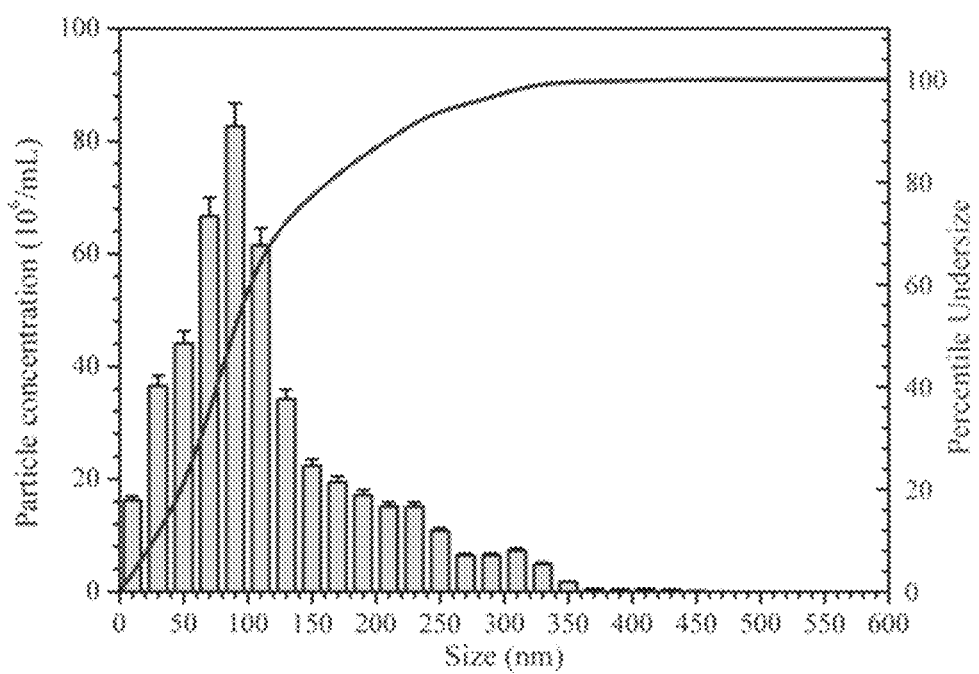

FIG. 40 is a graph showing size distribution of caprylic acid conjugated CGY peptide as measured by nanoparticle tracking analysis (NTA).

FIG. 41-44 are results of studies illustrating formation of peptidic complexes based on rhodamine-linked CGY (Rh-CGY) peptides.

Figure 41A:
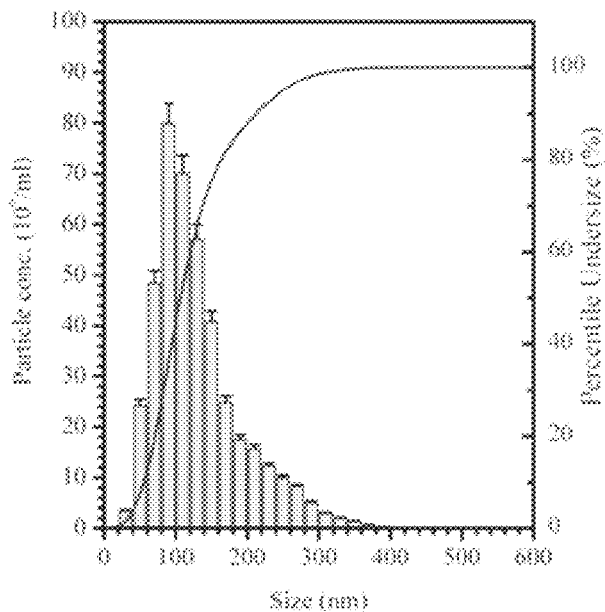
Figure 41B:
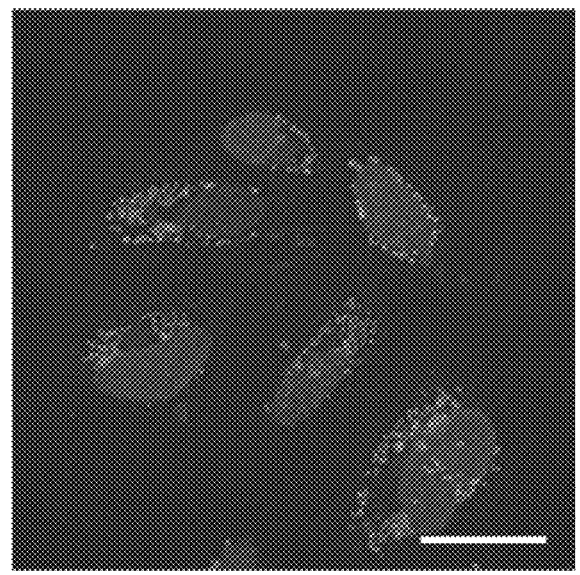

FIG. 41A shows a typical size distribution profile of Rh-CGY peptide (10 µM) self-assembly determined by NTA FIG. 41B shows the uptake of Rh-CGY peptide self-assembly in hCMEC/D3 cells.

Figure 42:
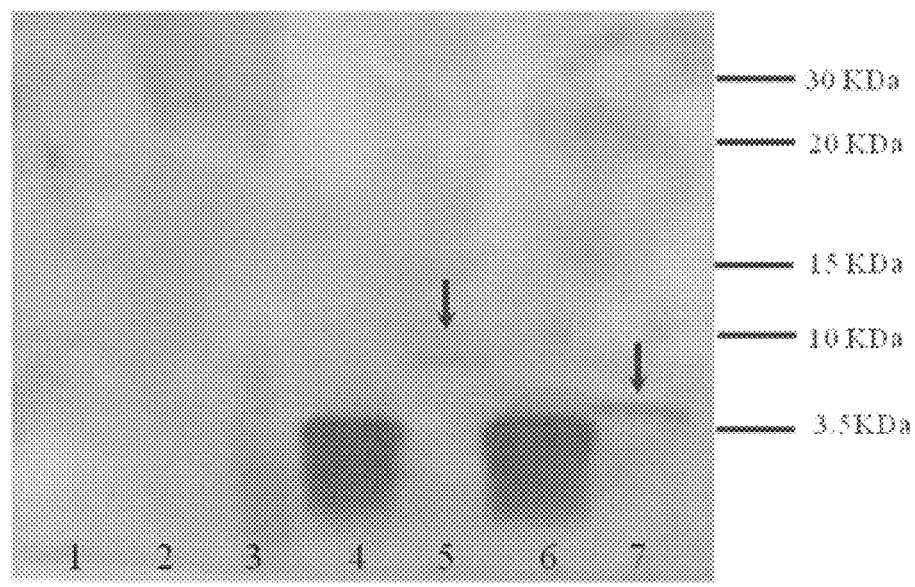

FIG. 42 is a Western blot showing peptidic complexes in a study of Rh-CGY.

Figure 43A:
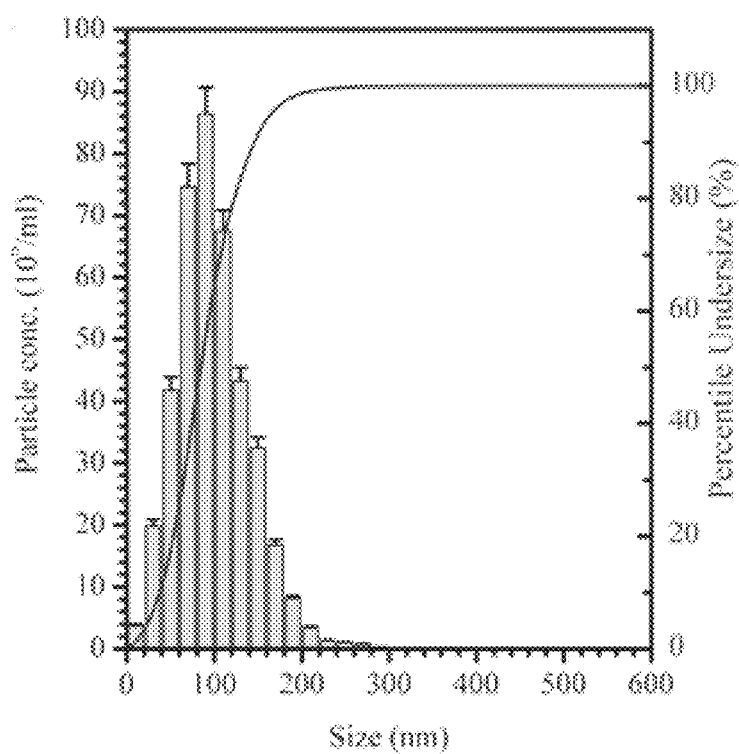
Figure 43B:
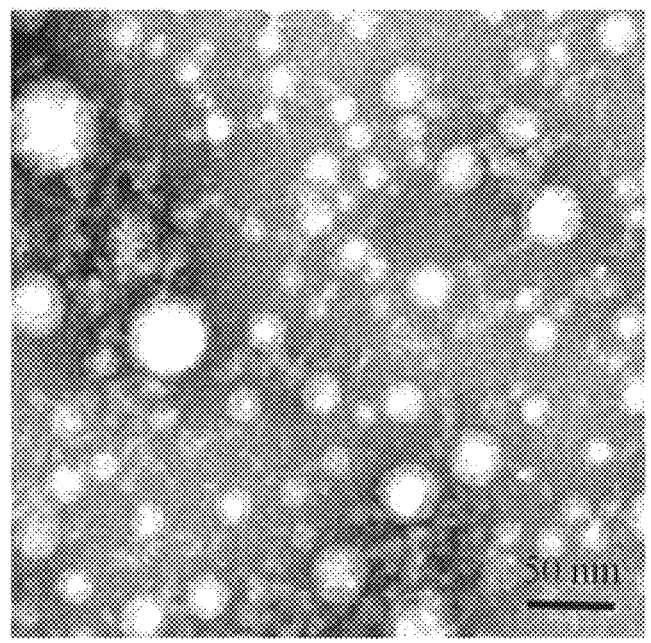
Figure 43C:
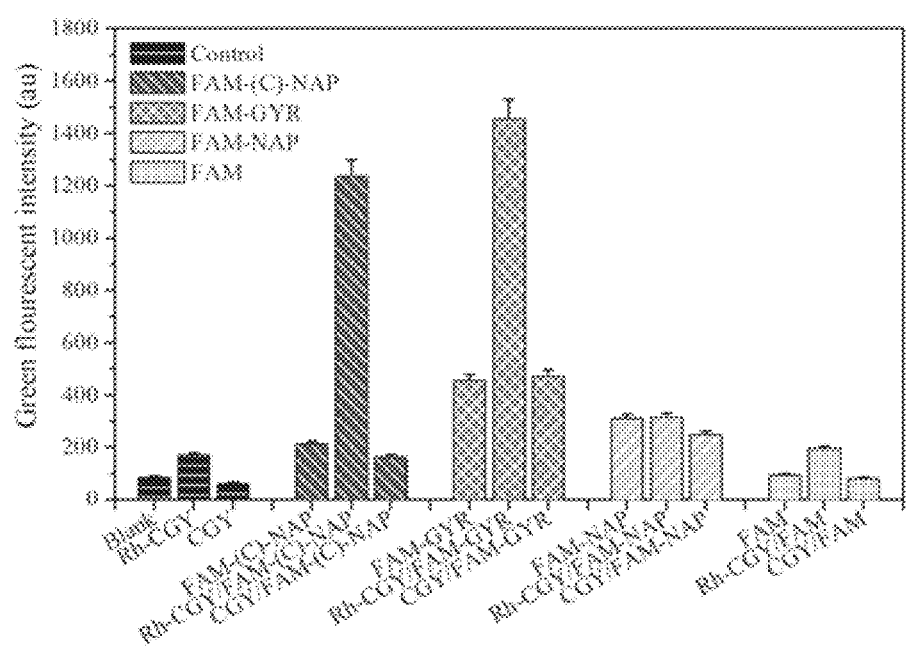
Figure 43D:
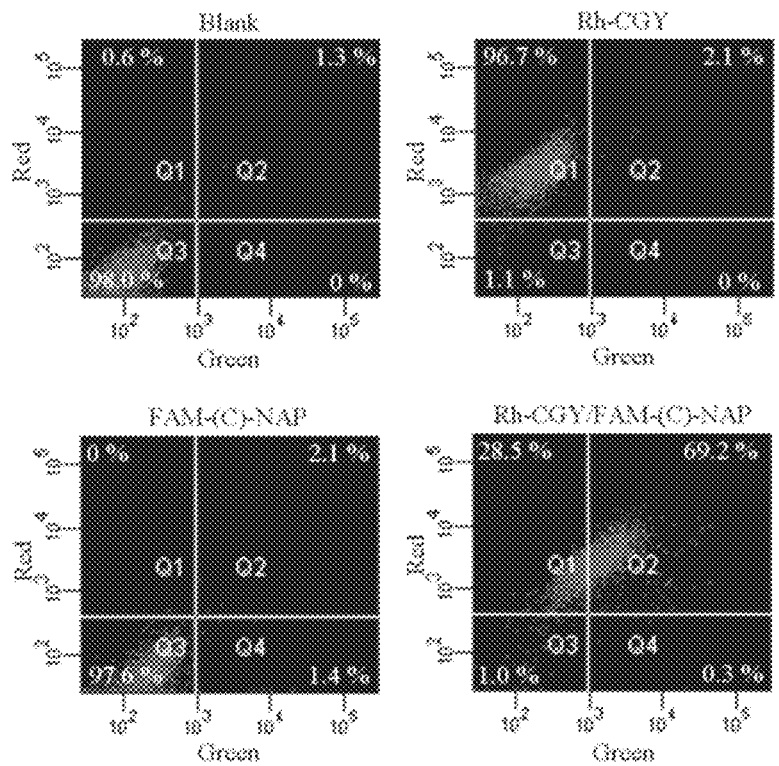
Figure 43E:
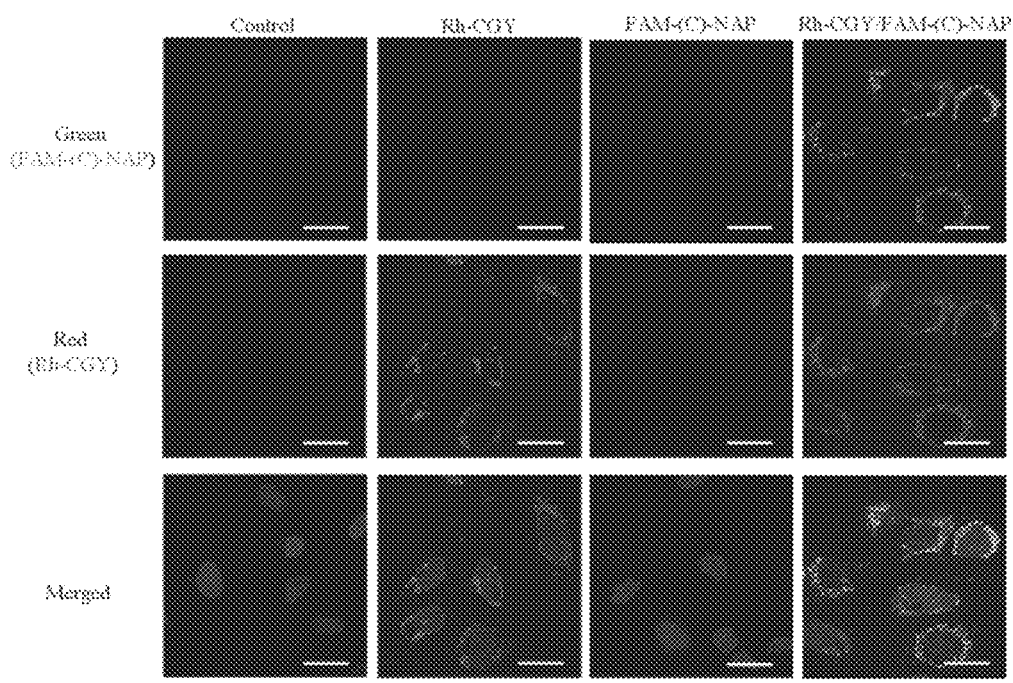

FIG. 43A is a histogram representing a typical size distribution profile of complex species of Rh-CGY (10 µM) with FAM-(C)-NAP peptide (10 µM) determined by NTA. FIG. 43B shows the morphology of Rh-CGY/FAM-(C)-NAP peptidic complex observed by electron microscopy. The Rh-CGY/FAM-(C)-NAP peptide co-self assembles into nanoparticles and fibers. FIG. 43C shows the intracellular intensity of cargoes delivered into hCMEC/D3 cells by the Rh-CGY peptidic based nanosystems using FASC analysis. FIG. 43D is a typical dot plot resulting from a fluorescence-assisted cell sorting experiment of Rh-CGY and FAM-(C)-NAP peptide after treating hCMEC/D3 cells with 10 µM FAM-(C)-NAP, 10 µM Rh-CGY/10 FAM-(C)-NAP complex and 10 µM Rh-CGY for 24 h. FIG. 43E is a photograph of living cell microscopy images of the cells from the study of FIG. 43D.

Figure 44A:
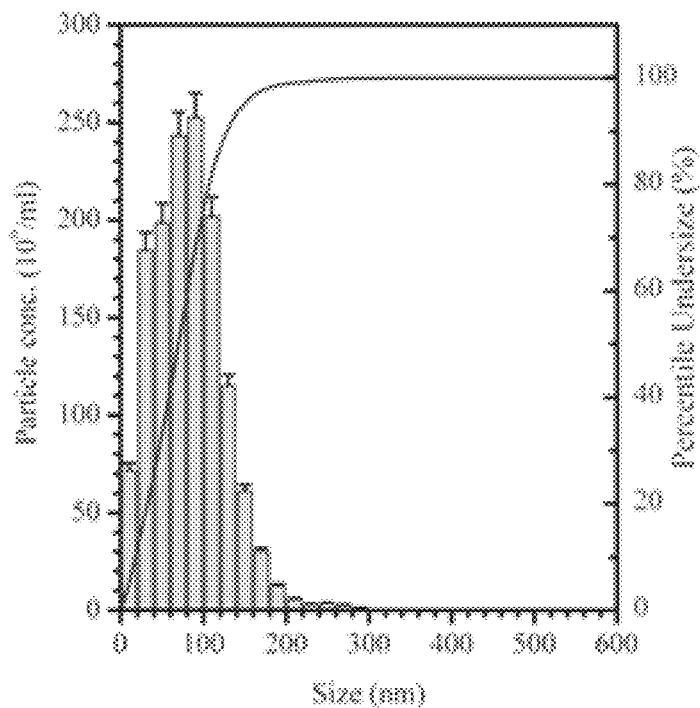
Figure 44B:
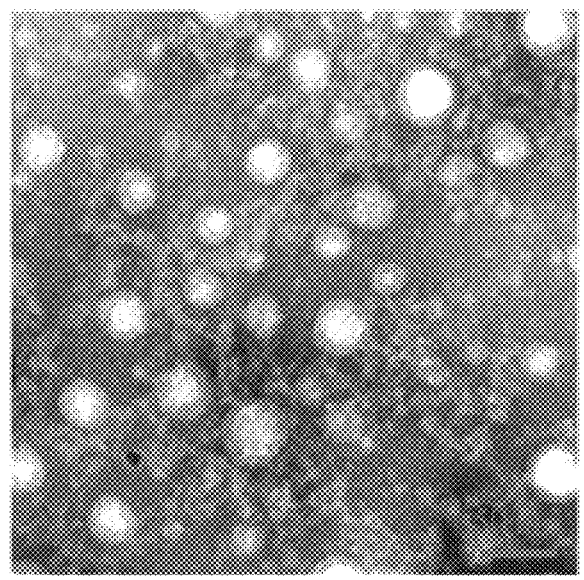

FIG. 44A represents typical size distribution profile of Rh-CGY (10 µM)/FAM-GYR (5 µM) peptidic complex determined by NTA. FIG. 44B shows the morphology of Rh-CGY/FAM-GYR peptidic complex observed by electron microscopy.

Figure 44C:
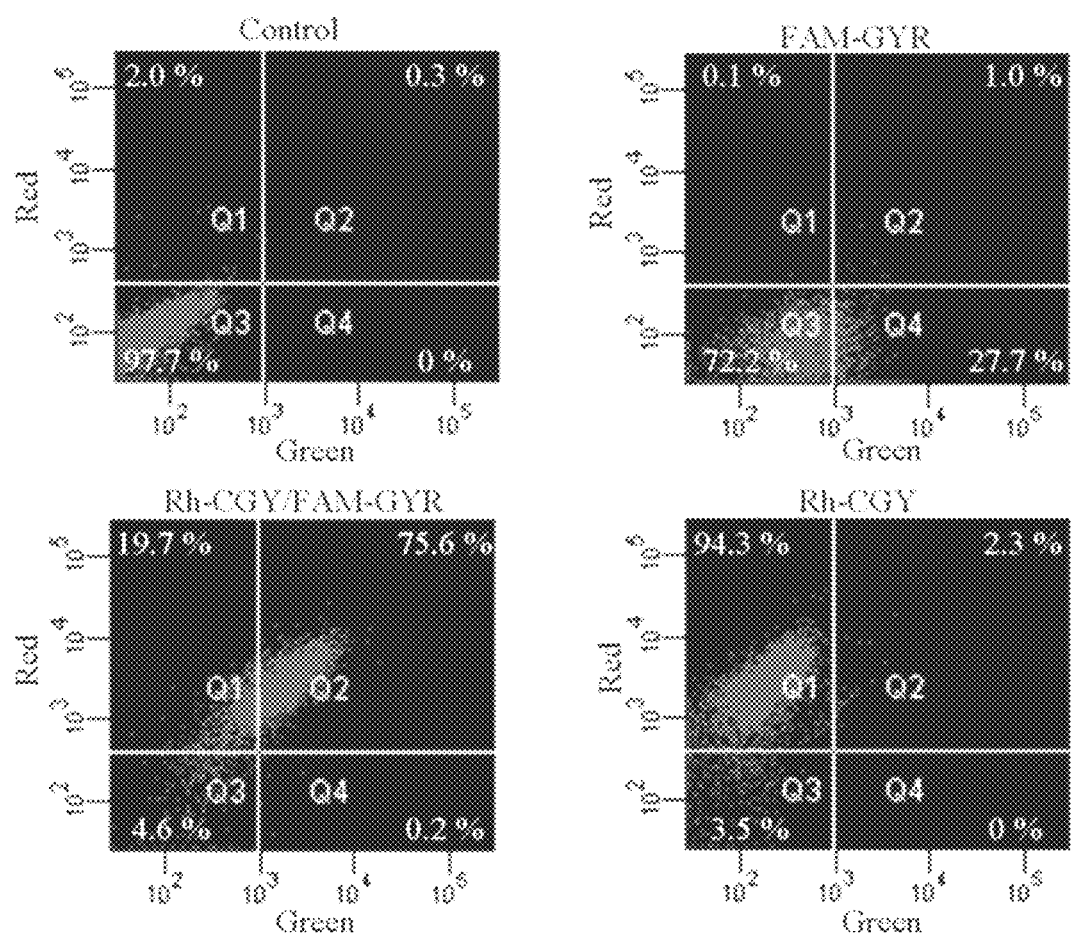
Figure 44D:
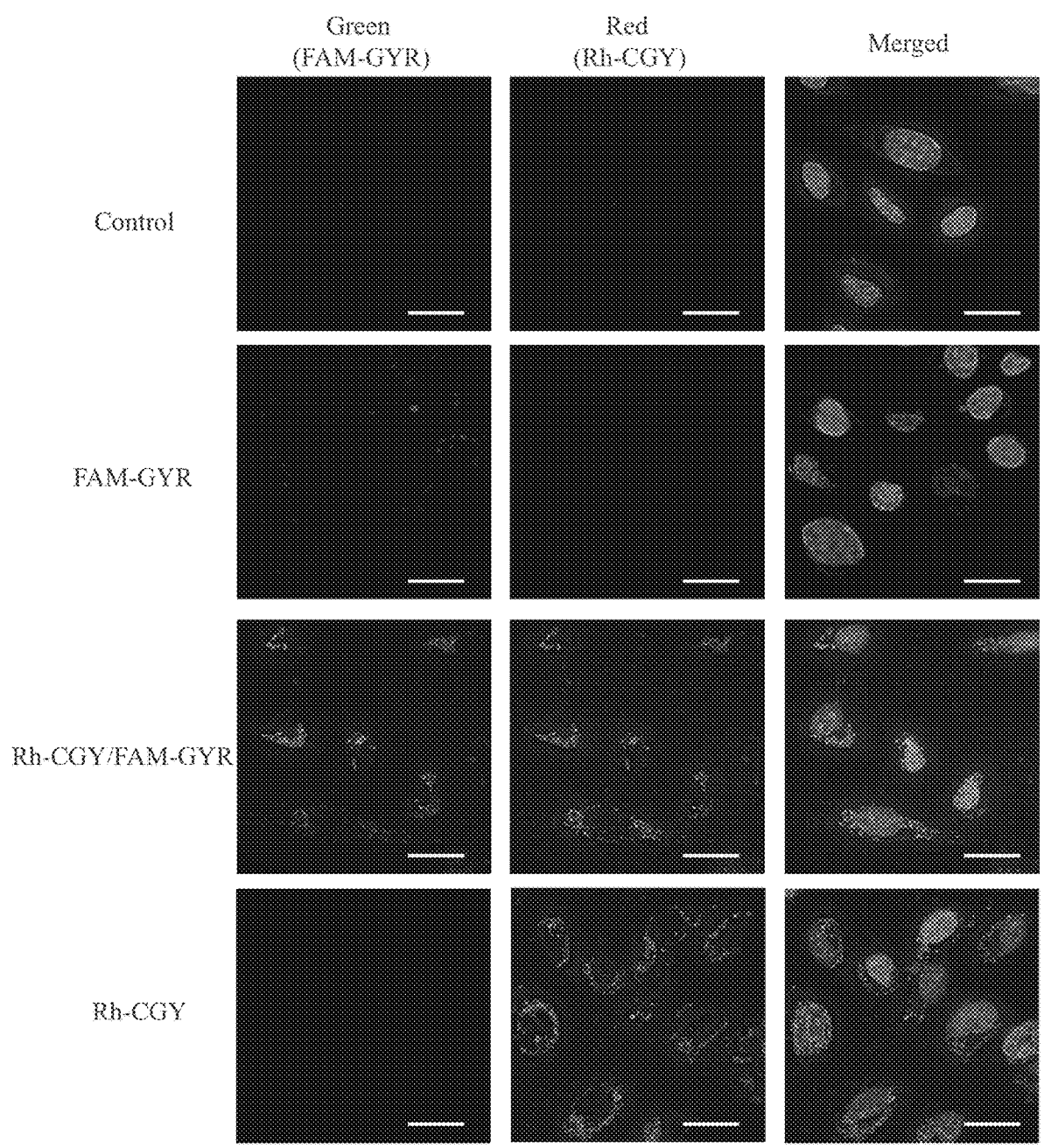

FIG. 44C is a typical dot plot resulting from a fluorescence-assisted cell sorting experiment of Rh-CGY and FAM-GYR peptide after treating hCMEC/D3 cells with 5 µM FAM-GYR, 10 µM Rh-CGY/5 µM FAM-GYR complex and 10 µM Rh-CGY for 24 h. FIG. 44D is a photograph of live cell microscopy images of the cells from the study of FIG. 44C.

Figure 45:
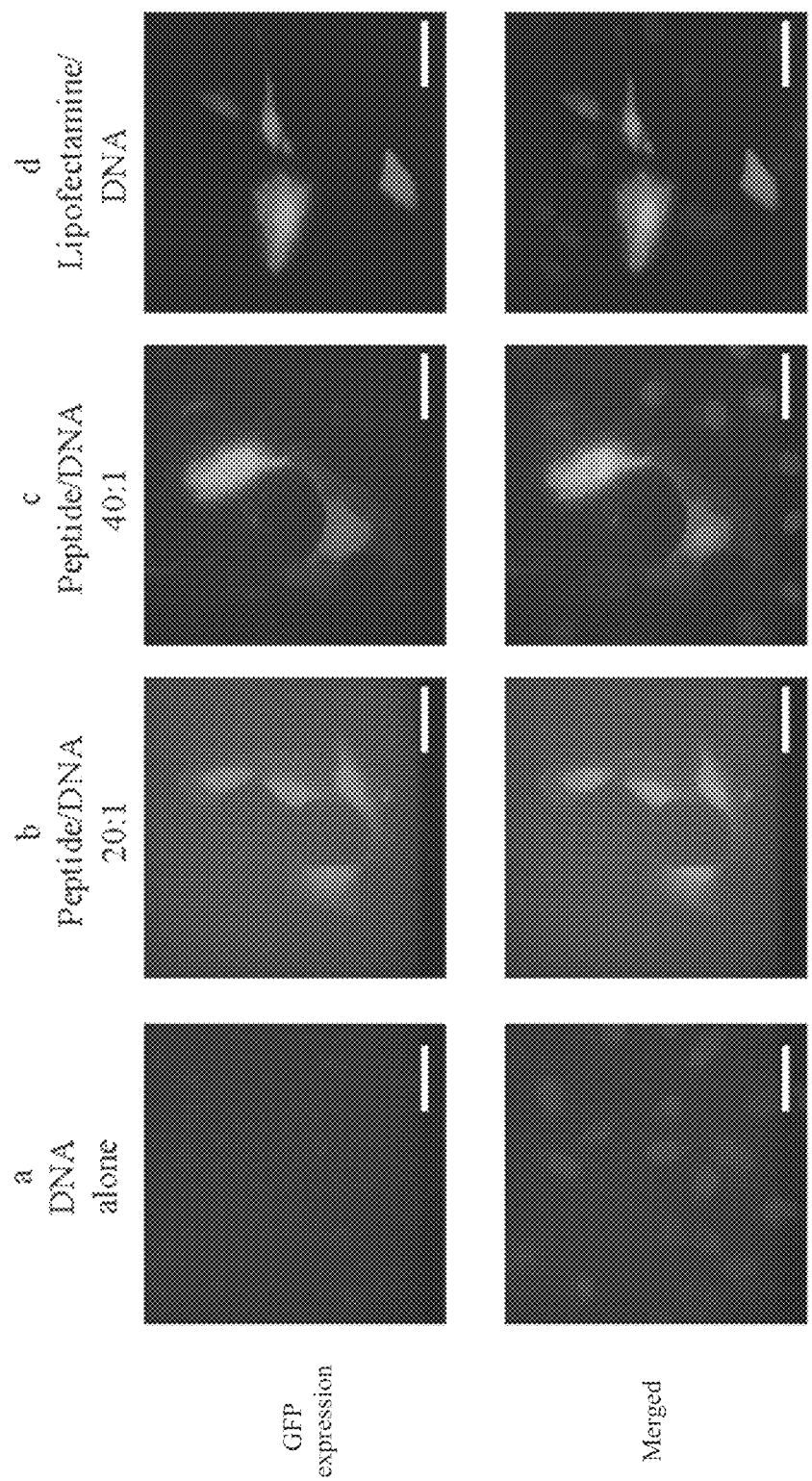

FIG. 45 shows photographs of hCMEC/d3 cells in a study investigating double peptide-mediated nucleic acid transfection.

Figure 46:
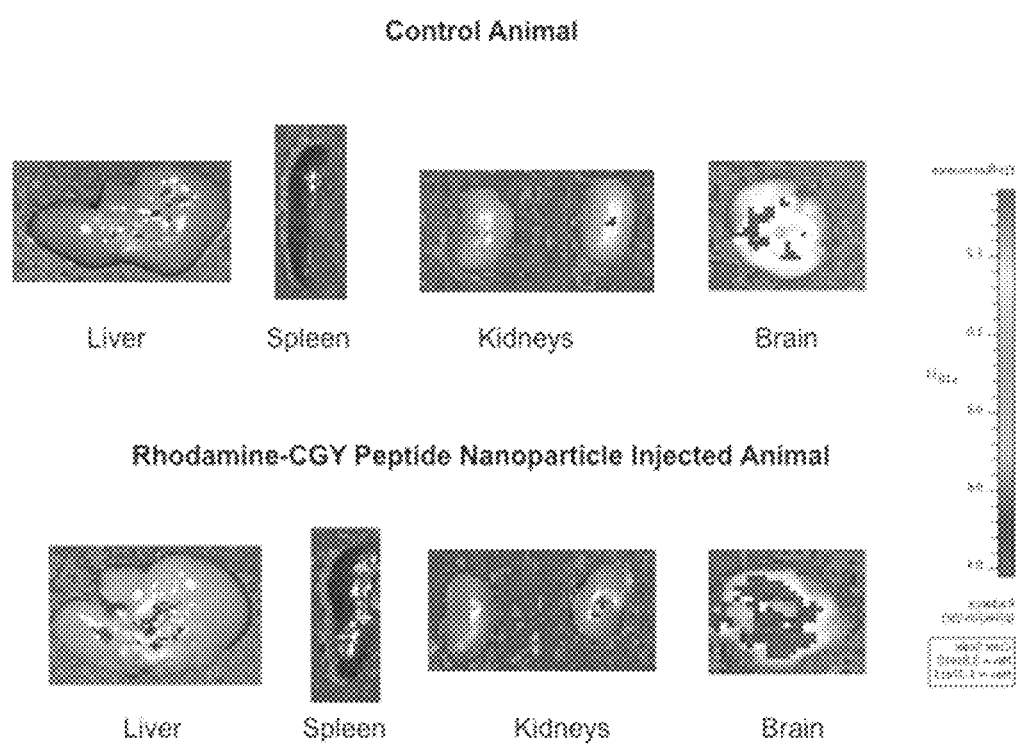

FIG. 46 shows fluorescence imagery of organs from mice involved in in vivo studies of peptide localization.

Figure 47:
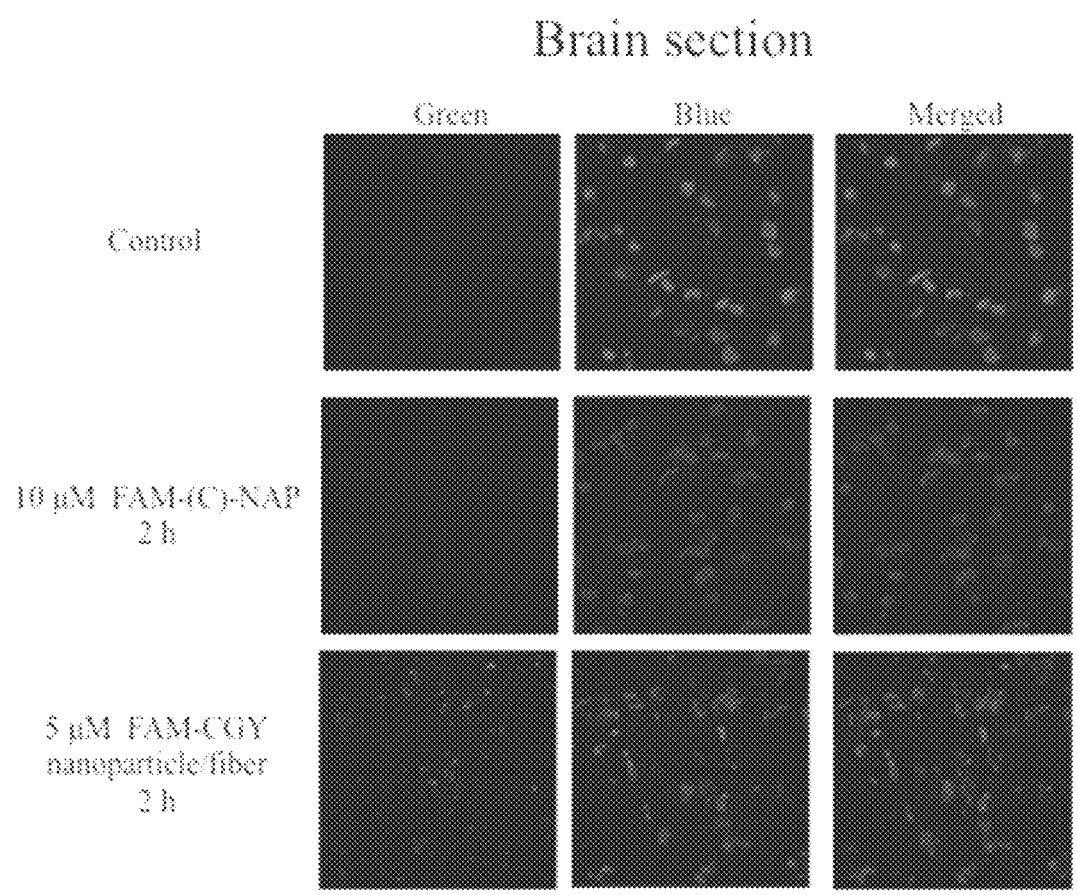

FIG. 47 are photographs of brain cells of mice that were involved in in vivo studies of peptide conjugate localization.

Figure 48A:
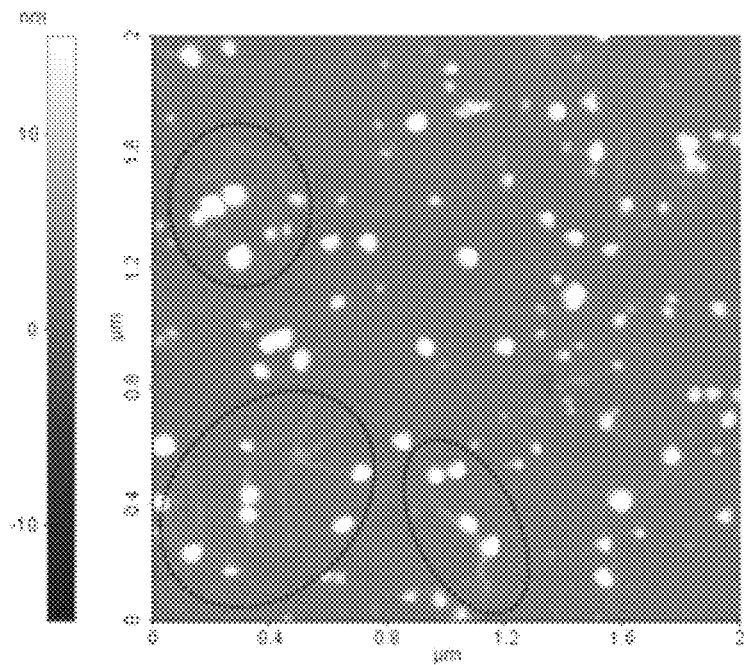
Figure 48B:
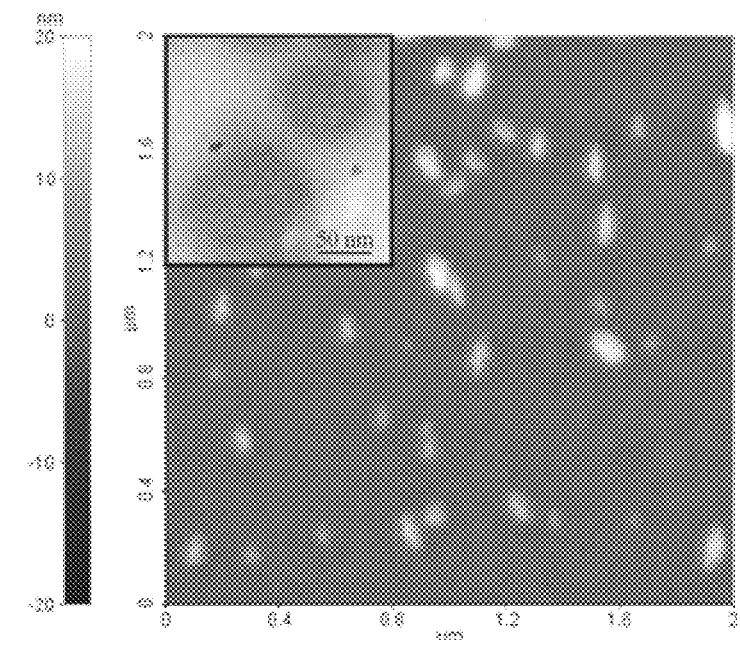

FIGS. 48A through 48G demonstrate the structures of peptide conjugate aggregates. FIGS. 48A and 48B are atomic force microscopy (AFM) images of FAM-CGY (5 µM) species in the absence and presence of 24 nM siRNA (in this case, targeted against the transferrin receptor), respectively. The inset in FIG. 48B is transmission electron micrograph of elliptically-shaped FAM-CGY/siRNA complexes showing the presence of some elongated fibre-like structures in the particle core. The spherical equivalent mean size of nanoparticles is 169±51 nm, based on measurements of at least 100 individual images. FIGS. 48C, 48D, 48E, 48F, and 48G show an overview of peptide nanoparticle-fiber network (48C), a typical core-shell nanoparticle component of the network (48D), a core-shell nanoparticle with elongated hair-like projections (48E), and magnified views of twisted fibre components (48F, 48G). The measured mean size of the core-shell nanoparticles were 116±22 nm (based on measurements of at least 100 randomly selected nanoparticle images.)

DETAILED DESCRIPTION

This section describes the current invention in greater detail using a schematic illustration of a polypeptide conjugate and examples of polypeptide conjugates and their use in a method to for binding and/or internalization of the polypeptide conjugate to a mammalian cell having a transferrin receptor (TFRC) and/or receptor for advanced glycation end products (RAGE). However, this by no means limits the scope of the current invention.

Figure 1:
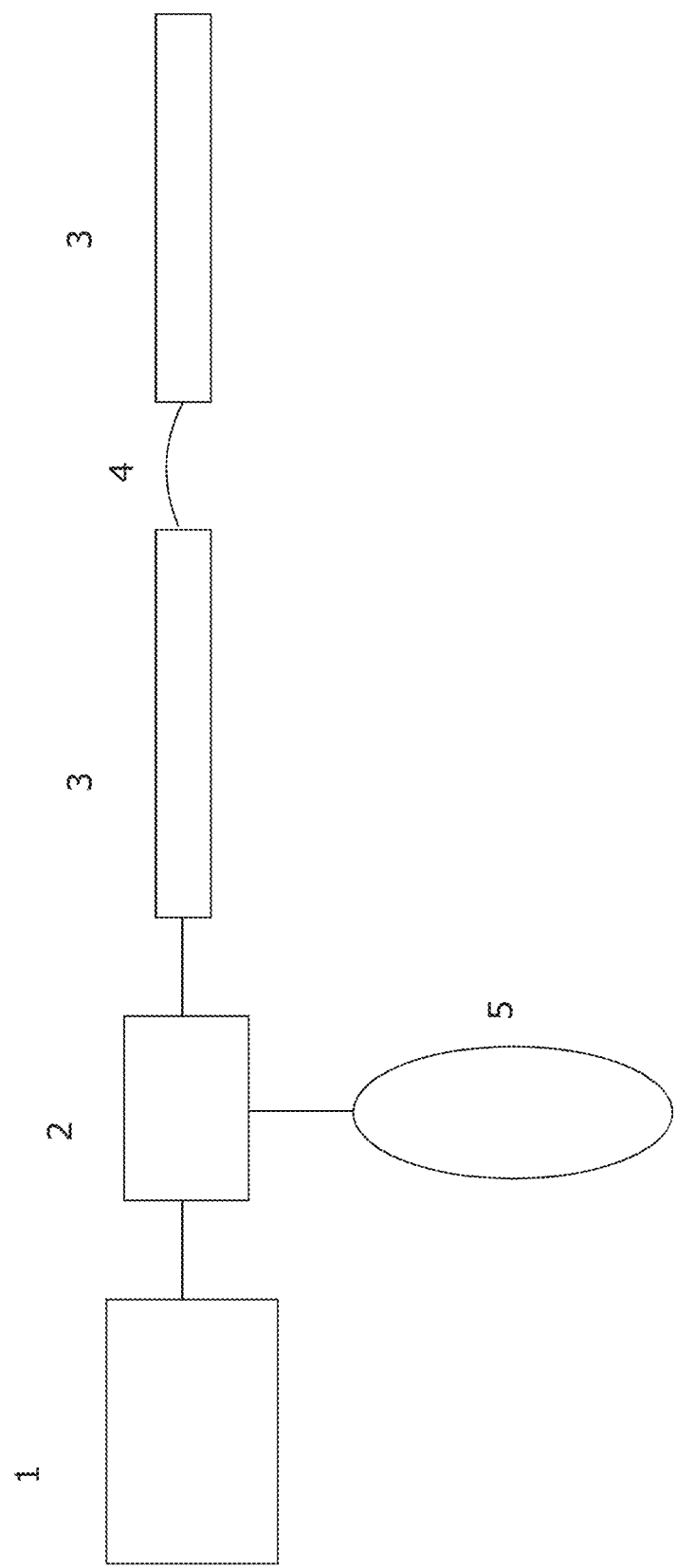
FIG. 1 is a schematic illustration of the polypeptide conjugate.

FIG. 1 shows a schematic drawing of a polypeptide conjugate with a moiety 1 and connected to a linker 2. A second moiety 5 may be linked to the linker 2. The linker is also linked to polypeptide sequence Gly-Tyr-Arg-Pro-Val-His-Asn-Ile-Arg-Gly-His-Trp-Ala-Pro-Gly 3 which may be connected to one or more polypeptides 3 by a spacer 4.

EXAMPLES

Example 1: Self-Assembly of Polypeptide Conjugate

Scrambled peptides and fluorescence-labelled peptides were designed and synthesized as shown in table 1. To investigate whether the polypeptide conjugate can self-assemble, Nanoparticle Tracking Analysis (NTA) technology was employed to detect the peptide aggregation. Briefly, 1 mL peptide solutions with different concentrations (0.5, 1, 2.5 and 5 μM) were prepared by diluting the peptide stock solutions (500 μM) with MQ water and incubate for 30 min at room temperature. NTA measurements were performed with a NanoSight LM20 (NanoSight Ltd., Amesbury, United Kingdom) equipped with a sample chamber with a 405 nm blue laser and a Viton fluoroelastomer O-ring. The peptide samples were injected in the sample chamber with sterile syringes (BD Discardit II, New Jersey, USA) until the liquid reached the tip of the nozzle. All measurements were performed at room temperature. For the pH effect of FAM-CGY peptide assembly, FAM-CGY stock solution (500 μM) was diluted into 5 μM with 10 mM HEPES buffer where pH values were adjusted with 1 M HCl or 1 M NaOH, respectively.

Figure 2:
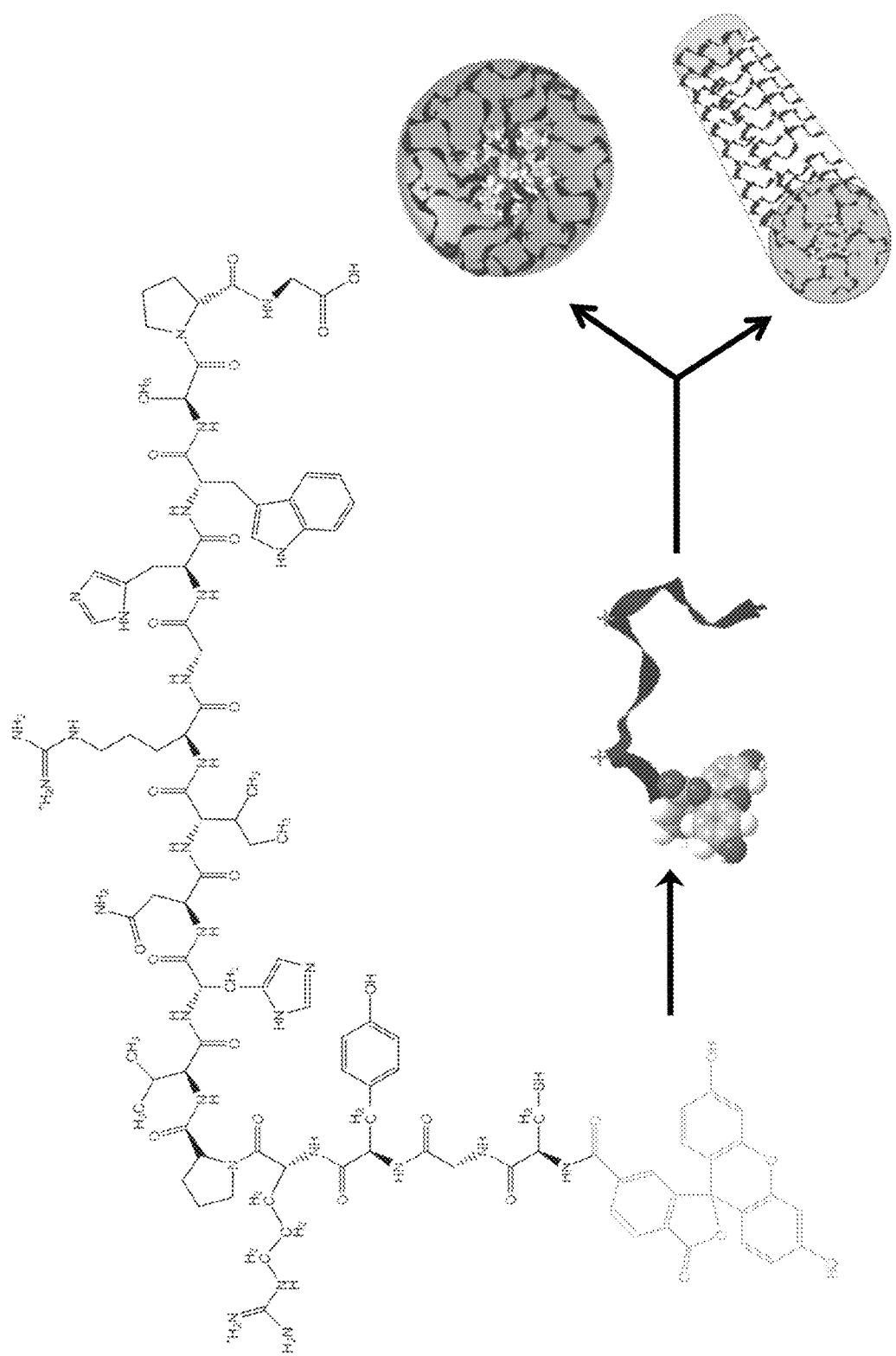
FIG. 2 is schematic illustration of a self-aggregation model of FAM-CGY nanoparticles using ChemBioOffice software where the polypeptide is linked to FAM. It is further illustrated how the peptide conjugate self-assemble into a nanoparticle or a fiber form through the formation of disulphide bridges, hydrogen bonding, possible salt-bridges and hydrophobic interaction including π-π interactions.
Figure 3A:
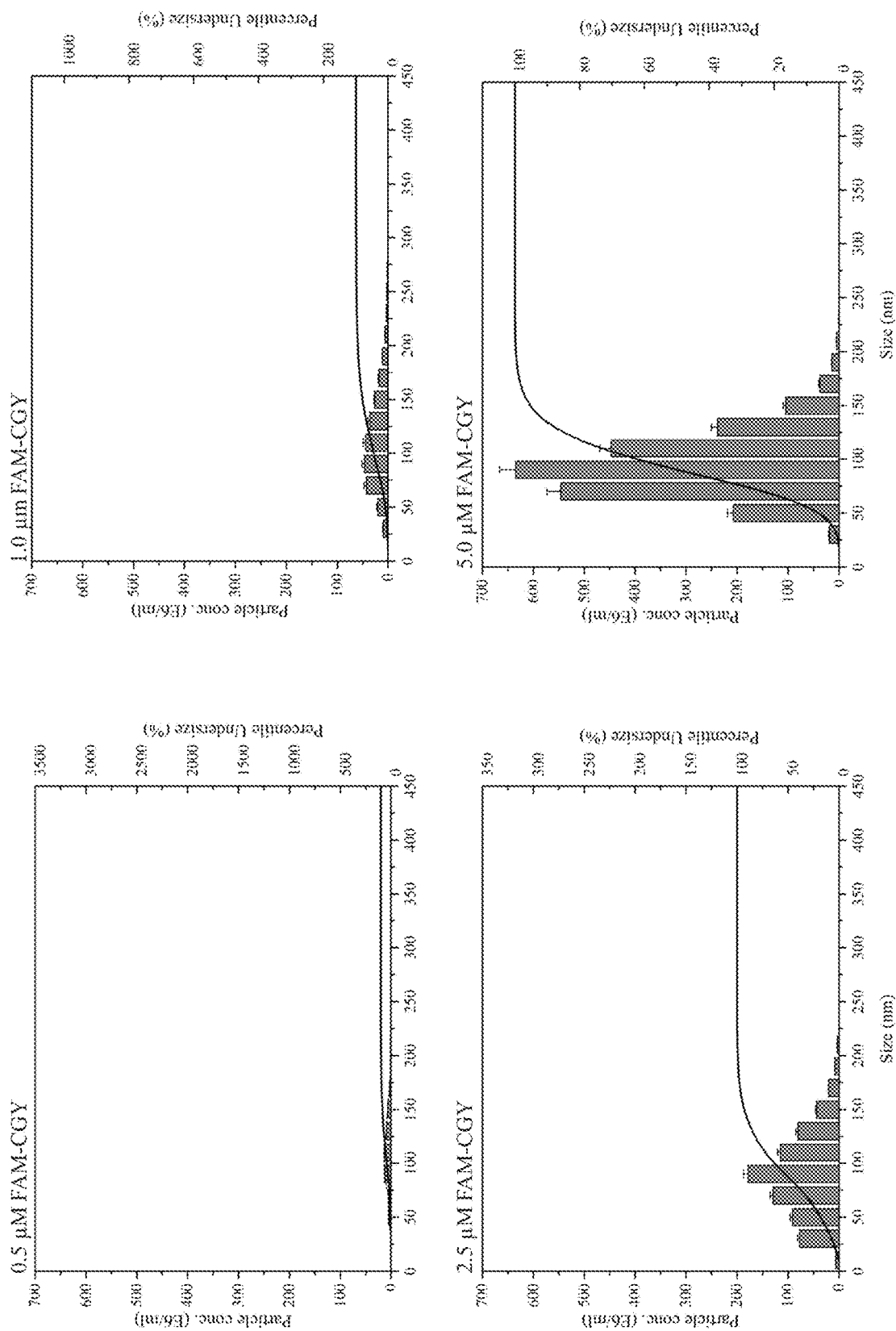
FIG. 3A represents nanoparticle size analysis by Nanosight Particle Tracking (NTA) of different concentrations of FAM-CGY peptide in MQ water. Corresponding representative NTA video frame is also shown (B). This is in accord with the critical aggregation concentration of FAM-CGY, which is 2.5 micromolar and shown in FIG. 6A.
Figure 3B:
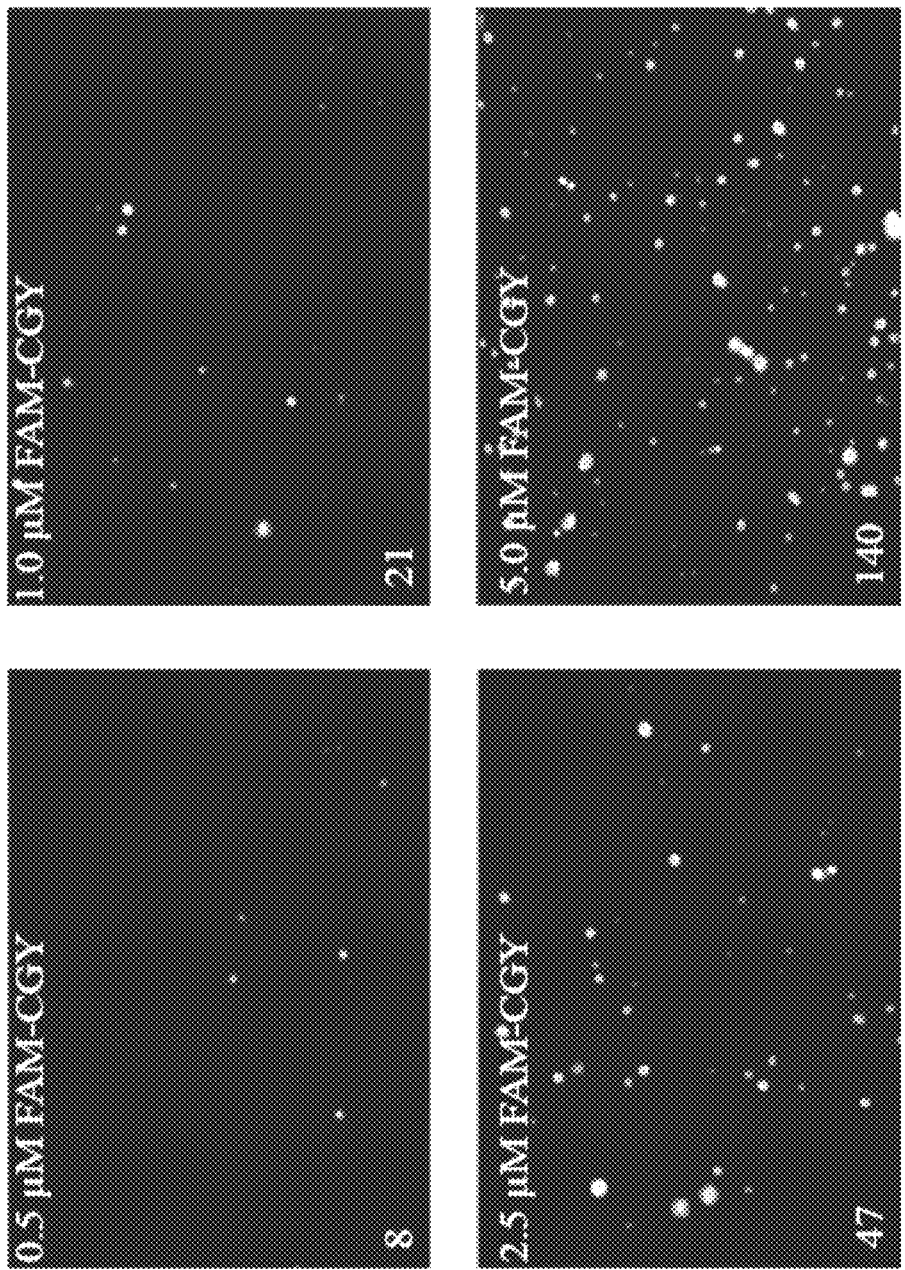
FIG. 3B shows representative NTA video frames of nanoparticle scattering from particle size analysis in FIG. 3A. The arabic numeral on the down-left corner of the video frame represent the count number of scattered particles within the analysed frame.
Figure 4:
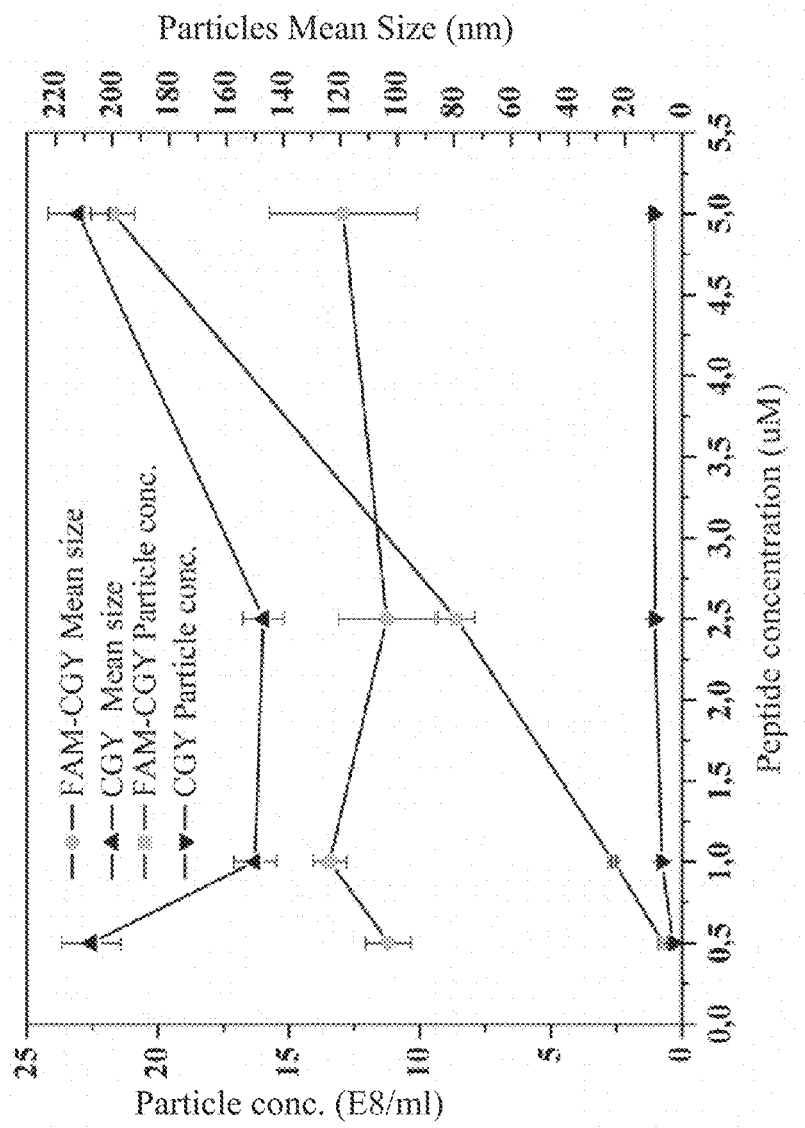
FIG. 4 is a graph showing the relation between the peptide concentration, particle concentration and size. The CGY-peptide is with and without FAM at the N-terminal.
Figure 5:
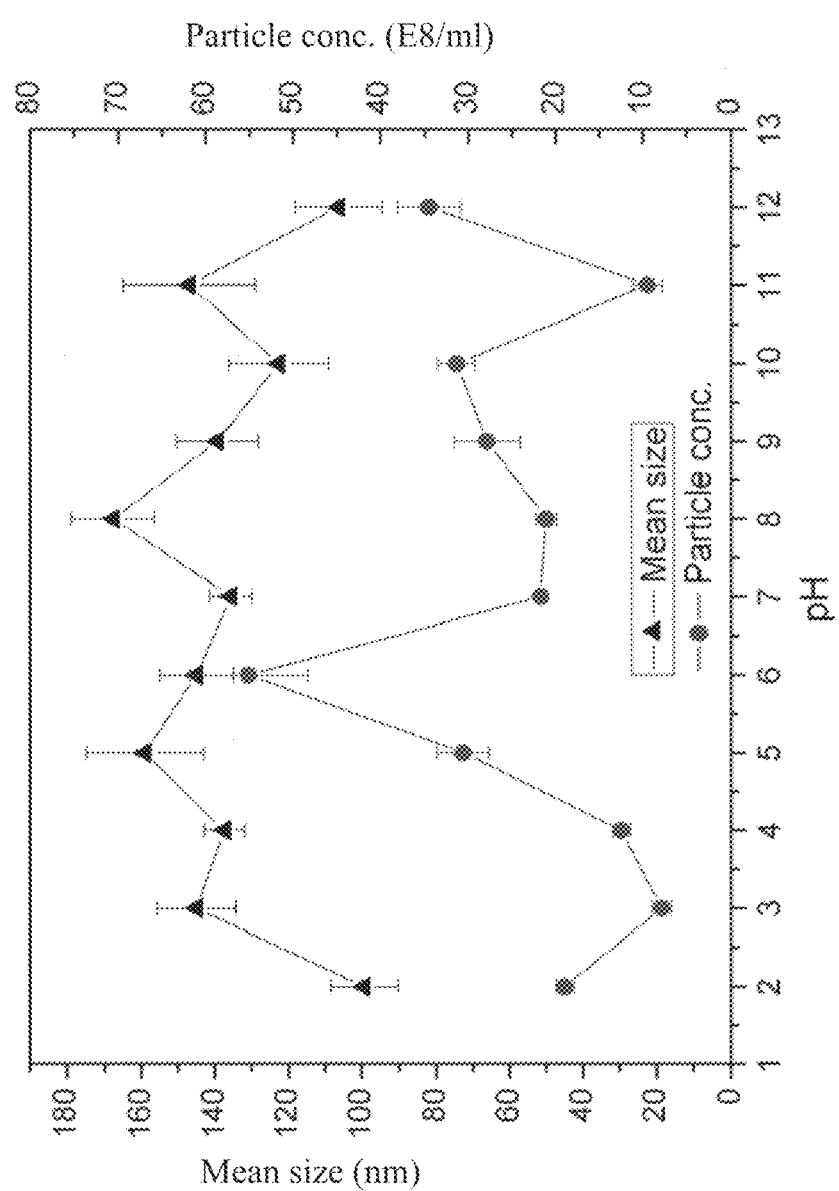
FIG. 5 is a graph showing the effect of pH on size and concentration of the FAM-CGY-peptide-aggregates. A 5 µM FAM-CGY peptide working solutions was prepared in 10 mM HEPES buffer, pH values were adjusted with 1M HCL or 1M NaOH.
Figure 6A:
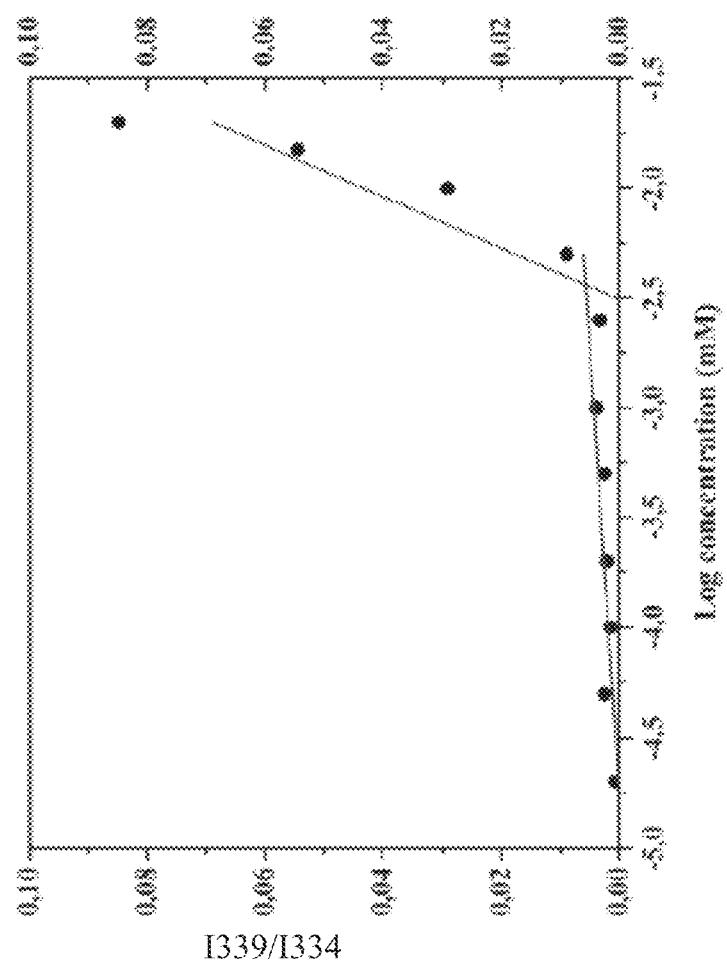
FIG. 6. Characterization of FAM-CGY peptidic nanoparticles FIG. 6A. critical aggregation concentration measurement, FIG. 6B. atomic force microscopy (AFM) representation of aggregated FAM-CGY peptides showing a network of globular and fibre structures, FIG. 6C. graph of particle size distribution measured by NTA, and FIG. 6D. far-UV CD spectra of FAM-CGY peptide at various pH.
Figure 6B:
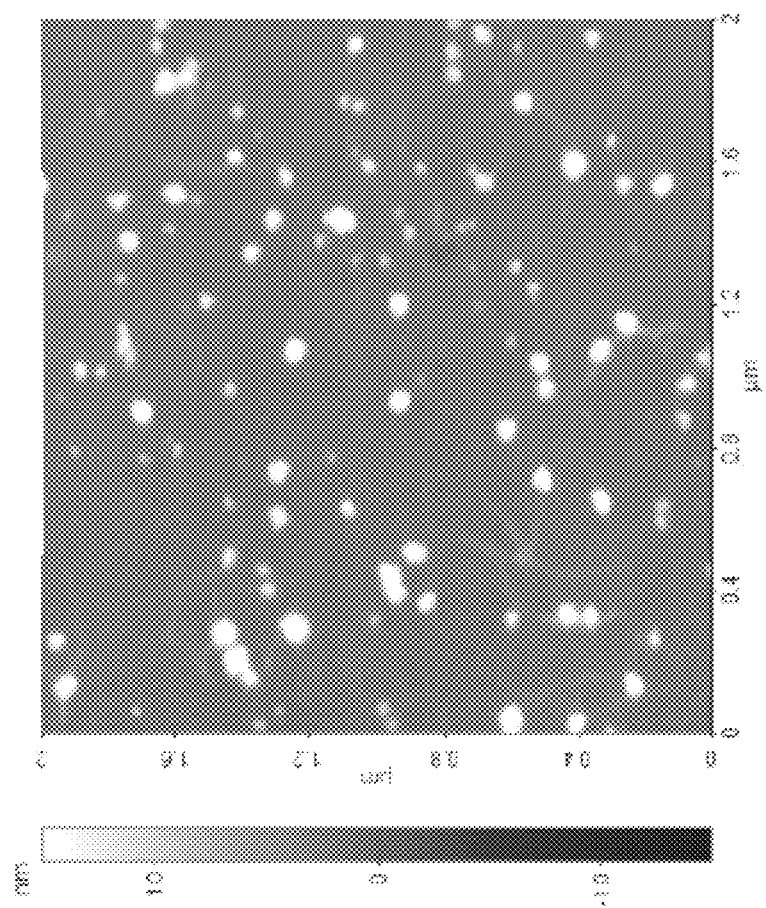
Figure 6C:
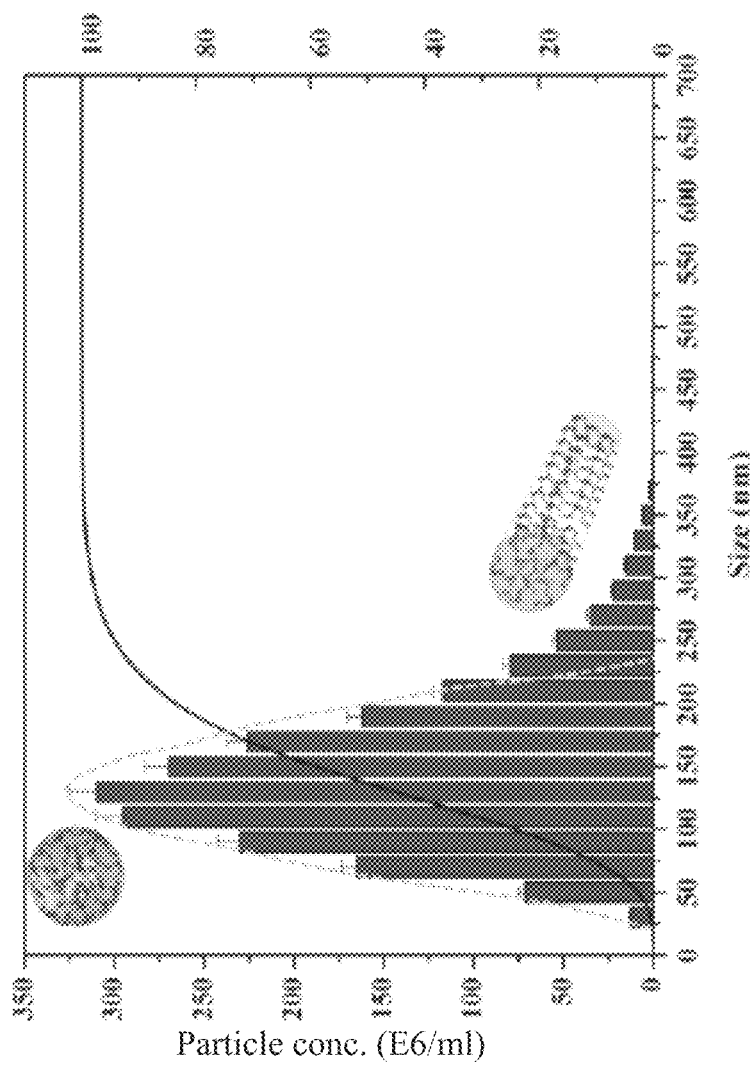
Figure 6D:
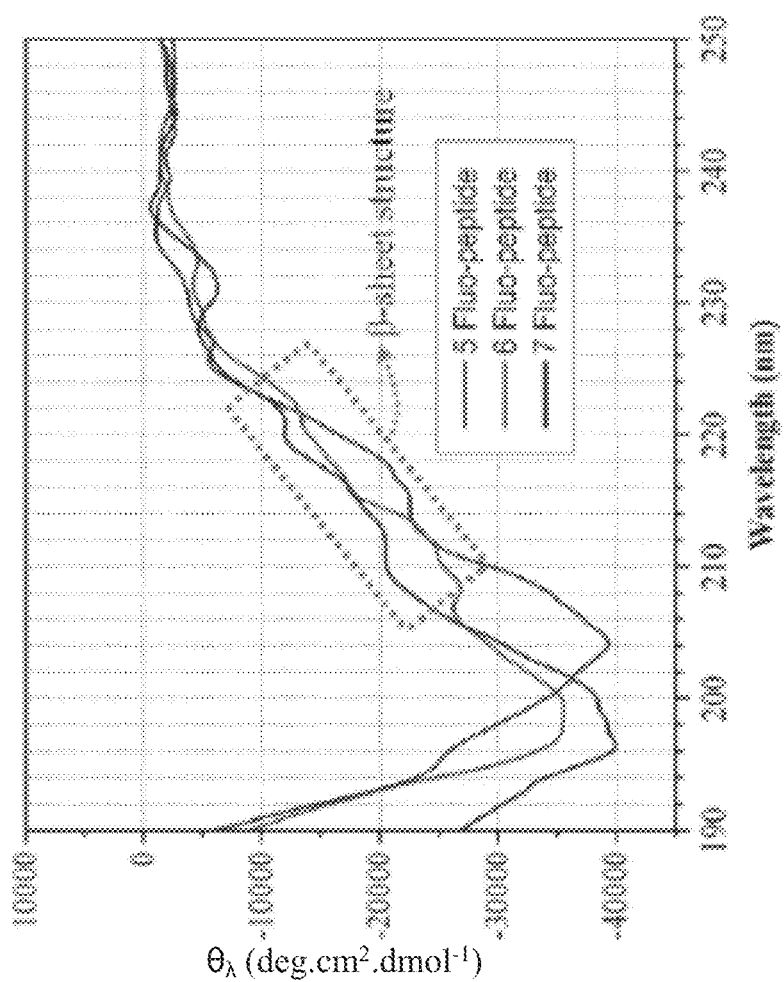

FAM-CGY self-assembles into nanoparticles and fibres as shown in FIG. 2. The size of the self-assembled FAM-CGY nanoparticles are 2-200 nm depending on the peptide conjugate concentration.

TABLE 1

| Peptide | Modified site | Peptide sequence | SEQ ID NO. | Molecular weight | Purity |
|---|---|---|---|---|---|
| CGY | Unlabel peptide | Cys-Gly-Tyr-Arg-Pro-Val-His-Asn-Ile-Arg-Gly-His-Trp-Ala-Pro-Gly | 3 | 1820.04 | 98.11% |
| FAM-CGY | Original peptide | 5-FAM-Cys-Gly-Tyr-Arg-Pro-Val-His-Asn-Ile-Arg-Gly-His-Trp-Ala-Pro-Gly | 4 | 2178.36 | 98.91% |
| CGY-FAM | 5-FAM C-terminal peptide, 5-FAM effect | Cys-Gly-Tyr-Arg-Pro-Val-His-Asn-Ile-Arg-Gly-His-Trp-Ala-Pro-Gly-Lys-5-FAM | 5 | 2305.53 | 98.36% |
| FAM-d-CGY | D form amino acid affect | 5-FAM-dCys-dGly-dTyr-dArg-dPro-dVal-dHis-dAsn-dIle-dArg-dGly-dHis-dTrp-dAla-dPro-dGly | 6 | 2177.36 | 98.34% |
| FAM-CGY Scrambled 1 | Change the position of Arg, the charge effect | 5-FAM-Cys-Gly-Tyr-Arg-Pro-Val-His-Asn-Ile-Gly-His-Trp-Arg-Ala-Pro-Gly | 7 | 2177.36 | 98.56% |
| FAM-CGY Scrambled 2 | Without Tryptophan, relative the Tryptophan effect | 5-FAM-Cys-Gly-Tyr-Arg-Pro-Val-His-Asn-Ile-Arg-Gly-His-Gly-Ala-Pro-Gly | 8 | 2048.20 | 98.26% |

Figure 15:
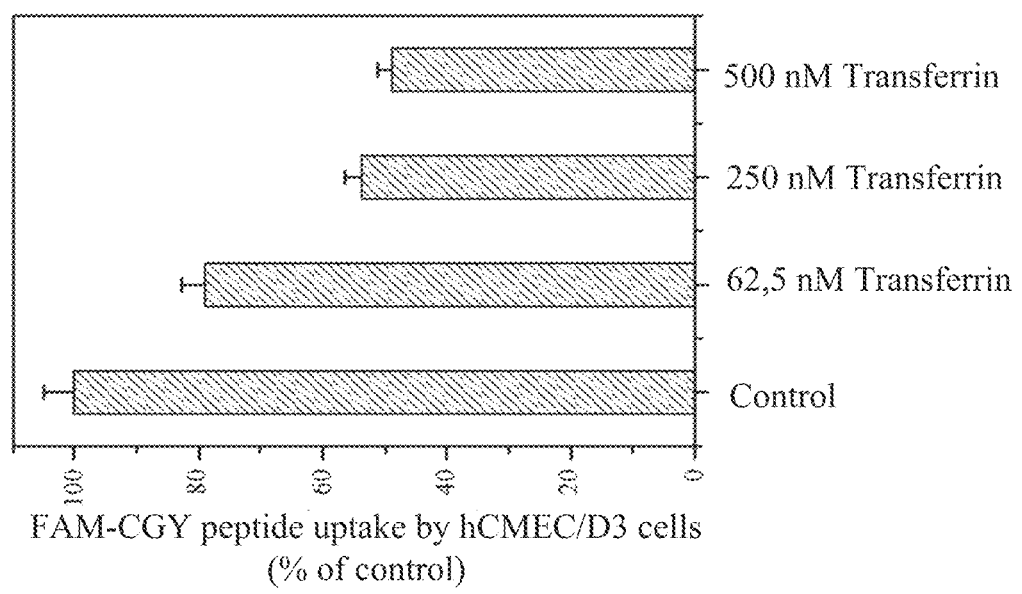
FIG. 15 is a chart showing the level of competition for TFRC binding of FAM-CGY nanoparticles and different concentrations of transferrin (62.5, 250 nM or 500 nM) analyzed by fluorescence microscopy (not shown) and quantified by FACS.

Example 2: Specific Binding to and Cellular Uptake of FAM-Labeled CGY-Peptide by hCMEC/D3 Cells To evaluate the role of the transferrin receptor in the uptake of FAM-CGY nanoparticles, hCMEC/D3 cells were incubated with both transferrin and FAM-CGY nanoparticles in competition experiment (FIG. 15).

The determination of fluorescence peptide internalization in hCMEC/D3 cells by flow cytometry (FACS) was performed as follows. Cells ($2 \times 10^4/cm^2$) were seeded on 24-well plate (Corning, N.Y.) and grown 2 days at 37° C. and 5% $CO_2$ in order to reach 60%-70% confluency. The cells were washed 3 times with pre-heated PBS and 200 μL of 5 μM fluorescence-labelled peptides (diluted in cell medium containing serum) was added. After 24 h of incubation at 37° C. with 5% $CO_2$, each chamber was washed with pre-heated PBS 3 times and incubated with fresh cell growth medium. The cell nucleus was stained with Hoechst 34580 dye (5 ug/mL), cell membrane was stained with Texas Red®-X wheat germ agglutinin (5 ug/mL). FAM-CGY nanoparticles competed with different concentrations of transferrin or added with the peptides in different concentrations ranging from 62.5-500 nM and were analyzed by fluorescence microscopy and quantified by FACS.

The live cell imaging was performed on a widefield microscope (Leica AF6000LX, Germany) using a 63× oil objective with 1.6 magnification and filters GFP (Ex BP 470/40, Em BP 525/50), Cy3 (Ex BP 555/25, Em BP 605/52) and A4 (Ex BP 360/40, Em 470/40). Treated cells were then washed 3 times with pre-warmed PBS, and harvested by trypsinization. A total of 10,000 cells were analyzed by flow cytometry (FACS Array™ Cell Analysis, BD, USA).

The competition experiment shows that the uptake of the FAM-CGY nanoparticles is significantly decreased with increasing transferrin concentration suggesting that FAM-CGY nanoparticles strongly compete with transferrin on binding to the transferrin receptor.

Figure 17H:
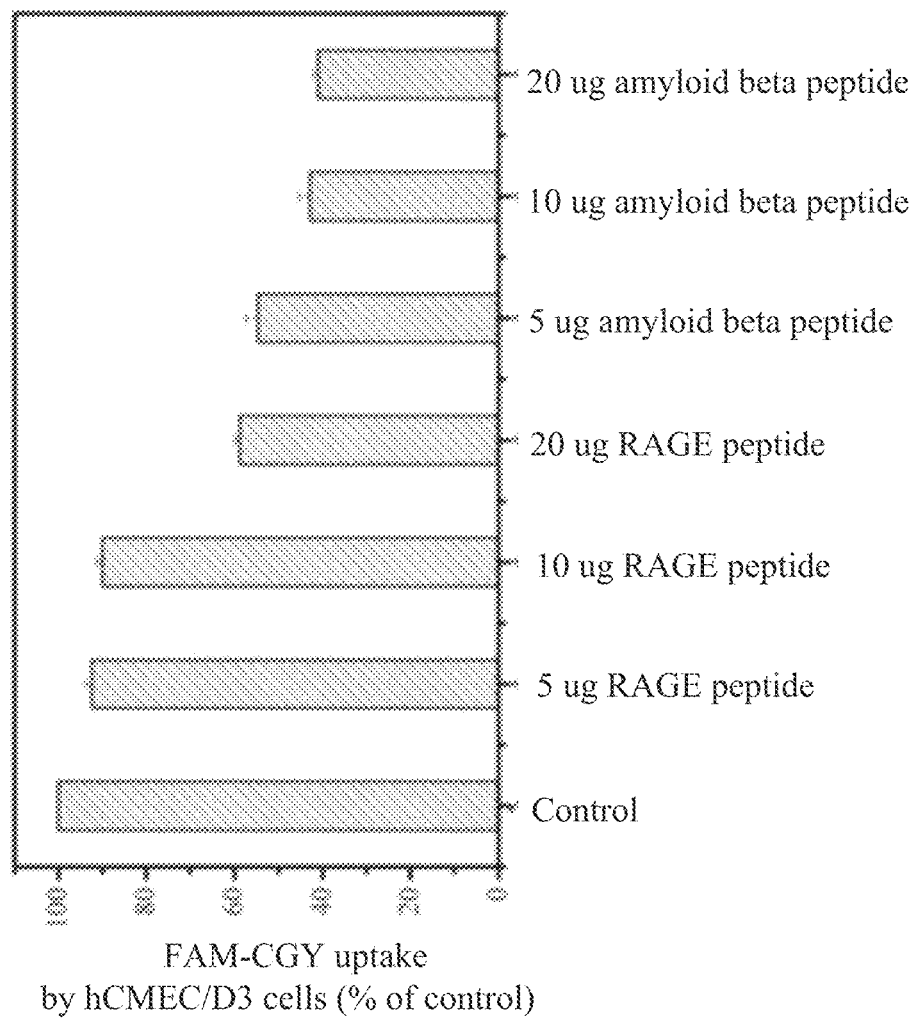
FIG. 17H is quantified by FACS.

Example 3: Specific Binding and Cellular Uptake of FAM-Labeled CGY-Peptide to hCMEC/D3 Cells To evaluate the role of the RAGE in the uptake of FAM-CGY nanoparticles, hCMEC/D3 cells were co-treated with RAGE-peptide or amyloid-ß and FAM-CGY nanoparticles in competition experiments (FIG. 17).

The determination of fluorescence peptide internalization in hCMEC/D3 cells by flow cytometry (FACS) was performed as follows. Cells ($2\times10^4$/cm$^2$) were seeded on 24-well plate (Corning, N.Y.) and grown 2 days at 37° C. and 5% $CO_2$ in order to reach 60%-70% confluency. The cells were washed 3 times with pre-heated PBS and 200 µL of 5 µM fluorescence-labelled peptides (diluted in cell medium containing serum) was added. After 24 h of incubation at 37° C. with 5% $CO_2$, each chamber was washed with pre-heated PBS 3 times and incubated with fresh cell growth medium. The cell nucleus was stained with Hoechst 34580 dye (5 ug/mL), cell membrane was stained with Texas Red®-X wheat germ agglutinin (5 ug/mL). FAM-CGY nanoparticles (5 µM) competed with different amounts of RAGE-peptide or amyloid-ß peptide (5, 10 or 20 µg) and were analyzed by fluorescence microscopy (data not shown) and quantified by FACS (FIG. 17).

The live cell imaging was performed on a widefield microscope (Leica AF6000LX, Germany) using a 63× oil objective with 1.6 magnification and filters GFP (Ex BP 470/40, Em BP 525/50), Cy3 (Ex BP 555/25, Em BP 605/52) and A4 (Ex BP 360/40, Em 470/40). Treated cells were then washed 3 times with pre-warmed PBS, and harvested by trypsinization. A total of 10,000 cells were analyzed by flow cytometry (FACS Array™ Cell Analysis, BD, USA).

The competition experiment shows that the uptake of the FAM-CGY nanoparticles is significantly decreased with increasing RAGE-peptide or amyloid-ß concentration suggesting that FAM-CGY nanoparticles strongly compete with the RAGE-peptide and amyloid-ß on binding to the RAGE receptor.

Example 4: TFRC Gene Knock-Out Experiments

Figure 16A:
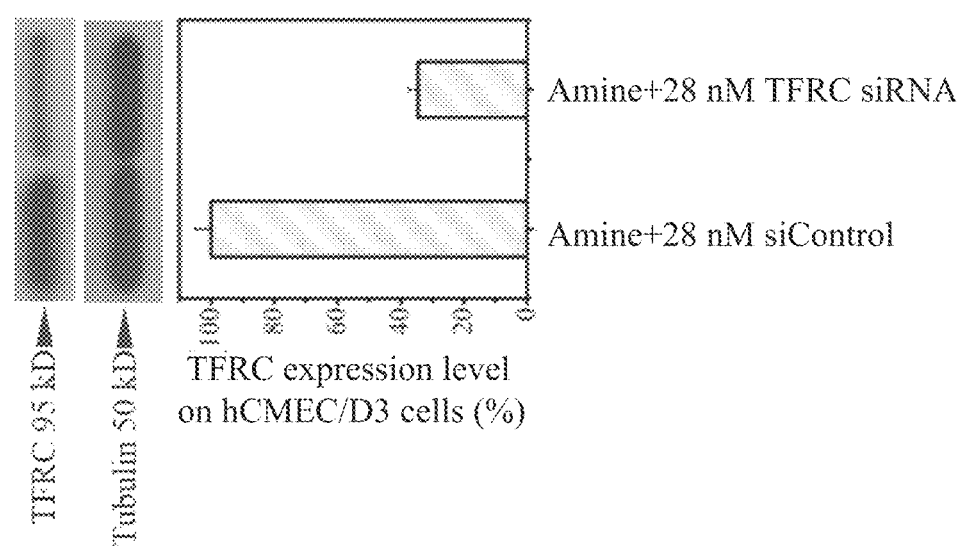
FIGS. 16A and 16B show blockage of FAM-CGY nanoparticle uptake after knocking down the TFRC expression.
Figure 16B:
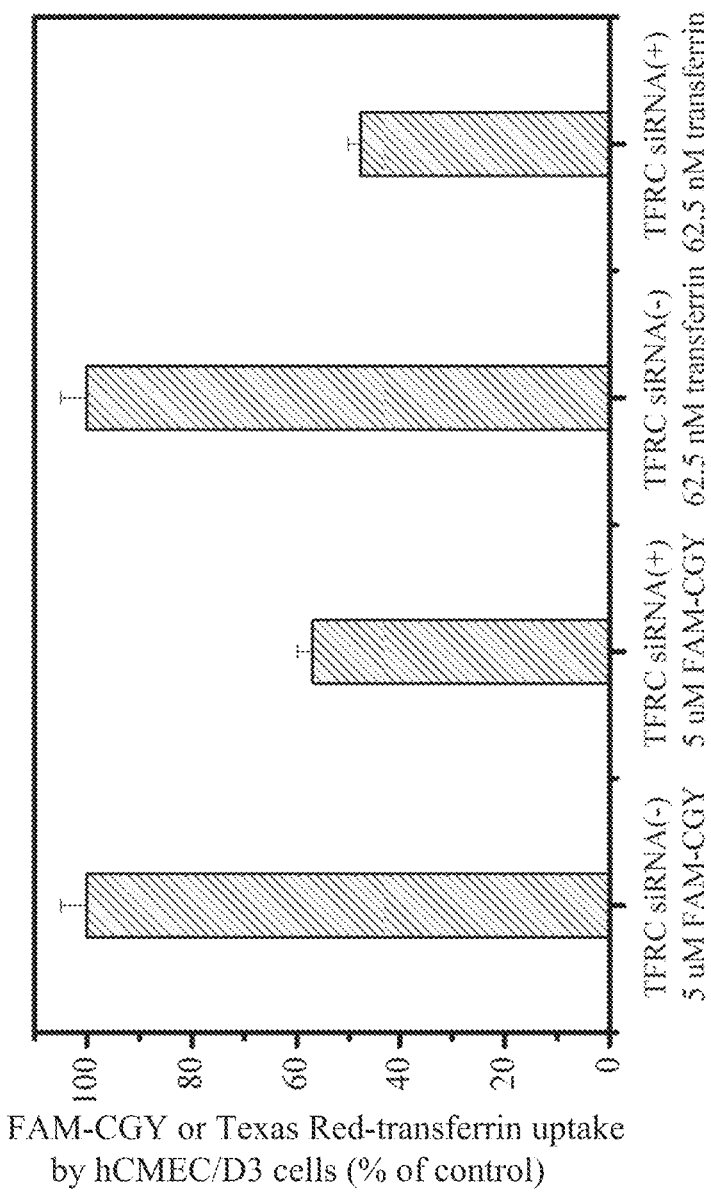

The transferrin receptor (TFRC) expression was down-regulated by using a commercial transfection reagent siPORT Amine/TFRC siRNA complex to study the possible blockage of the FAM-CGY nanoparticle uptake in hCMEC/D3 cells. The commercial transfection reagent siPORT Amine/TFRC siRNA complex was incubated for 72 h in hCMEC/D3 cells including an unspecific siRNA (siControl) as control. The TFRC low expression cells and siControl transfection cells were incubated with 5 µM FAM-CGY nanoparticles and 62.5 nM transferrin (positive control) for 16 h, respectively. The FAM-CGY nanoparticles and transferrin uptake was detected by fluorescence microscopy (not shown) and FACS (FIG. 16).

FAM-CGY nanoparticle uptake is markedly reduced in TFRC knocked out hCMC/DE3 cells to nearly the same level the as transferrin uptake. Hence, TFRC functions as a receptor for FAM-CGY nanoparticle binding and uptake.

Example 5: RAGE Gene Knock-Out Experiments

Figure 18A:
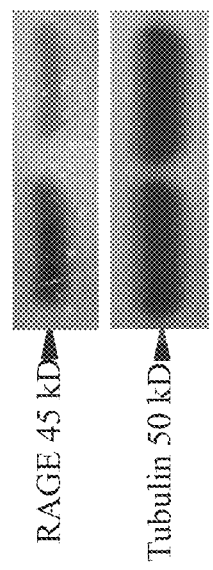
FIG. 18A shows downregulated RAGE expression using a commercial transfection reagent siPORT Amine/RAGE siRNA complex for 72 h in hCMEC/D3 cells and the unspecific siRNA (siControl) as control.
Figure 18B:
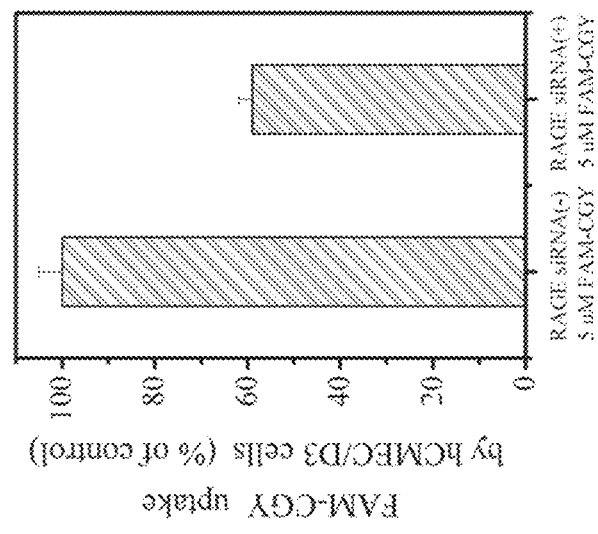
FIG. 18B shows blockage of the FAM-CGY nanoparticle uptake in RAGE knocked down hCMEC/D3 cells. The RAGE low expression cells and siControl transfection cells were incubated with 5 µM FAM-CGY nanoparticles and 250 nM amyloid-β peptide (positive control) for 16 h respectively, the FAM-CGY nanoparticles and amyloid-β peptide uptake was detected by fluorescence microscopy (not shown).
Figure 19A:
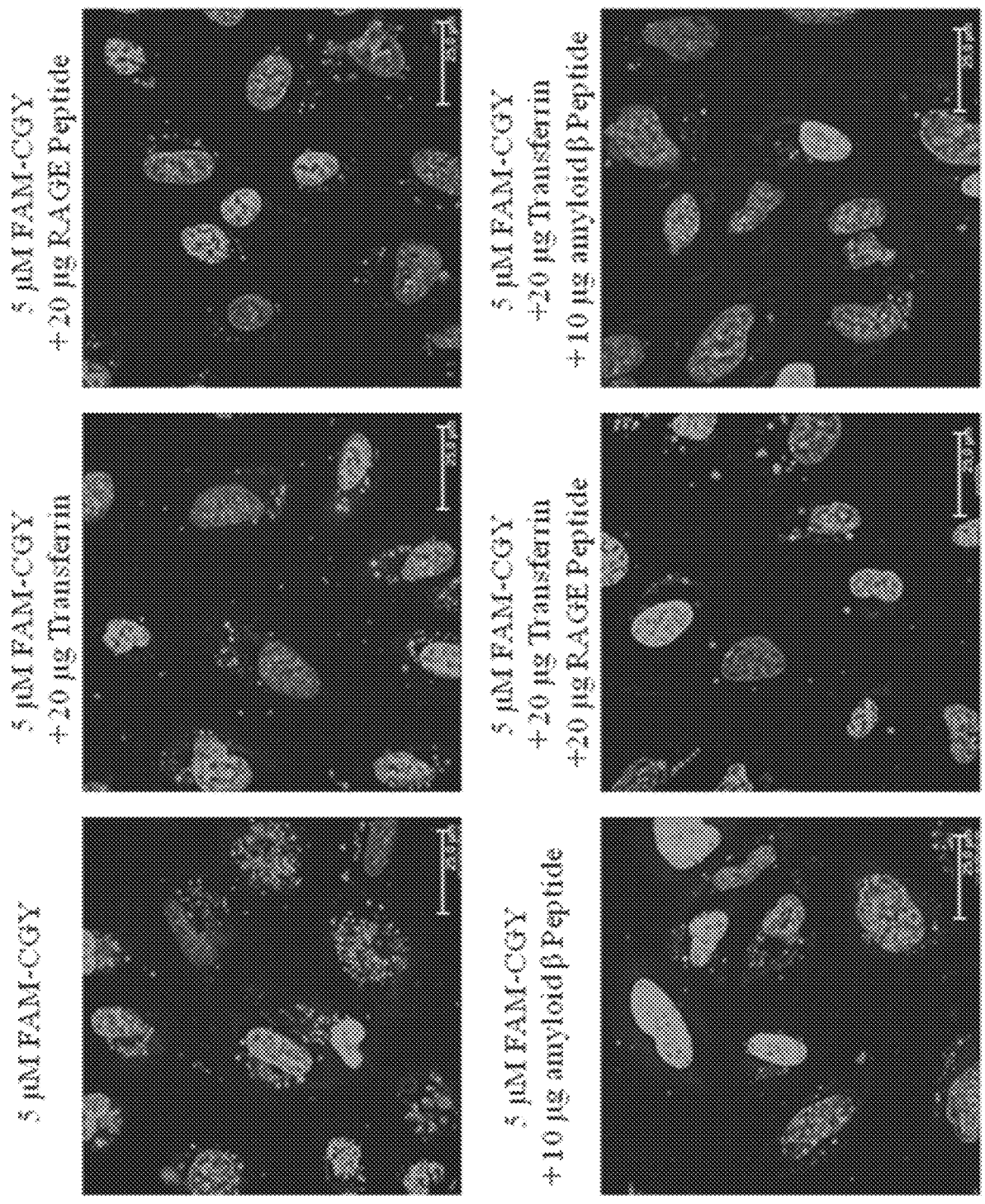
FIGS. 19A through 19C show FAM-CGY nanoparticles co-competed with transferrin, RAGE peptide or amyloid-β peptide.
Figure 19B:
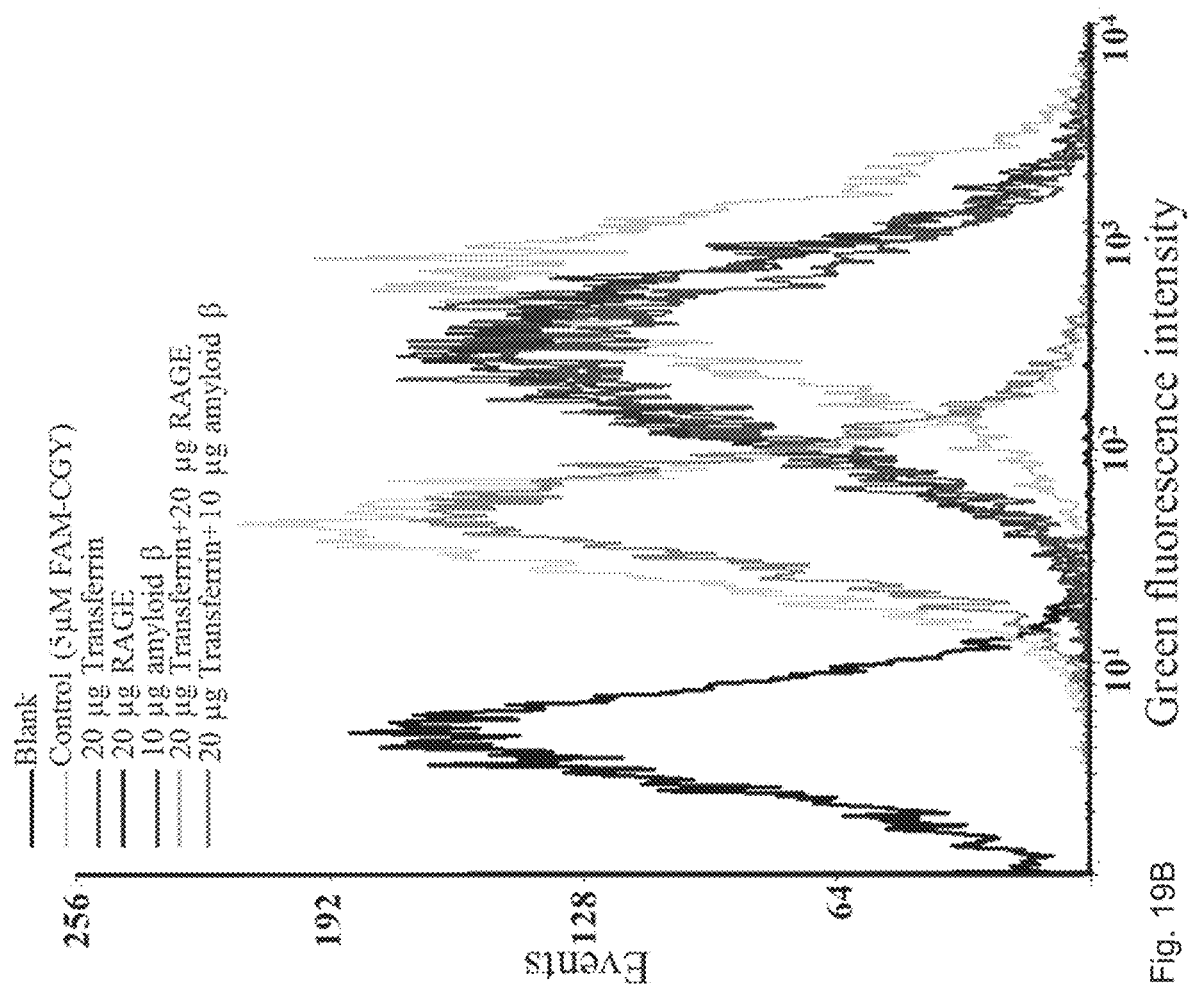
Figure 19C:
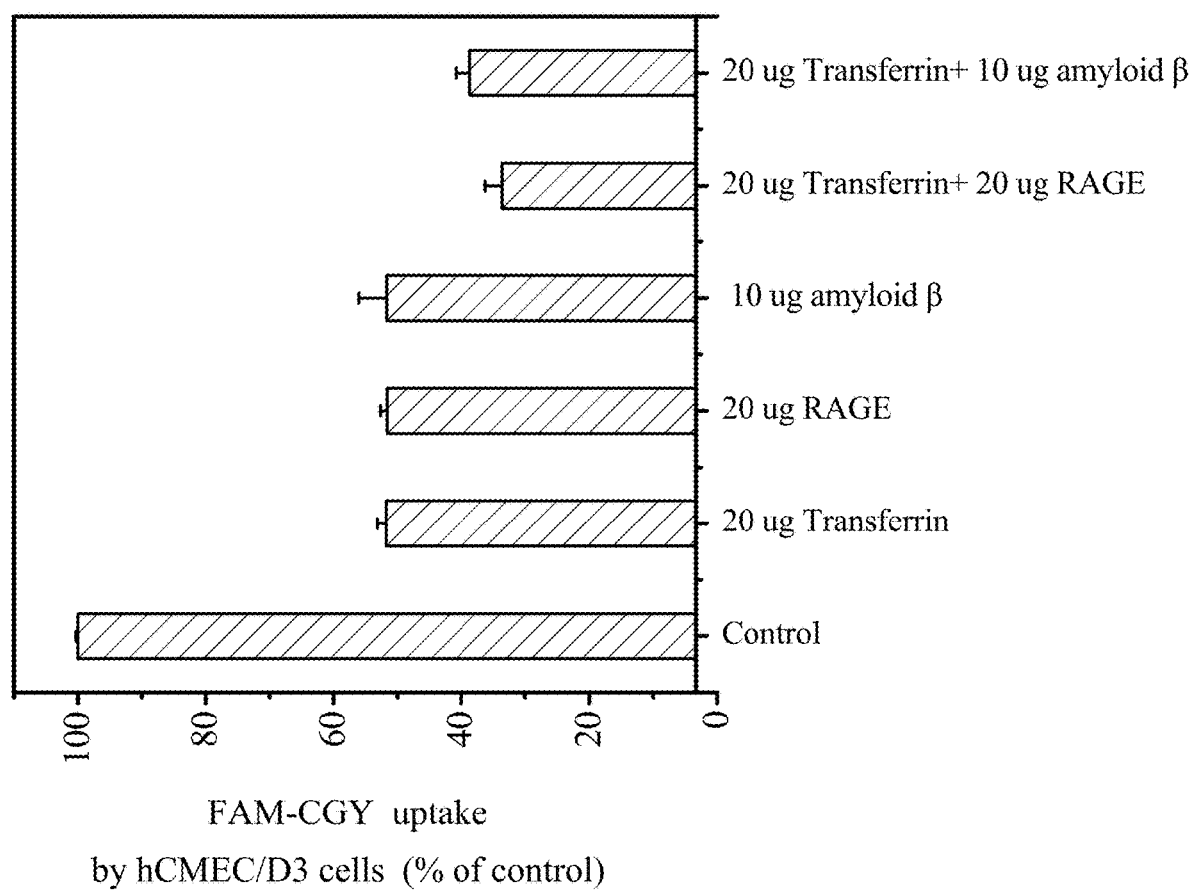
Figure 20:
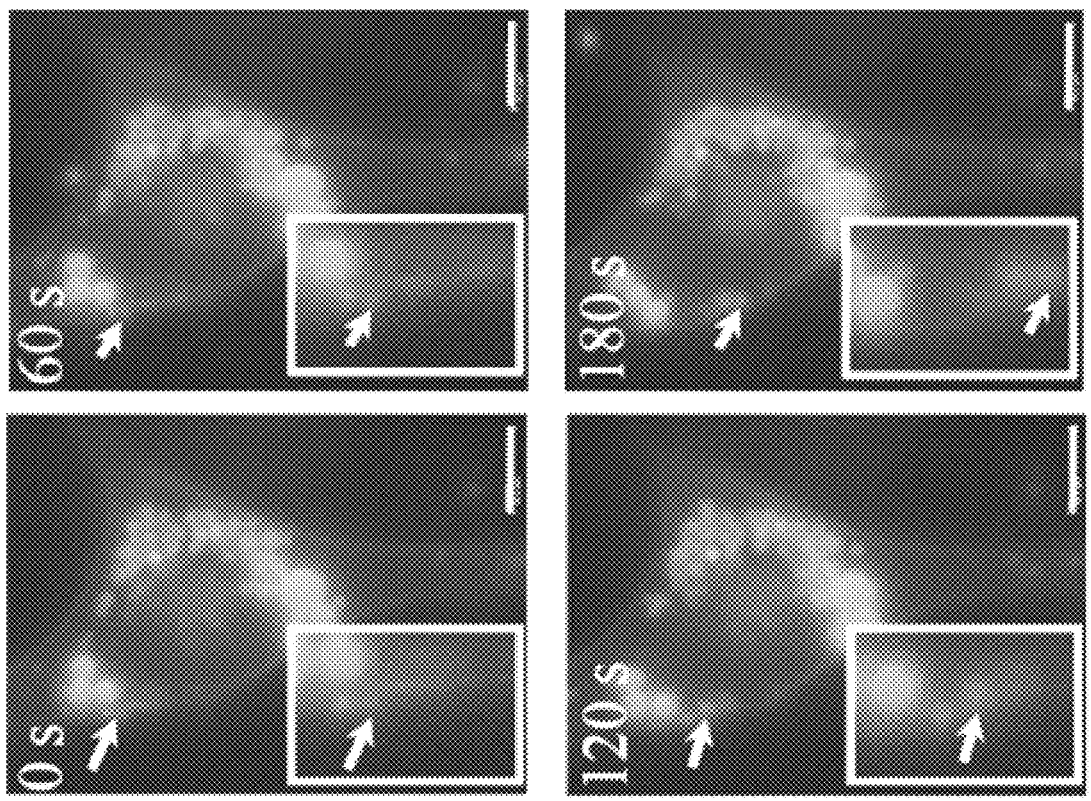
FIG. 20 Real-time trafficking FAM-CGY nanoparticles endocytosis. hCMEC/D3 cells were stained with wheat germ agglutinin (WGA)-Texas Red®-X and Hoechest 33342. Insert white frames are image amplifications. The arrows indicate the peptidic nanoparticles binding to the membrane of the cell surface or having just crossed the cell membrane. Insert bars=10 µm.
Figure 21:
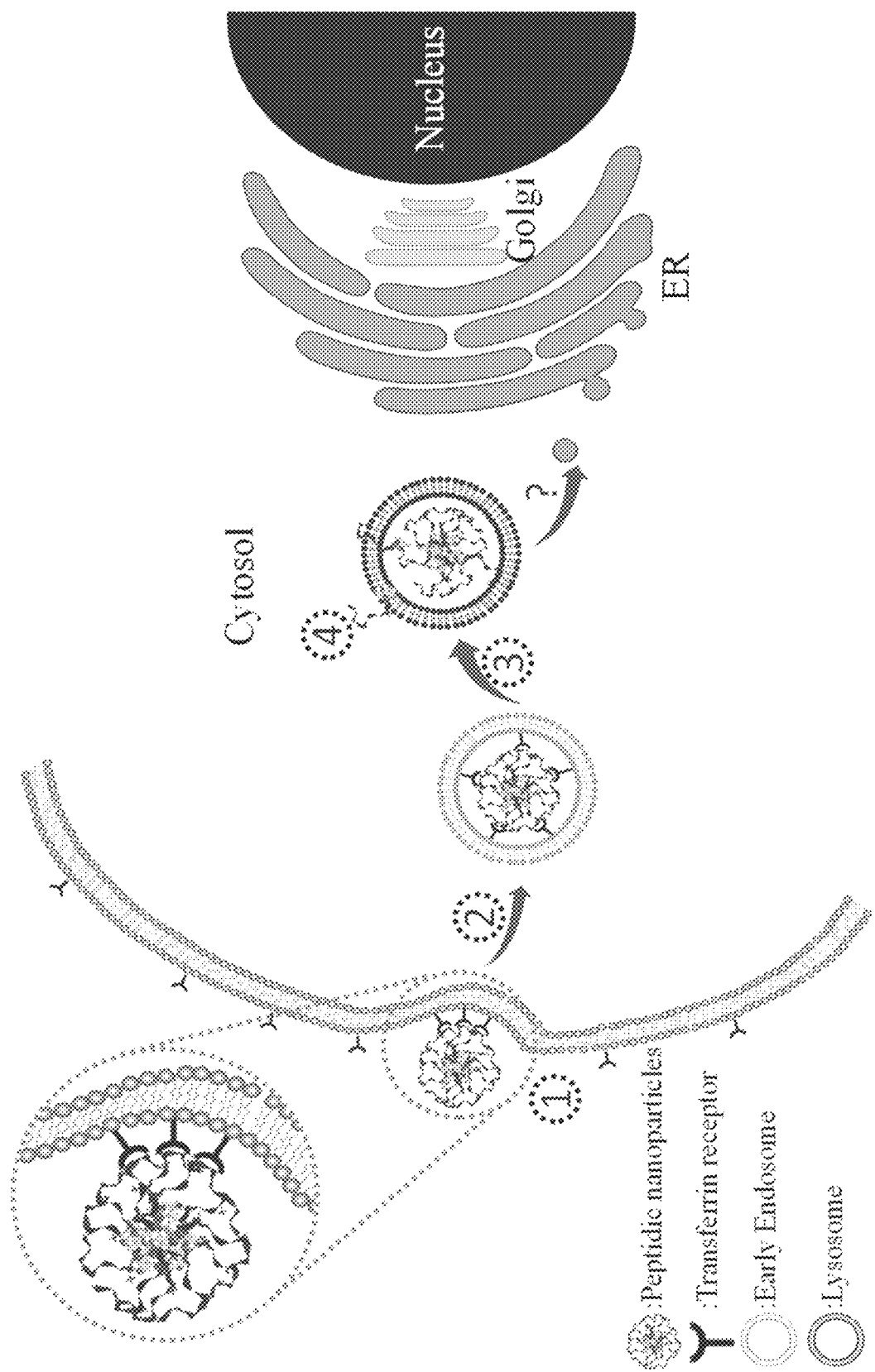
FIG. 21 Schematic illustration of the internalization mechanism of the FAM-CGY nanoparticles in hCMEC/D3 cell based on fluorescence microscopy experiments using CellLight® Early endosomes-RFP, Lysosomes-RFP, Golgi-RFP, and Endoplasmic reticulum (ER)-RFP to stain the cell organelles (not shown). Peptidic nanoparticle binds 1 to the cell surface with high affinity. After being internalized by transferrin receptor-mediated endocytosis 2 in early endosomes, the peptidic nanoparticles were transported from the early endosomes to the lysosomes and then released 4 into the cytosol. Experiments were unclear if peptidic nanoparticles were transported within the ER and Golgi apparatus.

The RAGE expression was downregulated by using a commercial transfection reagent siPORT Amine/RAGE siRNA complex to study the possible blockage of the FAM-CGY nanoparticle uptake in hCMEC/D3 cells. The commercial transfection reagent siPORT Amine/RAGE siRNA complex was incubated for 72 h in hCMEC/D3 cells including an unspecific siRNA (siControl) as control. The TFRC low expression cells and siControl transfection cells were incubated with 5 µM FAM-CGY nanoparticles and 250 nM amyloid-ß (positive control) for 16 h, respectively. The FAM-CGY nanoparticles and RAGE peptide uptake was detected by fluorescence microscopy (not shown) and FACS (FIG. 18).

FAM-CGY nanoparticle uptake is markedly reduced in RAGE knocked out hCMC/DE3 cells to nearly the same level as amyloid-ß uptake. Hence, RAGE functions as a receptor for FAM-CGY nanoparticles.

Example 6: Formation of siRNA/FAM-CGY Complex

Figure 22A:
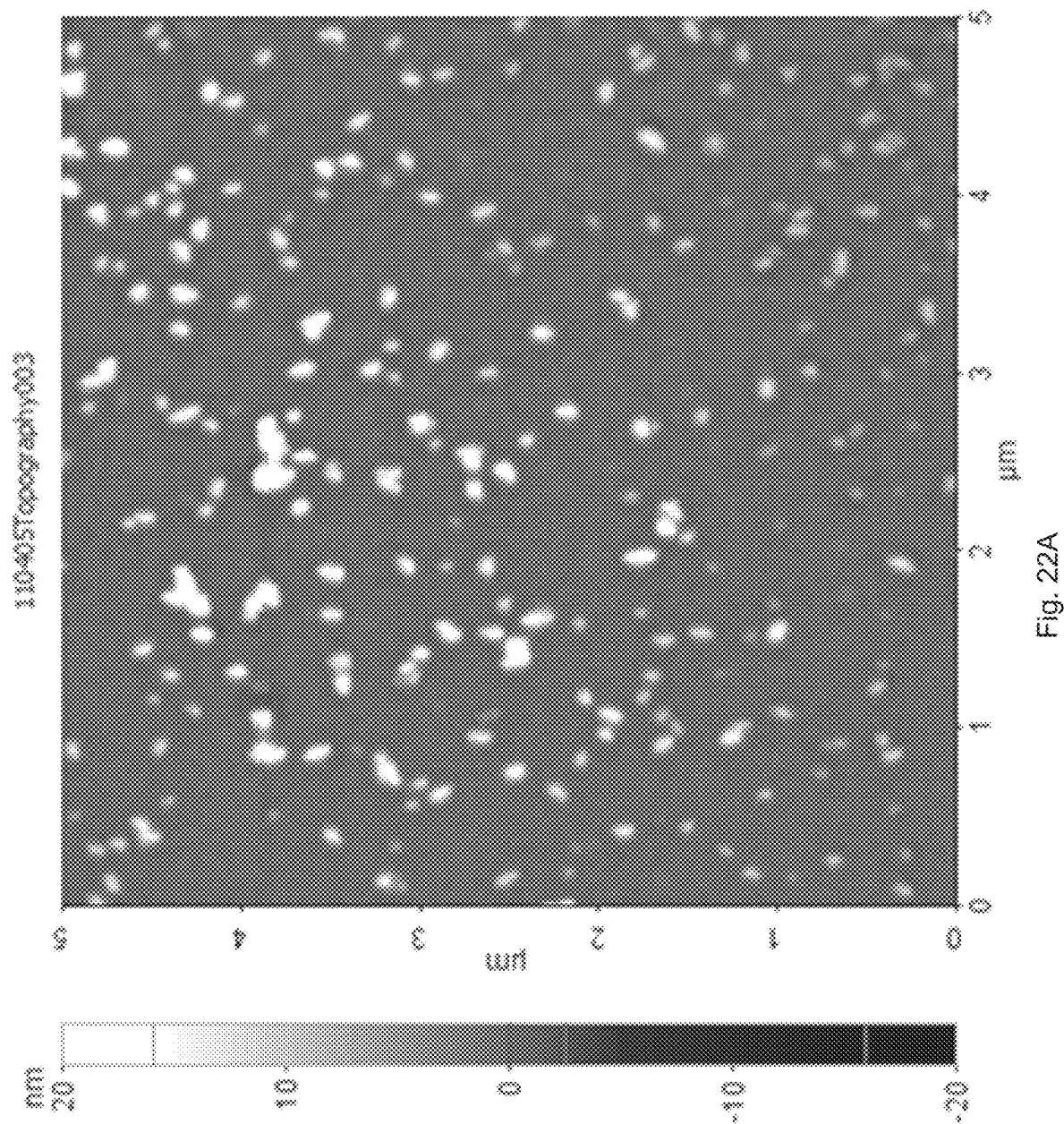
FIGS. 22A and 22B are characterizations of siRNA/FAM-CGY complexes.
Figure 22B:
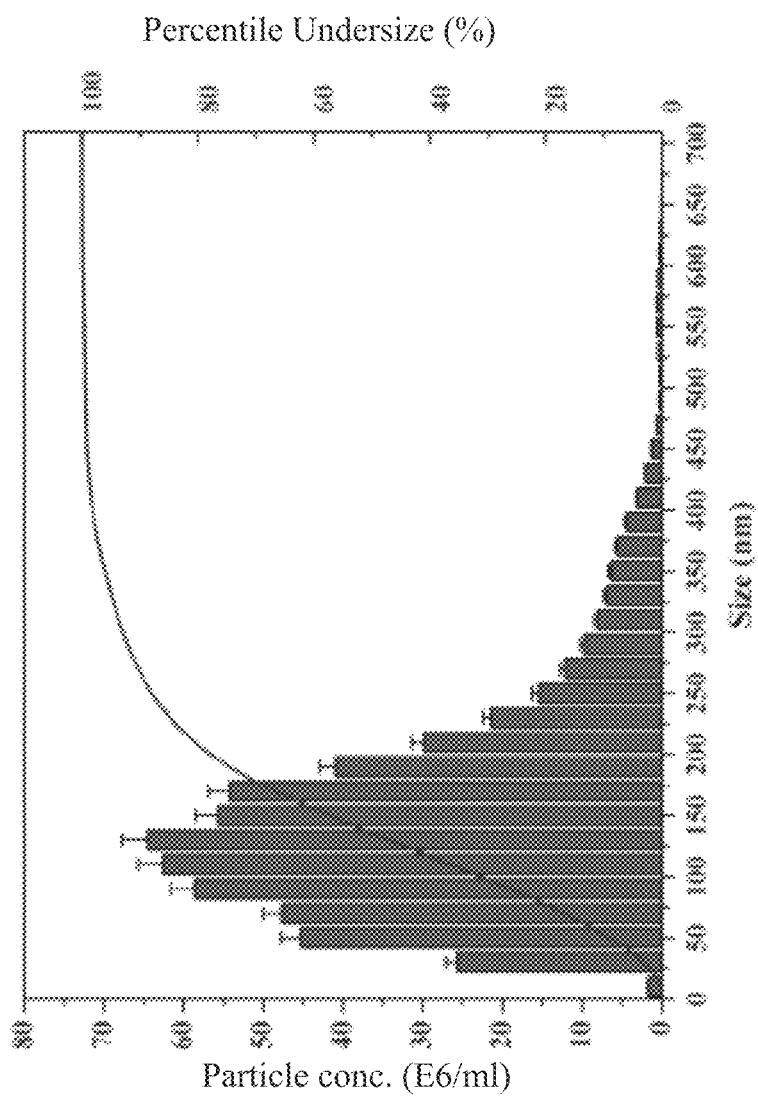

Different molar rates of siRNA were added to the FAM-CGY peptide solution (50 µM/L) dropwise in saline solution and incubated for 30 min. Then the mixture solution was diluted with serum free hCMEC/D3 cell medium to a final peptide concentration 5 µM. The atomic force microscopy (AFM) (FIG. 22a), nanoparticle tracking analysis (NTA) (FIG. 22b), fluorescence microscopy (not shown), dynamic light scattering (DLS) technology (not shown) and transmission electron microscopy (TEM) (FIG. 23) were employed to characterize the siRNA/FAM-CGY complex. Complexes with circular RNA (ciRNA) and FAM-CGY was also studied using TEM (FIG. 24). Briefly, one drop of the final Cy3-siRNA/FAM-CGY solution was added on microscope glass slides (VWR) and left to air-dry at room temperature for 30 min. The Cy3-siRNA/FAM-CGY complexes were imaged by fluorescent microscopy (Leica AF6000LX, Germany) using a 100×TIRF oil objective with 1.6 magnification and filters GFP (Ex BP 470/40, Em BP 525/50), and Cy3 (Ex BP 555/25, Em BP 605/52). The size and surface charge of FAM-CGY peptidic nanoparticles and siRNA/FAM-CGY complex were investigated using a Zetasizer Nano ZS goniometer (Malvern Instruments, Malvern, UK) containing a He—Ne laser source (A=633 nm, 22 mW output power). All the measurements were carried out at 25° C. Three measurements each with 30 sub-runs were performed for each sample and results are shown in Table 2.

FAM-CGY forms stable spherical and rod shaped nanoparticles with siRNA having average diameter of 168±12 nm for spherical particles analyzed by NTA and for fibres a length of 297±87 nm analysed by TEM 23), which is slightly larger than FAM-CGY nanoparticles described above. These results are similar to dynamic light scattering (DLS) characterization, where the siRNA/FAM-CGY particles are in the size range of 170-180 nm and display a slightly positive surface charge with zeta potentials ranging from 5.57±0.87 to 1.27±0.38 mV.

TABLE 2

The size and zeta potential of FAM-CGY nanopaticles and siRNA/FAM-CGY complexes characterized by dynamic light scattering (DLS).

| Samples | Size (nm) | PDI | Zeta potential (mV) |
|---|---|---|---|
| 5 µM FAM-CGY nanopartilces | 156.6 ± 2.1 | 0.325 ± 0.028 | 7.27 ± 0.73 |
| 8 nM siRNA/5 µM FAM-CGY complex | 170.2 ± 5.3 | 0.380 ± 0.033 | 5.57 ± 0.87 |
| 16 nM siRNA/5 µM FAM-CGY complex | 173.8 ± 3.2 | 0.402 ± 0.047 | 2.87 ± 0.50 |
| 24 nM siRNA/5 µM FAM-CGY complex | 180.6 ± 12.1 | 0.397 ± 0.054 | 1.27 ± 0.38 |

Example 7: Transfection of hCMC/DE3 Cells with Cy3-siRNA/FAM-CGY Complex

To confirm the rate of cellular transfection, different molar ratios of Cy3-fluorescence labeled siRNA (Cy3-siRNA) were incubated with FAM-CGY peptide to form polyplexes, and added to hCMEC/D3 cells (data not shown). Different molar rates of Cy3-siRNA were added to FAM-CGY peptide dropwise in saline solution and incubated for 30 min. Then the mixture solution was diluted with normal hCMEC/D3 cells medium to a final concentration of FAM-CGY peptide 5 µM (5000 nM). The cells were incubated with different rates of Cy3-siRNA/FAM-CGY complex as indicated at 37° C. for 24 h. The cell nucleus was labelled with Hoechst 33342 (blue), insert bars=50 µm.

The Cy3-siRNA/FAM-CGY complex exhibits significant cellular uptake by hCMEC/D3 cells in all molar ratios compared to Cy3-siRNA alone.

Example 8: Transfection of hCMC/DE3 Cells with Cy3-siRNA/FAM-CGY Complex

Figure 23:
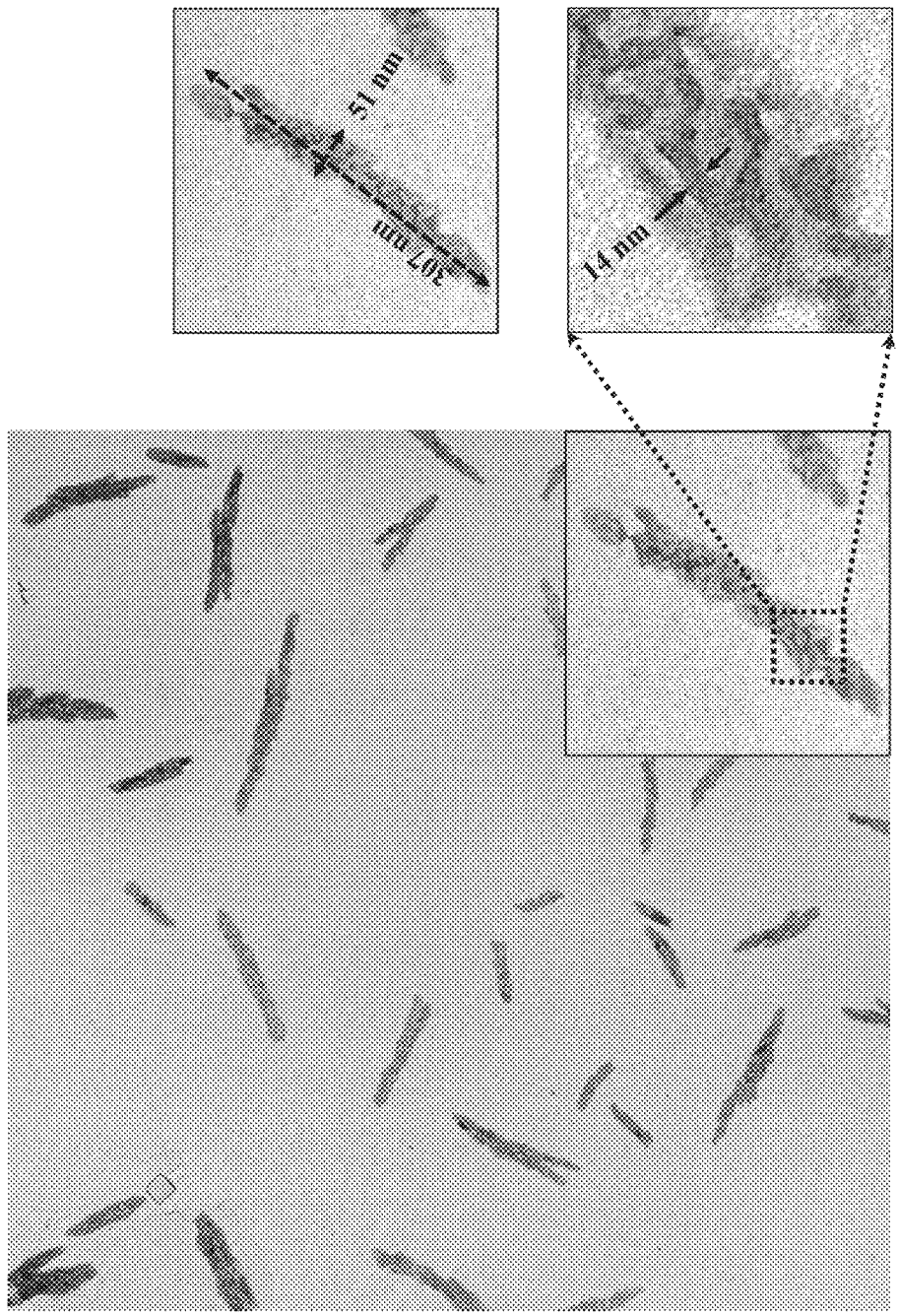
FIG. 23 Transmission electron microscopy image of FAM-CGY/Cy3-siRNA fiber complexes with an average length of 297±87 nm and width of 50±11 nm.
Figure 24:
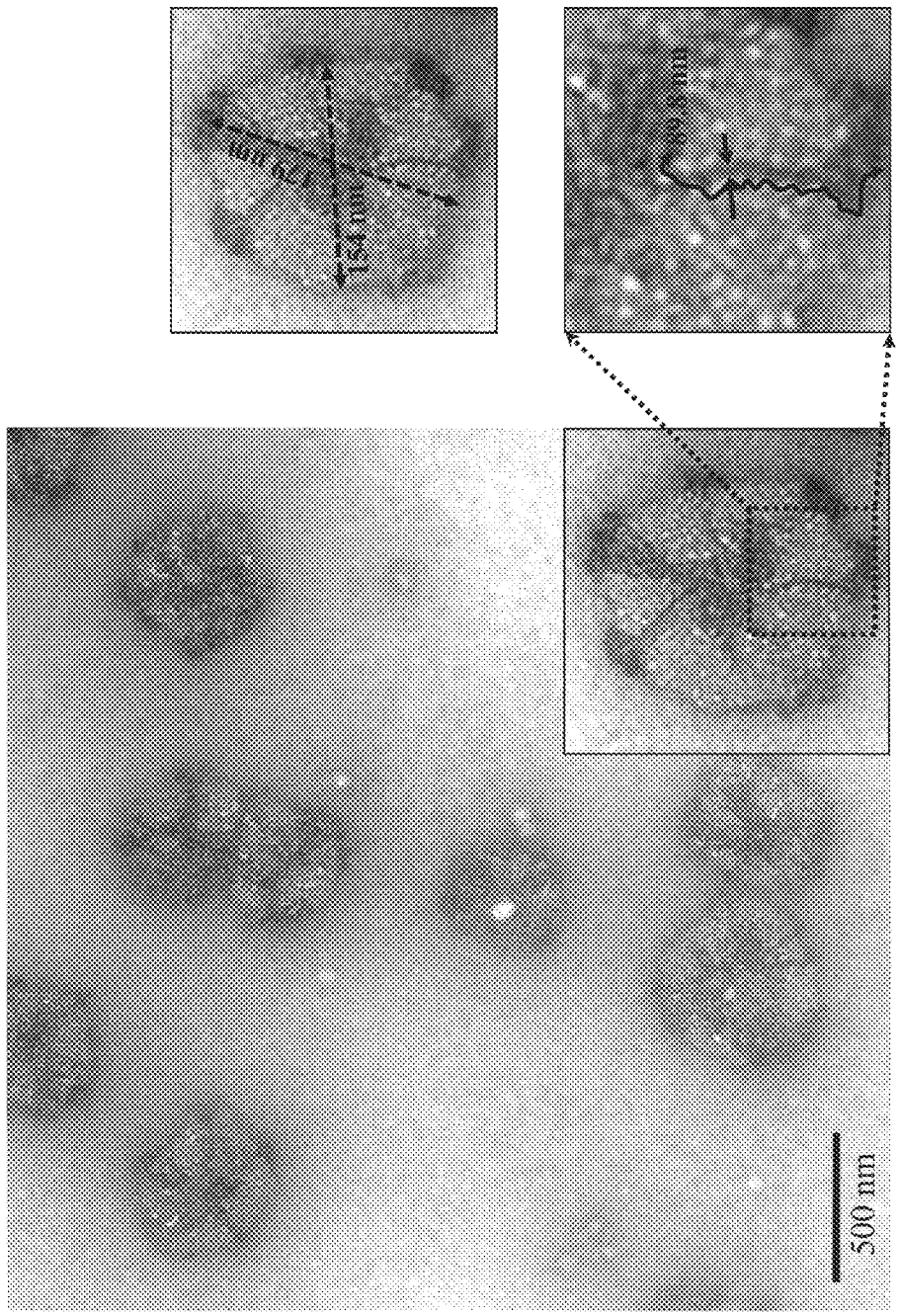
FIG. 24 Transmission electron microscopy image FAM-CGY/ciRNA (circular RNA) nanoparticles complexes with an average diameter of 180±29.
Figure 25A:
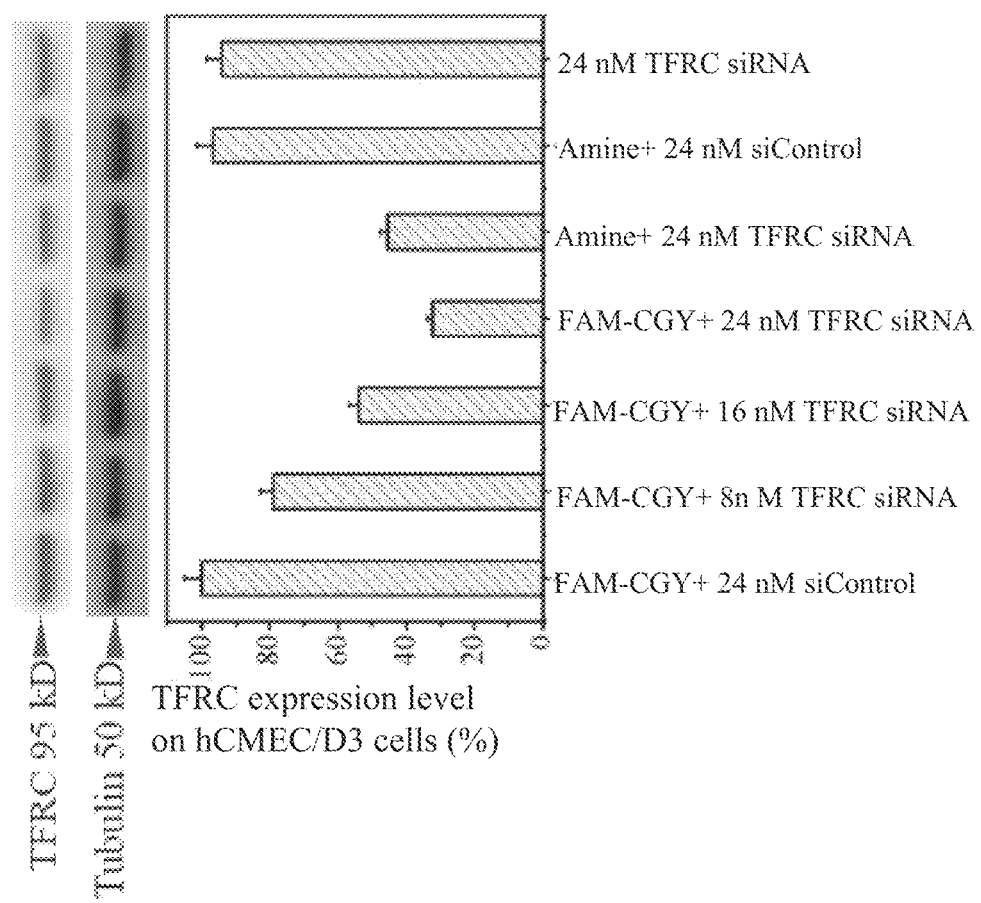
FIG. 25A. Suppression of transferrin receptor expression by different amounts of TFRC siRNA with or without complex formation with FAM-CGY. Transferrin receptor expression was measured 72 h after transfection.
Figure 25B:
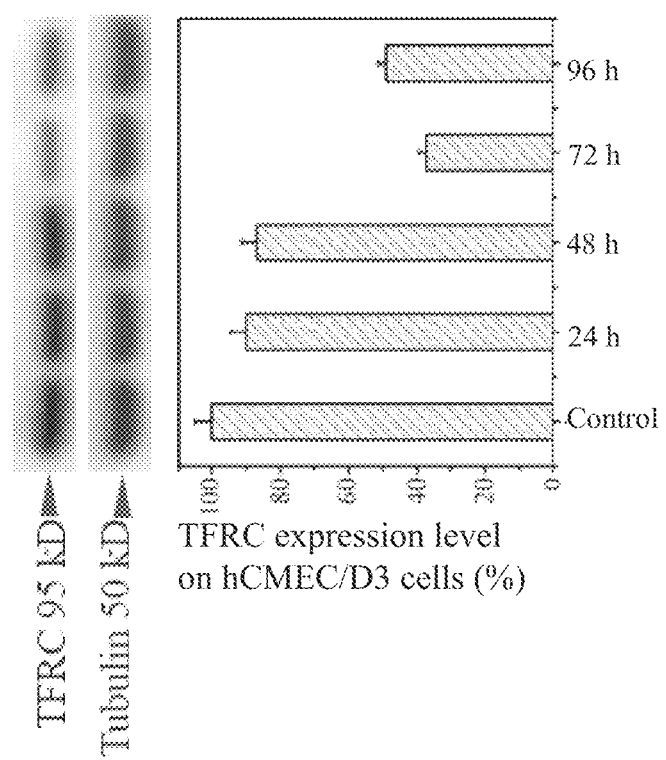
FIG. 25B. Time dependent downregulation of the transferrin receptor by TFRC siRNA/FAM-CGY complexes.

The siRNA efficacy was investigated by subjecting hCMEC/D3 cells to functional TFRC siRNA/FAM-CGY complexes (FIG. 23).

The intracellular distributions of siRNA complexed with the FAM-CGY nanoparticles were observed by fluorescent microscopy using Cy3-fluorescence labeled siRNA. In vitro gene silencing experiments were performed in hCMEC/D3 cells using the TFRC siRNA and a scrambled siRNA as a negative controls. The level of TFRC expression in hCMEC/D3 cells treated with different siRNA/FAM-CGY formulations were investigated by western blot.

Cells treated with the scrambled siRNA complexes do not give rise to any significant gene silencing even when using up to 24 nM siRNA mixed with FAM-CGY or siPORT Amine (Amine). In contrast, TFRC gene expression is slightly reduced by TFRC siRNA/FAM-CGY complexes containing 8 nM siRNA. When using TFRC siRNA up to 24 nM, the TFRC siRNA/FAM-CGY complexes efficiently inhibit TFRC gene expression down to 32.4% after 72 h of transfection. The siRNA/FAM-CGY delivery system showed a better silencing efficiency than siRNA/Amine which leads to 45.5% TFRC knockdown. Moreover, the siRNA/FAM-CGY complex transfection is time dependent. After 24 hours and 48 hours, only 20% gene expression knockdown is detected, while after 72 hours significantly more knockdown is observed.

Example 9: Cytotoxicity of Cy3-siRNA/FAM-CGY

The cytoxicity of FAM-CGY peptide and siRNA/FAM-CGY complex was evaluated by lactase dehydrogenase (LDH) assay (FIG. 26). The hCMEC/D3 cells were incubated with different concentrations of the peptide (from 1 to 20 µM) and different formulations of siRNA/FAM-CGY complexes for 24 h. The viability of cells without treatment was used as a control. The LDH assay has means of measuring the membrane integrity as a function of the amount of cytoplasmic LDH leaked into the medium. Compared to the control in FIG. 26a, the LDH leakage in the medium for the groups treated with different concentrations of the peptide did not significantly increase. Thus, there were no significant differences observed between the groups treated with FAM-CGY, FAM-d-CGY and CGY-FAM. A 30% LDH leakage was observed in cells treated with siRNA/Amine group, indicated that it was more toxic than the siRNA/FAM-CGY complexes.

These results indicate that there is no significant cytotoxicity observed for the FAM-CGY peptide or the siRNA/FAM-CGY complexes.

Example 10: Light-Triggered Release siRNA

To evaluate the intracellular release of siRNA loaded on FAM-CGY nanoparticles by illumination, Cy3-siRNA was complexed with FAM-CGY at molar ratio of 1:200 (Cy3-siRNA: FAM-CGY) in 50 µL saline at a concentration of 20 µM FAM-CGY. After 30 min incubation, the Cy3-siRNA/FAM-CGY complex was diluted with 150 µL 5% FBS cell medium to a final concentration of 5 µM FAM-CGY. hCMEC/D3 cells were seeded in 8-well Lab-Tek chamber slides (Nunc, Naperville, Ill.) (2×10$^4$/cm$^2$) and grown for 24 h. The cells were then washed with pre-warm PBS and treated with 200 µL complexes. After 24 h of incubation, the nuclei was stained with Hoechest 33342 (5 µg/mL) for 10 min and cells were rinsed three times with pre-warmed PBS. The cells were irradiated with the 488 nm light at different time points 0, 2, 2.30, 4 or 6 minutes passed through the 63× objective lens, and the images were each recorded at 30 s by fluorescent microscopy using filters GFP (Ex BP 470/40, Em BP 525/50), Cy3 (Ex BP 555/25, Em BP 605/52) and A4 (Ex BP 360/40, Em 470/40), respectively. The fluorescence intensity of the FAM-CGY peptide, Cy3-siRNA and Hoechest 33342 (nucleus) in the cytoplasm along specific area were quantified by software LAS AF Lite 6.0 (Leica, Germany) (FIG. 29).

FAM-CGY is released from internalized vesicles after between 2.5 and 4 minutes of light exposure.

Example 11: Preparation of Liposomes

F-Liposomes consisting of phospholipids, cholesterol, and functionalized coupling lipid (MPB-PE) at a molar ratio of DPPC:Cholesterol:DSPE-PEG:DSPE-PEG-MPB at a ratio of 7:2.5:0.025:0.025 were produced from lipid films hydrated with PBS. The final concentration was 10 µmol lipid/ml buffer. The hydration was performed in a water bath at 56° C. for 30 min. The resulting multilamellar vesicles were extruded (LiposoFast Extruder) 21 times through a polycarbonate filter (Avanti) with a pore size of 100 nm. The liposome size was determined by NanoSight LM20 (NanoSight, Amesbury, United Kingdom). Liposomes were labeled with red fluorescent phospholipid (16:0 Liss Rhod PE [1,2-dipalmitoyl-sn-glycero-3-phosphoethanolamine-N-(lissamine rhodamine B sulfonyl) (ammonium salt)]) or green fluorescent phospholipid (18:1 PE CF [1,2-dioleoyl-sn-glycero-3-phosphoethanolamine-N-(carboxyfluorescein) (ammonium salt)]).

Coupling Peptides to Liposomes

Peptides (CGY-peptide or GYR-GYR-peptide (that is a dimer of CGY-peptide)) were reduced using 2 mM Bond-Breaker TCEP (Pierce) under Nitrogen atmosphere for 1 h at 37° C. After gel filtration using a sepharose CL-4B column, for removing TCEP. Reduced peptide was incubated with preformed maleimide-containing liposomes (The molar ratio of phospholipids to peptide was 1 µmol to 1 nmol) under nitrogen atmosphere overnight at room temperature. Unreacted maleimide groups were inactivated by incubation with 0.5 mM cysteine for 30 min at room temperature. For removing non-conjugated peptides the mixture was centrifuged 3 times at 75.000 rpm for 30 min at 4° C. and the resuspended in PBS. Then the phospholipid concentration was again measured, and for indirectly measuring the amount of peptides that has been bond to the liposomes, the peptide concentration in supernatant was measured by Bradford assay method. Conjugated liposome was characterized by SDS-PAGE and measuring the size by NanoSight instrument.

Uptake study of Conjugated Peptides by FACS

The cells used were human adult brain endothelial cell line hCMEC/D3 were grown in endothelial growth medium 2 (EGM-2, Lonza, UK) supplemented with fetal bovine serum (FBS) 5%, hydrocortisone 1.4 µM, basic fibroblast growth factor 1 ng/mL, penstrep 1% and HEPES 10 nM in 24 well tissue culture plates. The cells were used at 70% confluence (corresponding cells to $6 \times 10^4$ to $8 \times 10^4$ cells) were incubated with liposomes labeled with 0.2 µmol RED or GREEN fluorescently-tagged phospholipid (F-liposomes) and bearing the peptide conjugate or liposomes attached to fluorescent CGY or scrambled CGY (e.g., FAM-CGY, CGY-FAM and FAM-CGY Scrambled 2). Liposomes were added to the cells (in 200 µL medium) and after overnight incubation the cells were washed with 1% BSA in PBS then detached from cell culture dishes using trypsin (Sigma-Aldrich, Inc). The cells were analyzed by flow cytometry (FACS Calibur, Becton Dickinson) (FIG. 39).

F-Liposome and FAM linked to CGY-peptide or GYR-GYR-peptides in any position bind to hCMEC/D3 cells in a greater number than the control and F-Liposome alone.

Example 12: Double Peptide FAM-GYR-GYR Experiments

The different cellular uptake of FAM-CGY and FAM-GYR-GYR peptides in hCMEC/D3 cells was investigated by flow cytometry (FACS). hCMEC/D3 cells ($2 \times 10^4/cm^2$) were seeded on 24-well plate (Corning, N.Y.) and grown 2 days at 37° C. and 5% $CO_2$ in order to reach 60%-70% confluency. The cells were washed 3 times with pre-heated PBS. The peptide uptake experiments were initiated by adding 200 µL of a range of FAM-CGY and FAM-GYR-GYR in different concentrations (1-10 µM/L, diluted in cell medium containing serum). The double peptide contains the sequence Gly-Tyr-Arg-Pro-Val-His-Asn-Ile-Arg-Gly-His-Trp-Ala-Pro-Gly-Gly-Gly-Tyr-Arg-Pro-Val-His-Asn-Ile-Arg-Gly-His-Trp-Ala-Pro-Gly (SEQ ID NO.2) and optionally has an N-terminal cysteine residue.

After 24 h incubation at 37° C. with 5% $CO_2$, each chamber was washed with pre-heated PBS 3 times, and harvested by trypsinization. A total of 10,000 cells were analyzed by flow cytometry (FACS Array™ Cell Analysis, BD, USA) (FIG. 35).

FAM-GYR-GYR peptide/structures show considerably higher uptake by hCMEC/D3 cells compared with FAM-CGY peptide at all tested concentrations. The double peptide shows excellent target binding, even increased when compared with the single sequence and allows for delivery of larger molecules (e.g., DNA). Trials illustrated utilized a double peptide with a glycine residue between the two peptide sequence elements but other amino acid linkers, or other non-amino acid linker molecules can be used to create such a molecule.

Example 13: Transfection of Cy3-siRNA/FAM-GYR-GYR Complex on hCMEC/D3 Cells

Cy3-siRNA was complexed with FAM-GYR-GYR at a molar ratio of 1:200 (Cy3-siRNA: FAM-CGY) in 50 µL saline at a concentration of 20 µM/L FAM-GYR-GYR. After 30 min incubation, the Cy3-siRNA/FAM-GYR-GYR complex was diluted with 150 µL 5% FBS cell medium to a final concentration of 5 µM/L FAM-GYR-GYR. hCMEC/D3 cells were seeded in 8-well Lab-Tek chamber slides (Nunc, Naperville, Ill.) ($2 \times 10^4/cm^2$) and grown for 24 h. The cells were then washed with pre-warm PBS and treated with 200 µL Cy3-siRNA/FAM-GYR-GYR complexes. After 1 or 4 h of incubation, the nuclei was stained with Hoechest 33342 (5 µg/mL) for 10 min and cells were rinsed three times with pre-warmed PBS. Finally, the cells were observed with a Leica fluorescent microscopy (Leica AF6000LX, Germany) using a 63×TIRF oil objective and filters GFP (Ex BP 470/40, Em BP 525/50), Cy3 (Ex BP 555/25, Em BP 605/52) and A4 (Ex BP 360/40, Em 470/40), respectively (FIG. 36).

This trial demonstrates that Cy3-siRNA/FAM-GYR-GYR complex internalizes into hCMEC/D3 cells.

Example 14: Binding a Hydrophobic Moiety to a Peptide-Formed Nanoparticle

Caprylic acid conjugated CGY peptide (Caprylic-CGY) was synthesized by a solid phase method. Peptides were purified by preparative HPLC and characterized by analytical HPLC and mass spectrometry ($M_w$=1946.29, Purity: 98.26%). The lyophilized peptides were dissolved into dimethyl sulfoxide (DMSO) with a peptide concentration of 500 µM and stored at −80° C. For the self-assembly, the 500 µM stock solution of Caprylic-CGY was diluted into MQ water with the final concentration of 5 µM and incubated at room temperature for 1 h. The size of self-assembly of Caprylic-CGY was performed by Nanoparticle Tracking Analysis (NTA) (LM20, NanoSight, Amesbury, United Kingdom) with a sample chamber with a 405 nm blue laser and a Viton fluoroelastomer O-ring. As seen in FIG. 41, The mean size of self-assembly is 117±74 nm and with a mode of 86 nm.

Example 15: Rhodamine as a Drug or Fluorescent Molecule Attached to a Peptide

Peptidic complexes were formed by drop addition of cargoes (FAM-(C)-NAP, FAM-GYR, FAM-NAP, FAM) to 80 µM rhodamine-conjugated CGY peptide (Rh-CGY) or 80 µM CGY peptide (Table X) in MilliQ (MQ) water with equatable liquid volume and incubated for 60 min. The mixture was diluted with MQ water to a final Rh-CGY or CGY peptide concentration of 10 µM. The peptidic complexes were characterized by NTA for size and electron microscopy (EM) for mophology. Western blot was also employed to detect disulfide bond, which form between the cargo and Rh-CGY peptide or CGY peptide. Briefly, the peptide or complex samples were loaded on 10% Bis-Tris mini gels (Invitrogen, Calif., USA) and subjected to electrophoresis. The separated samples were electrophoretically transferred to PVDF membranes by use of an iBlot™ Gel Transfer Device (Life Technologies, USA). Membranes were blocked for 1 h at room temperature in 3% BSA/TBST (137 mM Sodium Chloride, 20 mM Tris, 0.1% Tween-20, pH 7.6), and incubated over night at 4° C. with HRP-Goat anti-Fluorescein antibody (diluted 1:1000 in 2% BSA/TBST). For detection, membranes were incubated with Novex® ECL Chemiluminescent Substrate Reagent Kit (Invitrogen, Calif., USA).

Delivery peptide to hCMEC/D3 cells. In vitro delivery experiments were performed in hCMEC/D3 cells. Briefly, the peptidic complexes were firstly prepared with concentration of 80 μM Rh-CGY or 80 μM CGY peptide, and diluted with cell medium to 10 μM Rh-CGY or CGY peptide. The complex solutions were added to hCMEC/D3 cells following 24 h incubation. Live cell images were obtained by widefield microscopy, and the intercellular fluorescence intensity was quantified by FACS.

To investigate the effect of hydrophobic block FAM in peptide self-assembly, another fluorophore Rhdomine B was choose to conjugate with CGY peptide in the N-terminal, which termed Rh-CGY (molecular mass 2244.69 g/mol). The measurement of NTA indicated that the Rh-CGY can also easily self-assembly. FIG. 41 represents the size distribution of Rh-CGY supermolecular with narrow peak and a weak trailing fraction. The average size of Rh-CGY supermolecular was 131±60 nm with a modal size of 94 nm (FIG. 41a). Also the supermolecular of Rh-CGY can efficiently enter the hCMEC/D3 cells (FIG. 41b). In order to investigate the functionality of Rh-CGY peptide, a model cargo of FAM-(C)-NAP peptide was selected to co-assemble with Rh-CGY peptide. From the Western blot data, FAM-(C)-NAP peptide form disulfide bond with Rh-CGY peptide (FIG. 42). The lanes of the Western blot are as follows: Lane 1: Rh-CGY peptide, Lane 2: FAM-(C)-NAP peptide, Lane 3: CGY peptide, Lane 4: FAM-GYR peptide, Lane 5: Rh-CGY/FAM-(C)-NAP peptidic complex, Lane 6: Rh-CGY/FAM-GYR peptidic complex, Lane 7: CGY/FAM-(C)-NAP peptidic complex.

Because of this disulfide bond and the π-π interaction between the fluorophore of FAM and Rhodamine, the FAM-(C)-NAP peptide can form stable complex with Rh-CGY peptide. The average size is 99±41 nm (FIG. 43a). The mixture of Rh-CGY and FAM-(C)-NAP self-assembled into not only the nanoparticles but also into fibres based on the EM observation (FIG. 43b). With the assistance of Rh-CGY peptide, the FAM-(C)-NAP peptide can be easily delivered into hCMEC/D3 cells (FIG. 43c, d, e). When FAM-(C)-NAP peptide mixed with CGY peptide, it can also form a disulfide bond with CGY peptide (FIG. 42).

However, this mixture cannot form any particles and the mixture of FAM-(C)-NAP and CGY peptide cannot deliver FAM-(C)-NAP peptide into cells (FIG. 43c). When cysteine amino acid was deleted from the sequence of the FAM-(C)-NAP peptide, FAM-NAP peptide was poorly taken up by hCMEC/D3 cells (FIG. 43c). When it was co-incubated with Rh-CYG peptide, it did not form disulfide bond with Rh-CGY peptide. FAM-NAP peptide did not efficiently cross cell membrane even after co-incubated with Rh-CGY peptide (FIG. 43c). These observations indicated that forming disulfide bond is one of key factor to delivery FAM-(C)-NAP peptide into the cells. This can be most readily accomplished with the inclusion of a cysteine residue, and such inclusion can be at many different points of the sequence, including at the N-terminus, at the C-terminus, or internally.

In another case, FAM-GYR peptide can form stable particles/fiber complex with Rh-CGY peptide with the mean size of 82±43 nm (FIG. 44a,b). FAM-GYR peptide trapped in Rh-CGY peptide was significantly delivered into hCMEC/D3 cells compared with FAM-GYR peptide alone (FIG. 44c, d). The FAM-GYR peptide does not contain the cysteine, and cannot form disulfide bond to cross link with Rh-CGY peptide (FIG. 42). But the main sequence of FAM-GYR was the same with Rh-CGY peptide, the amino acid in FAM-GYR and Rh-CGY peptide, such as Arg, Trp, can interact with each other to form hydrogen bond and π-π interaction. This result demonstrated that the Rh-CGY/FAM-GYR peptidic mixture can self-assemble into stable complexes even without the disulfide bond (FIG. 44a,b). Cells were labelled with Hoechest 33342 (blue).

To further prove this concept, the fluorophore FAM alone was co-incubated with the Rh-CGY peptide. FAM can not been entrapped in the Rh-CGY peptidic complexes. The mixture of FAM and Rh-CGY peptide can not enhance the uptake of FAM in hCMEC/D3 cells (FIG. 43c). This suggests that the sequence of FAM-GYR peptide is specific to form stable particles with Rh-CGY peptide and improve the uptake in hCMEC/D3 cells. Rh-CGY peptide can co-assemble with the cargo peptide with specific properties to fabricate stable nanoparticle/fiber complex because of forming disulfide bond or hydrogen bond and π-π interaction, and deliver the cargo peptide into hCMEC/D3 cells. Rh-CGY peptide is a potential candidate of peptidic-based delivery system for the CNS disease.

Example 16: Plamsid Transfection Mediated by Double Peptide

To evaluate double peptide (DP)-mediated gene transfection, different concentrations of DP and constant amounts of pcDNA3.1NT-GFP expression plasmid (0.3 μg) (the peptide/DNA change ration of 1:10, 1:20 and 1:40 were investigated in this study) were mixed into 50 μL serum free media, and complexes were formed for 1 h at room temperature, after which another 150 μL serum free media was added (total volume of peptide/DNA complex was 200 μL). The cultured hCMEC/D3 cells ($2 \times 10^4$ cells) were overlaid with 200 μL peptide/DNA complex, followed by incubation for 4 h at 37° C. in 5% $CO_2$ atmosphere. The cultures were then a washed once with serum-free media and transferred to complete media containing 5% serum for growth. After 48 h, GFP gene expressions were monitored by fluorescence microscopy. Lipofectamine® 2000-mediated transfections were performed as described by the manufacturer's protocol (Life Technologies, Calif., USA).

Since the double peptide (DP) has four positive charge amine acids in each peptide molecular, it is possible for DP to bind with DNA by electrostatic interaction and form stable complex. In order to test the possibility of DP-mediated gene delivery, DP was mixed with plasmid DNA encoding GFP in different charge ratios from 10:1 to 40:1. Transfection was performed with different peptide/DNA charge ratios in hCMEC/D3 cells, and transfection efficiencies were evaluated using fluorescence microscopic analysis of GFP expression. The results showed that DP was able to mediate translocation of plasmids into cells when the charge ratios of peptide/DNA more than 20 (FIG. 45). And the transfection efficiency of peptide/DNA with charge ratio 40:1 was comparable with commercial transfection reagent Lipofectamine® 2000 based on the intensity of fluorescence microscopy signal. But compared with the DP, the Lipofectamine® 2000, the cationic lipid based gene delivery system, can lead to higher cytotoxicity. The results indicated that the DP is a potential safe delivery system of plasmid for brain targeting. Cells were labelled with Hoechest 33342 (blue).

Example 17: Targeting of the Brain In Vivo

BALB/c nude mice received 5 μM of FAM-CGY peptide or 10 μM of Rh-CGY peptide (the final concentration in blood) intravenously and subjected to optical imaging at various time points post-injection. The in vivo fluorescence imaging was performed using the IVIS Imaging System 200 Series and analyzed using the IVIS Living Imaging 3.0 software (Caliper Life Sciences, Alameda, Calif., USA). Optimized GFP filter or Dsred filter sets were used for acquiring FAM-CGY or Rh-CGY peptide fluorescence in vivo, respectively. After the whole body mice images were recorded, the mice were sacrificed and the organs were dissected and subjected to ex vivo fluorescence imaging. Data in FIG. 46 shows brain targeting of the described invention as well as localization to organs of the reticuloendothelial system (liver, spleen). Kidney accumulation may represent single chain conjugates (since they are in equilibrium with nanoparticles). Some lung accumulation also occurs (not shown).

Example 18: Sections of Brain in Peptide-Injected Mouse

Organs were fixed in a PBS solution of 4% paraformaldehyde overnight. After that, samples were placed in 15% sucrose PBS solution for 12 h, which was then replaced with 30% sucrose for 24 h. The samples were then embedded in Tissue Tek O.C.T. compound (Mc Cormick, USA) and frozen at −60° C. in isopentane. Frozen sections, 7 mm thick, were then prepared with a cryotome and stained with 10 μg/mL DAPI for 10 min. After PBS washing, the sections were observed under a fluorescence microscope. The results in FIG. 47 show fluorescent signals in the brain tissue, with green coloration representing the labeled peptide and blue being DAPI.

Example 19: Imaging of Peptide Conjugate Aggregate Structures

Atomic force microscopy (AFM) analysis of FAM-CGY revealed the presence of a heterogeneous nanoparticle and 'nanoparticle-fibre' network system, where some nanoparticles intercept fibres or are cross-linked by the fibres (FIG. 48a). Nanoparticle may be perceived as nucleation sites where several 'nanofiber-like' structures of variable dimensions and height emerge. Due to the heterogeneous nature of the network, nanoparticle tracking analysis (NTA) was employed for possible size distribution determination and counting of the observed species in the nanoparticle and 'nanoparticle-fiber' network system.

Figure 48C:
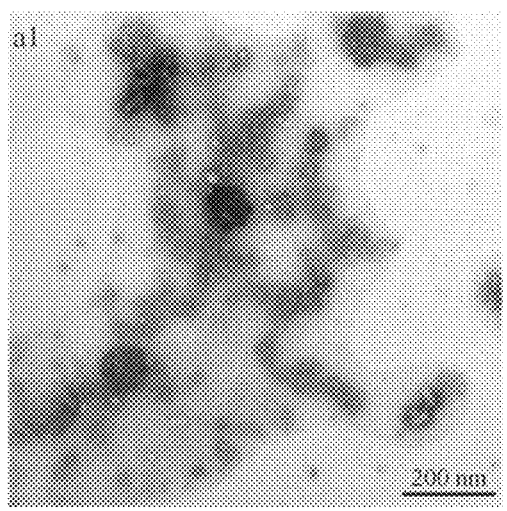
Figure 48D:
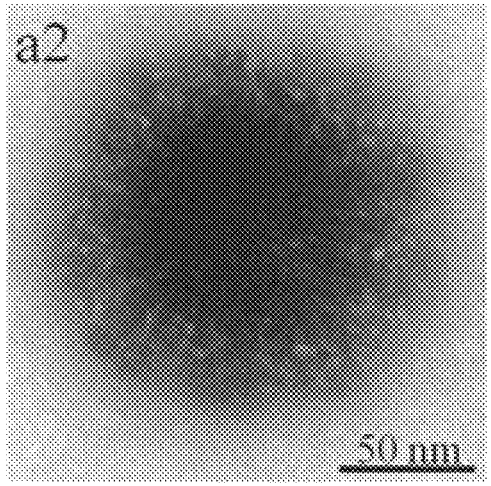
Figure 48E:
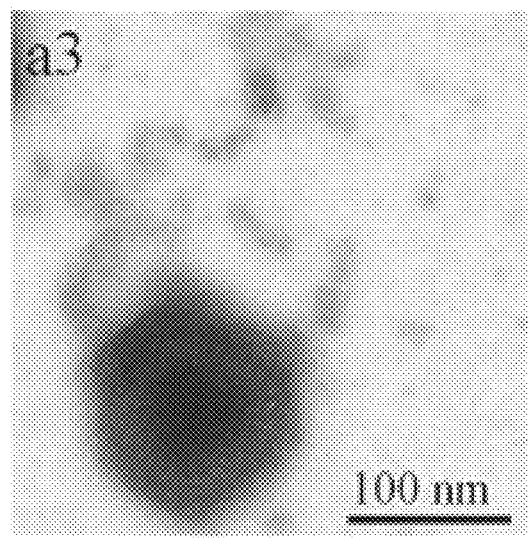
Figure 48F:
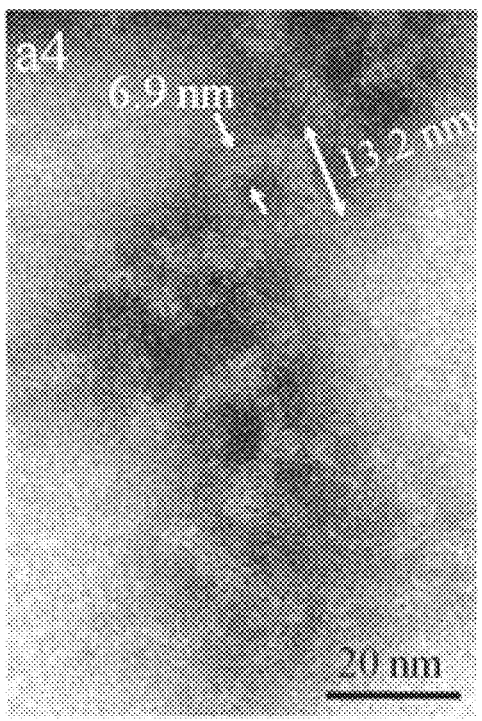
Figure 48G:
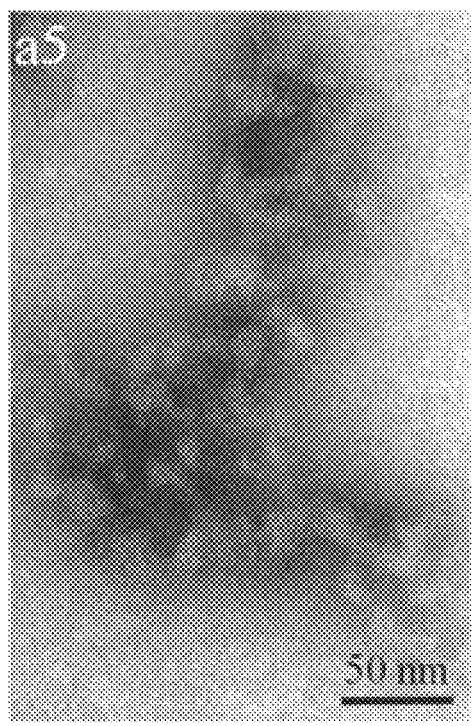

Transmission electron microscopy (TEM) investigation of the 'nanoparticle-fibre' network showed that the 'spherical-like' structures are of 'core-shell' morphology (FIG. 48c-g). The core component (FIG. 4a1) is most likely an assembly of condensed unimers, dimers and/or oligomers of different arrangements (e.g., dimers with anti-parallel arrangements) and amenable to further growth through multiple interactive forces, which eventually forms elongated 'hair-like' projections of the shell component (FIGS. 4a3, 4b1 and 4b2). Different nanofiber network morphologies, predominantly of twisted elongated architectures emanating from the shell component of the 'core-shell' structures, are visible (FIG. 48c, e-g).

The invention claimed is:

1. A method for cellular delivery of a therapeutic from an aggregate, comprising administering a pharmaceutical composition which comprises a pharmaceutically acceptable carrier and aggregate formed from a peptide-conjugate wherein the peptide-conjugate comprises:
 a peptide that is a substrate for a transferrin receptor (TFRC) or a receptor for advanced glycation end product (RAGE) and that is the peptide of SEQ ID NO. 1, the peptide of SEQ ID NO. 2 or a peptide which is at least 80% identical to the peptide of SEQ ID NOs. 1 or 2;
 a cysteine residue at the N-terminus of the peptide wherein a thiol group from the cysteine residue forms a disulfide bridge with other peptide-conjugates to promote self-assembly of the aggregate;
 at least one hydrophobic molecule covalently attached to the amino group of the cysteine residue that promotes formation of the aggregate, wherein the hydrophobic molecule is selected from a compound that has at least one carbocyclic or heterocyclic ring or a linear carbon chain of at least three carbon atoms, or a photoactive molecule or a fluororophore that operates at either visible or near-infrared spectrum;
 an optional linker located between the at least one hydrophobic molecule and the peptide;
 and a therapeutic agent or pharmaceutically acceptable salt or ester thereof.

2. The method of claim 1, wherein the aggregate is in a particulate form having a particle size of at least 2 nm in diameter or in a fiber form having a width of at least 2 nm and a length of at least 5 nm.

3. The method of claim 1, wherein the therapeutic agent is a nucleic acid comprising at least two nucleotides.

4. The method of claim 3, wherein the nucleic acid is in the form of siRNA, circular siRNA, linear DNA, plasmid DNA, shRNA, miRNA, an antisense molecule, locked nucleic acids, aptamer, peptide nucleic acids, splice modulating oligonucleotide, nucleic acid attached to an enzyme, therapeutic nucleic acid and an expression conjugate that comprises a nucleic acid that encodes a therapeutic protein.

5. The method of claim 3, wherein the therapeutic agent is covalently linked to at least one hydrophobic molecule selected from a compound that has at least one carbocyclic or heterocyclic ring.

6. The method of claim 5, wherein the hydrophobic molecule linked to the therapeutic agent is a photosensitive molecule.

7. The method of claim 6, where the photosensitive molecule is a fluorophore operating in the visible or near infrared spectrum.

8. The method of claim 7, further comprising irradiating the aggregate with electromagnetic radiation.

9. The method of claim 8, wherein the release of the therapeutic agent is accelerated following exposure to a light source with a broad range of electromagnetic wavelength.

10. The method of claim 1, wherein the therapeutic agent is physically entrapped within the aggregate.

11. The method of claim 1, wherein the therapeutic agent is selected from: an active pharmaceutical grade nucleic acid, a pharmaceutical grade pro-drug nucleic acid, a pharmaceutical nucleic acid conjugate and a diagnostic nucleic acid agent.

12. The method claim 1, wherein the pharmaceutical composition is in a solid form.

13. The method of claim 1, wherein the pharmaceutical composition is in a liquid form.

14. The method claim 1, further comprising contacting a mammalian cell having a transferrin receptor (TFRC) or a receptor for advanced glycation end-product (RAGE) or both receptors with the aggregate.

15. A method for delivering a therapeutically active nucleic acid comprising:
 providing a pharmaceutically acceptable carrier and aggregate formed from a peptide-conjugate wherein the peptide-conjugate comprises:
  a peptide that is a substrate for a transferrin receptor (TFRC) or a receptor for advanced glycation end product (RAGE) and that is the peptide of SEQ ID NO. 1, the peptide of SEQ ID NO. 2 or a peptide which is at least 80% identical to the peptide of SEQ ID NOs. 1 or 2;
  a cysteine residue at the N-terminus of the peptide wherein a thiol group from the cysteine residue forms a disulfide bridge with other peptide-conjugates to promote self-assembly of the aggregate;
  at least one hydrophobic molecule covalently attached to the amino group of the cysteine residue that promotes formation of the aggregate, wherein the hydrophobic molecule is selected from a compound that has at least one carbocyclic or heterocyclic ring or a linear carbon chain of at least three carbon atoms, or a photoactive molecule or a fluorophore that operates at either visible or near-infrared spectrum; and
  an optional linker located between the at least one hydrophobic molecule and the peptide;
  pharmaceutically acceptable salts or esters thereof wherein the aggregate further comprises a nucleic acid;
 contacting a mammalian cell having a transferrin receptor (TFRC) or a receptor for advanced glycation end-product (RAGE) or both receptors with the aggregate; and
 irradiating the aggregate with a photonic source thereby photodynamically releasing the nucleic acid.

16. The method of claim 15, wherein the mammalian cell is from a mammalian tissue selected from the gastrointestinal tract, bone marrow, liver, spleen, brain, kidney, lungs, pancreas, bladder, eye, skin, normal and pathologic blood vessels, and cancer cells.

17. The method of claim 15, wherein the contacting step further comprises administering an effective amount of the aggregate to a patient in need thereof to treat a disorder.

18. The method of claim 17, wherein the disorder is a central nervous system disorder, cancer, skin cancer, bladder cancer, cardiovascular disorder, atherosclerosis, eye disorder, or diabetes.

19. The method of claim 1, wherein the aggregate is either in the form of a spherical particle that associates with TFRC, or in the form of a fiber that associates with RAGE.

20. The method of claim 15, wherein the nucleic acid is in the form of siRNA, circular siRNA, linear DNA, plasmid DNA, shRNA, miRNA, an antisense molecule, locked nucleic acids, aptamer, peptide nucleic acids, splice modulating oligonucleotide, nucleic acid attached to an enzyme, therapeutic nucleic acid and an expression conjugate that comprises a nucleic acid that encodes a therapeutic protein.

* * * * *